(12) United States Patent
Wei et al.

(10) Patent No.: US 9,994,543 B2
(45) Date of Patent: Jun. 12, 2018

(54) PROCESSES AND INTERMEDIATES FOR THE PREPARATIONS OF ISOMER FREE PROSTAGLANDINS

(71) Applicant: CHIROGATE INTERNATIONAL INC., Yangmei (TW)

(72) Inventors: Shih-Yi Wei, Yangmei (TW); Yu-Chih Yeh, Yangmei (TW); Min-Kuan Hsu, Yangmei (TW); Li-Ta Kao, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days. days.

(21) Appl. No.: 14/802,072

(22) Filed: Jul. 17, 2015

(65) Prior Publication Data

US 2016/0016883 A1    Jan. 21, 2016

Related U.S. Application Data

(62) Division of application No. 13/967,473, filed on Aug. 15, 2013, now Pat. No. 9,115,109.

(51) Int. Cl.
| | |
|---|---|
| *C07D 313/00* | (2006.01) |
| *C07D 309/12* | (2006.01) |
| *C07C 51/347* | (2006.01) |
| *C07F 7/18* | (2006.01) |
| *C07C 59/72* | (2006.01) |
| *C07D 407/14* | (2006.01) |
| *C07D 407/12* | (2006.01) |
| *C07C 405/00* | (2006.01) |
| *C07C 69/608* | (2006.01) |
| *C07C 69/618* | (2006.01) |

(52) U.S. Cl.
CPC .......... *C07D 313/00* (2013.01); *C07C 51/347* (2013.01); *C07C 59/72* (2013.01); *C07C 69/608* (2013.01); *C07C 69/618* (2013.01); *C07C 405/00* (2013.01); *C07D 309/12* (2013.01); *C07D 407/12* (2013.01); *C07D 407/14* (2013.01); *C07F 7/1864* (2013.01); *C07C 2601/08* (2017.05)

(58) Field of Classification Search
CPC .................................................. C07D 313/00
USPC ....................................................... 546/269
See application file for complete search history.

(56) References Cited

U.S. PATENT DOCUMENTS

| 7,582,779 | B2 | 9/2009 | Wei et al. | |
|---|---|---|---|---|
| 8,476,471 | B2 * | 7/2013 | Yiannikouros | .... A61K 31/5575 560/121 |
| 2004/0023954 | A1 | 2/2004 | Ling et al. | |
| 2005/0209337 | A1 | 9/2005 | Gutman et al. | |
| 2008/0033176 | A1 | 2/2008 | Murata et al. | |
| 2009/0259058 | A1 | 10/2009 | Henschke et al. | |

FOREIGN PATENT DOCUMENTS

| EP | 1 886 992 A1 | 2/2008 | |
|---|---|---|---|
| EP | 2 143 712 A1 | 1/2010 | |
| JP | 2003-517441 A | 5/2003 | |
| JP | 2005/539014 A | 12/2005 | |
| JP | 2012-507552 A | 3/2012 | |
| JP | 2012-520294 A | 9/2012 | |
| JP | 2012/246301 A | 12/2012 | |
| WO | 00/18316 A2 | 4/2000 | |
| WO | 01/55101 A2 | 8/2001 | |
| WO | 02/090324 A1 | 11/2002 | |
| WO | 02/096898 A2 | 12/2002 | |
| WO | 2004/013119 A1 | 2/2004 | |
| WO | 2010/096123 A2 | 8/2010 | |
| WO | 2010/097672 A1 | 9/2010 | |
| WO | 2010/104344 A2 | 9/2010 | |
| WO | 2011/005505 A2 | 1/2011 | |
| WO | 2011/008756 A1 | 1/2011 | |
| WO | WO 2011095990 | * 11/2011 | ........... C07C 405/00 |
| WO | 2013/037479 A1 | 3/2013 | |

(Continued)

OTHER PUBLICATIONS

US 6,720,438, 04/2004, Gutman et al. (withdrawn)
Martynow et al. European Journal of Organic Chemistry (2007), (4), 689-703.*
Office Action with a Search Report dated Aug. 5, 2015 for Chinese Application No. 201410400057.0.
Office Action dated Mar. 24, 2015 for Japanese Application No. 2014-164880.
European Search Report dated Jan. 14, 2015 for EP Application No. 14180866.7-1451.
Martynow, J. G., et al., "A New Synthetic Approach to High-Purity (15R)-Latanoprost", Eur. J. Org. Chem. 2007, pp. 689-703.

(Continued)

*Primary Examiner* — Nizal S Chandrakumar
(74) *Attorney, Agent, or Firm* — Ladas & Parry LLP

(57) ABSTRACT

Novel processes for the preparation of a compound of Formula I-2 substantially free of the 5,6-trans isomer:

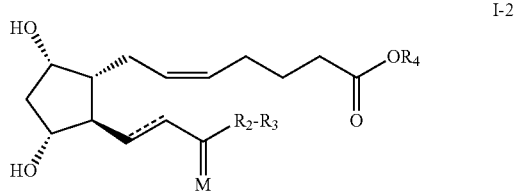

wherein

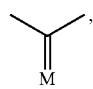

$R_2$, $R_3$ and $R_4$ are as defined in the specification are provided. Novel intermediates for the preparations of isomer free Prostaglandins and derivatives thereof are also provided.

4 Claims, No Drawings

(56) References Cited

FOREIGN PATENT DOCUMENTS

WO          2013/093528 A1      6/2013

OTHER PUBLICATIONS

Matsumura, Y., et al., "Synthesis of the highly potent prostanoid FP receptor agonist, AFP-168: a novel 15-deoxy-15,15-difluoroprostaglandin $F_{2\alpha}$ derivative", Tetrahedron Letters, 45, 2004, pp. 1527-1529.
Corey, E. J., et al., "Synthesis of Novel Macrocyclic Lactones in the Prostaglandin and Polyether Antibiotic Series", J. Am. Chem. Soc., vol. 97, No. 3, Feb. 5, 1975, pp. 653-654.
Bundy, G. L., et al., Synthesis and Biological Activity of Prostaglandin Lactones, J. Med. Chem., vol. 26, No. 8, Aug. 1983, pp. 1089-1099.

\* cited by examiner

PROCESSES AND INTERMEDIATES FOR THE PREPARATIONS OF ISOMER FREE PROSTAGLANDINS

CROSS REFERENCE APPLICATIONS

This application is a Divisional of U.S. patent application Ser. No. 13/967,473 filed Aug. 15, 2013, the content of which is incorporated herein by reference.

FIELD OF THE INVENTION

The present invention relates to novel processes and intermediates for the preparations of isomer free Prostaglandins and the derivatives thereof.

BACKGROUND OF THE INVENTION

Prostaglandin ester analogues of the following Formula I-2

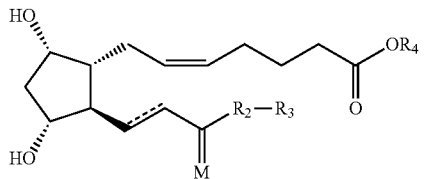

wherein

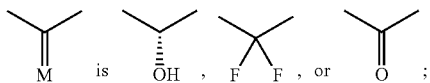

$====$ is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl; and $R_4$ is $C_{1-7}$-alkyl, such as, Latanoprost, Isopropyl unoprostone, Isopropyl cloprostenol, Travoprost and Tafluprost have been used in the management of open-angle glaucoma. The Prostaglandin ester analogues of Formula I-2 have been shown to have significantly greater hypotensive potency than the parent compound, presumably as a result of their more effective penetration through the cornea. They reduce intra-ocular pressure by enhancing uveoscleral outflow, and may also have some effect on trabecular meshwork as well.

As shown in the following Scheme A:

Scheme A

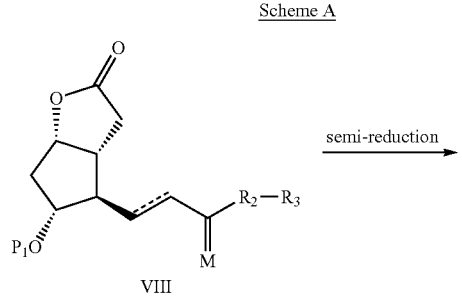

most of the Prostaglandin ester analogues of Formula I-2 disclosed in the prior art, such as in WO02096898, EP1886992, EP2143712, JP2012246301, U.S. Pat. No. 6,720,438, US2008033176, WO2010097672, and U.S. Pat. No. 7,582,779 were obtained by first synthesizing a Lactone VIII, wherein M is
$\underset{OP_2}{\vert}$ , $\underset{OP_2}{\vert}$ , or $\underset{F\ \ F}{\vert}$ , or is a protective group of carbonyl group; $P_1$ and $P_2$ are protective groups for the hydroxyl groups; $====$ is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl and then conducting a semi-reduction of the Lactone to get a Lactol VII which was underwent a Wittig reaction to produce a C5~C6 configuration cis-olefin of Formula IV-1, which was then converted to Prostaglandin ester analogues of Formula I-2. No matter which kind of Wittig reagents or solvents were used or what was the temperature for the Wittig reaction, it was inevitable that about 2~10% 5,6-trans isomer of the compound of Formula IV-1 would be produced. If the starting material already contained a trace amount of an isomer (e.g., 15β-isomer or enantiomer), the resultant compound of Formula IV-1 would contain the corresponding isomer.

As shown in the following Scheme B:

Scheme B

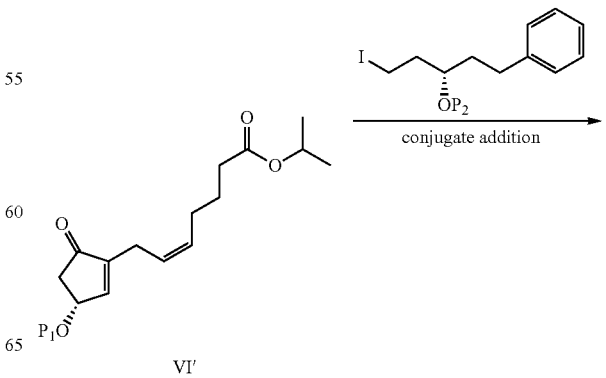

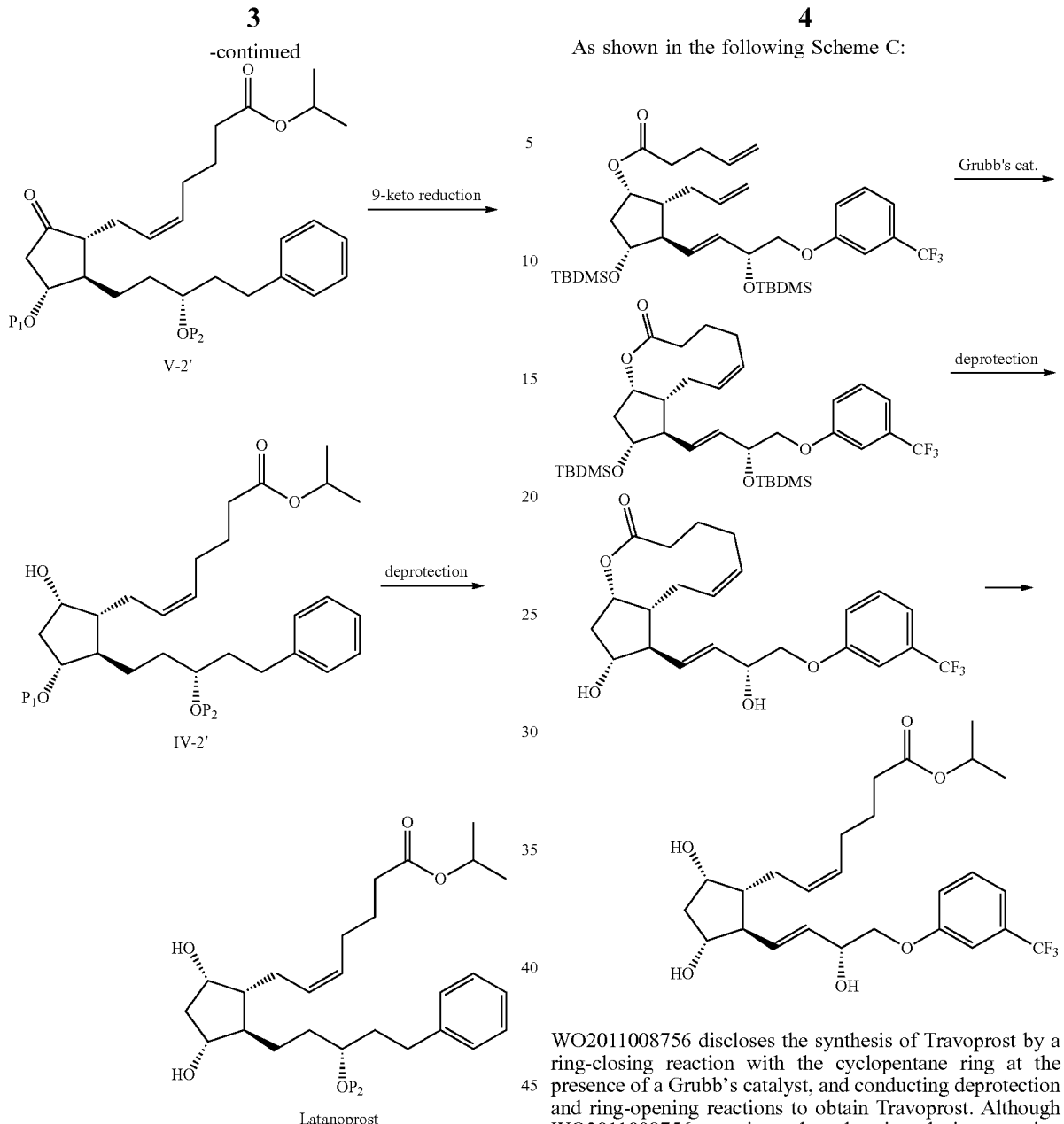

some of the syntheses of Prostaglandin ester analogues of Formula I-2, for example, latanoprost disclosed in the prior art, such as WO02090324 and US2009259058, were involved a conjugate addition of a cyclopentenone VI' with a ω-side chain unit IX' to obtain a cyclopentanone V-2', which was then underwent a 9-keto reduction to get a protected latanoprost IV-2'. Nevertheless, such a conjugate addition could not avoid the generation of a trace amount of 8β-isomer and 12α-isomer, nor could it avoid the generation of a trace amount of 9β-isomer. In addition, commercially available cyclopentenone VI' and ω-side chain unit IX' very likely contain trace amount of enantiomers and as a result, in the reaction of Scheme B, the 15β-isomer of latanoprost would be produced. Moreover, commercially available cyclopentenone VI' could contain a trace amount of 5,6-trans isomer and as a result, in the reaction of Scheme B, the 5,6-trans isomer of the latanoprost would be produced.

WO2011008756 discloses the synthesis of Travoprost by a ring-closing reaction with the cyclopentane ring at the presence of a Grubb's catalyst, and conducting deprotection and ring-opening reactions to obtain Travoprost. Although WO2011008756 mentions that the ring-closing reaction would obtain an olefin with a configuration of "cis" at C5~C6, upon a study made by the inventor, the ring-closing reaction of WO2011008756 is still involved the generation of a certain amount of 5,6-trans isomer.

Latanoprost, Isopropyl unoprostone, Travoprost and Tafluprost all are not solids, and their free acid forms are not solids, either. Even in all the processes shown in Schemes A to C, none of the intermediates with the necessary chiro centers and olefins being established could be crystallized. Consequently, it is unlikely to purify these Prostaglandin analogues or intermediates by crystallization to remove the isomers. Therefore, it was almost impossible to obtain any isomer free Prostaglandin ester analogues of Formula I-2 in an oil form through common purification technology.

While WO02096898 and WO2011005505 disclose methods for removing the 5,6-trans isomer and 15-isomer of latanoprost by preparative HPLC and WO201109599 discloses removing the isomer of latanoprost acid by reverse phase preparative HPLC, these purification methods by utilization preparative HPLC to remove the isomer are costly and not suitable for mass productions.

Given the above, commercially available Prostaglandin ester analogues of Formula I-2, either as active pharmaceutical ingredients or in the form of formulation products contain a certain amount of isomers, particularly 5,6-trans isomer. For medicine safety and reducing production cost, the present invention provides a simpler process for producing isomer free Prostaglandin ester analogues of Formula I-2 where unwanted isomers, particularly 5,6-trans isomers can be effectively and easily removed during the processes.

SUMMARY OF THE INVENTION

In one aspect, the present invention provides novel processes for the preparation of a compound of Formula I-2 substantially free of the 5,6-trans isomer:

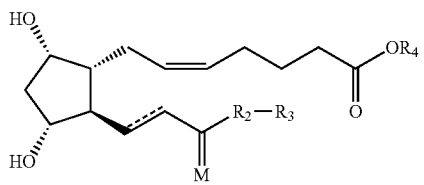

I-2 wherein

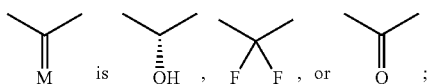

==== is a single or double bond; $R_2$ is a single bond or a $C_{1-4}$-alkylene or —$CH_2O$—; and R is a $C_{1-7}$-alkyl or an aryl or an aralkyl, each of which is unsubstituted or substituted by a $C_{1-4}$-alkyl, a halogen or a trihalomethyl; and $R_4$ is $C_{1-7}$-alkyl.

In another aspect, the present invention provides novel processes for the preparation of a compound of Formula IV substantially free of the 5,6-trans isomer:

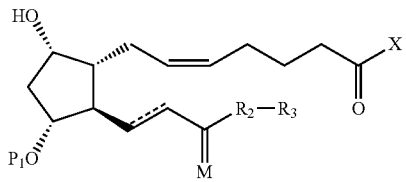

IV wherein

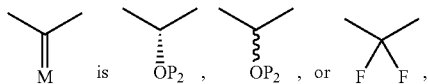

or a protective group of the carbonyl group; $P_1$ is a protective group for the hydroxyl group; ==== is a single or double bond; X is OH, $OR_4$, $NHR_5$ or $NR_4R_5$ where $R_4$ is $C_{1-7}$-alkyl and $R_5$ is H or $C_{1-7}$-alkyl; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl.

In another aspect, the present invention provides novel processes for the preparation of a compound of Formula III substantially free of the 5,6-trans isomer:

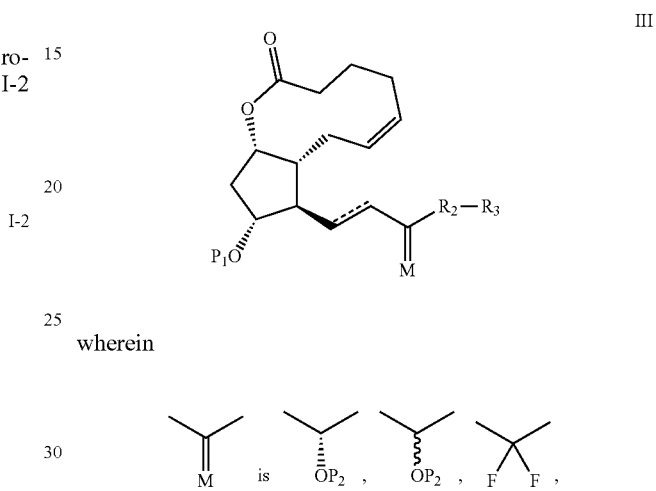

III wherein or a protective group of the carbonyl group; $P_1$ is a protective group for the hydroxyl group; ==== is a single or double bond: $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl.

In one another aspect, the present invention provides novel processes for the preparation of high purity prostaglandin or prostaglandin analogues.

In yet one another aspect, the present invention provides novel isomer free intermediates useful for the production of high purity prostaglandin or prostaglandin analogues and novel isomer free prostaglandin analogues.

DETAILED DESCRIPTION OF THE INVENTION

Preparation of Compounds of Formula IV-1

The compound of Formula IV-1

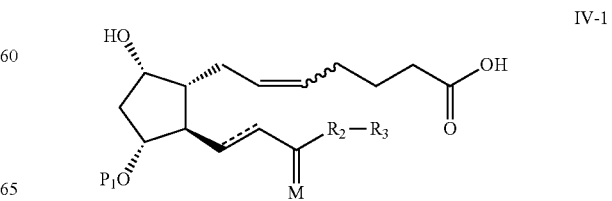

IV-1 wherein

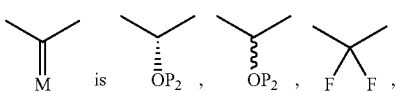

or a protective group for carbonyl group; $P_1$ and $P_2$ are protective groups for hydroxyl groups; ==== is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl, can be prepared according to the reactions shown in Scheme 1:

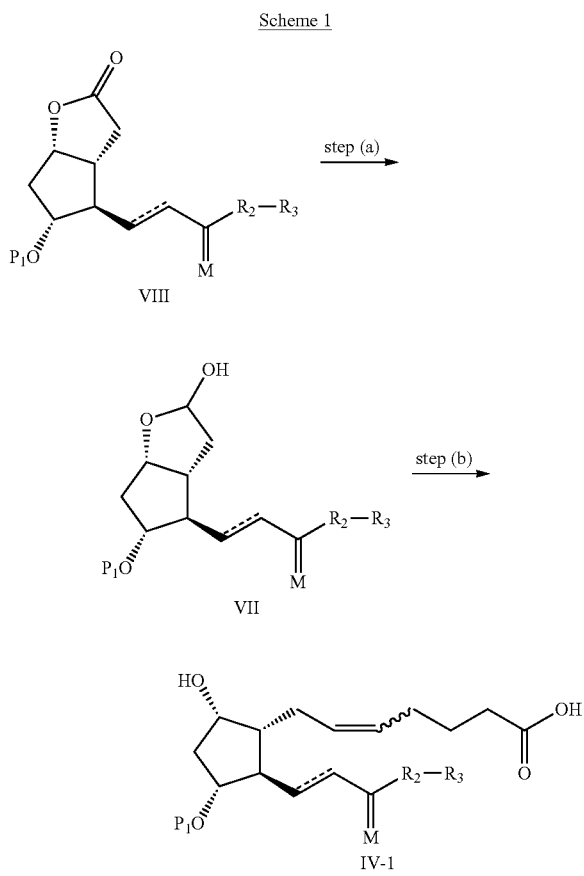

As shown in step (a) and step (b) of Scheme 1, the Lactone of Formula VIII, wherein

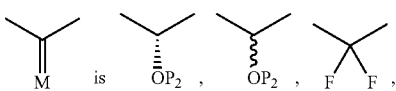

or a protective group for carbonyl group; $P_1$ and $P_2$ are protective groups for hydroxyl groups; ==== is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl, is subjected to a semi-reductive reaction with a suitable reducing agent, such as diisobutyl aluminium hydride (DIBAL), followed by a Wittig reaction to produce a compound of Formula IV-1. Owing to the use of different solvents, reagents, temperatures, and the like, the resultant cis-selectivity on the C5-C6 double bond of the compound of Formula IV-1 would depend on the solvents, reagents, temperatures, and/or the other reaction conditions involved in the Wittig reaction. Nevertheless, no matter what the reaction conditions were, it was inevitable that about 2-10% 5,6-trans isomer would be produced and such isomer was the main by-product of the preparation according to Scheme 1 for the compound of Formula IV-1. Moreover, the Lactone of Formula VIII wherein

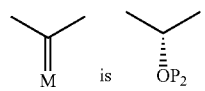

may contain a trace amount of 15β-isomer, and as a result, the 15β-isomer of the compound of Formula IV-1 prepared according to Scheme 1 would be produced. Most of the lactones of Formula VIII were produced from the popular, commercially available Corey lactones. Commercially available Corey lactones contain a trace amount of an enantiomer, and the lactones of Formula VIII prepared from such Corey lactones may contain a trace amount of an enantiomer. Consequently, when a compound of Formula IV-1 was produced according to Scheme 1, an accompanying enantiomer of the compound of Formula IV-1 would also be produced.

In Scheme 1, suitable protective group for hydroxyl groups, i.e., for $P_1$ and $P_2$, include, but are not limited to, methoxymethyl, methoxythiomethyl, tert-butylthiomethyl, benzyloxymethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl and substituted benzyl. Preferably, the protective group is methoxymethyl, methoxythiomethyl, tert-butylthiomethyl, benzyloxymethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, or triphenylmethyl.

In Scheme 1, the suitable protective groups for carbonyl groups

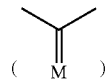

include, but are not limited to, dialkyl ketal, diaralkyl ketal, diacetyl ketal, dithio ketal, 1,3-dioxane, 1,3-dioxolane, 1,3-dithiane, 1,3-dithiolane, and 1,3-oxathiolane. Preferred protective groups for carbonyl groups include dialkyl ketal, 1,3-dioxane, and 1,3-dioxolane.

As an alternative, the compound of Formula IV-1 can be prepared according to the reactions shown in Scheme 2:

Scheme 2

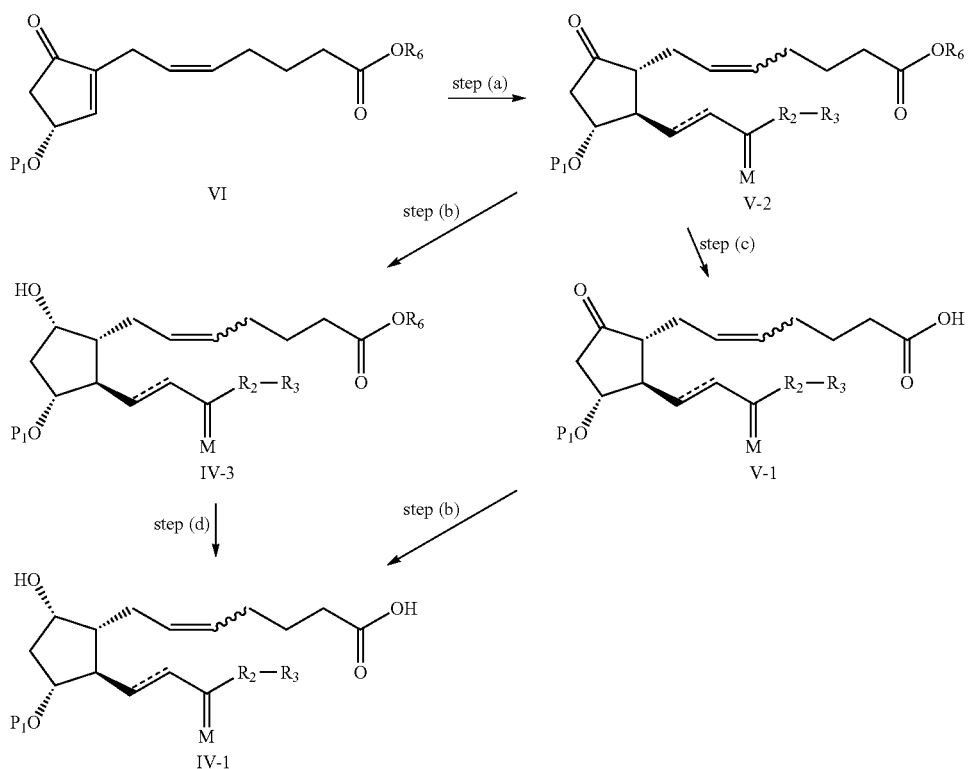

As shown in step (a) of Scheme 2, the compounds of Formula V-2, wherein

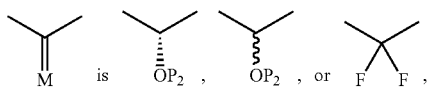

or a protective group for carbonyl group; $P_1$ and $P_2$ are protective groups for hydroxyl groups; ==== is a single or double bond; $R_2$ is a single bond or a $C_{1-4}$-alkylene or —$CH_2O$—; and $R_3$ is a $C_{1-7}$-alkyl or an aryl or an aralkyl; and R is $C_{1-7}$-alkyl, each of which is unsubstituted or substituted by a $C_{1-4}$-alkyl, a halogen or a trihalomethyl, are prepared by a coupling reaction, which is preferably performed at a temperature ranging from −100° C. to 40° C., with an enantiomerically enriched ω-side chain unit of a cuprate derived from the compound of Formula IX-1, Formula IX-2 or Formula IX-3

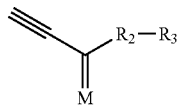   IX-1

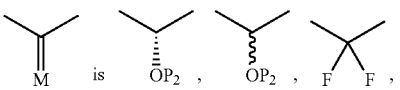   IX-2

-continued

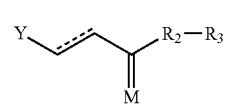   IX-3 wherein

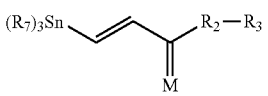

or a protective group for carbonyl group; $P_2$ is a protective group for hydroxyl group; Y is halogen; ==== is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl; $R_7$ is $C_{1-7}$-alkyl, of an optically active cyclopentenone of Formula VI wherein $R_6$ is $C_{1-7}$-alkyl; and $P_1$ is a protective group for hydroxyl group.

Step (b) of Scheme 2 pertains to a keto reduction which was performed with a reducing agent selected from sodium bis(2-methoxyethoxy)aluminum hydride, diisobutylaluminum hydride, lithium tri-tert-butoxyaluminohydride, a lithium tri-alkyl borohydride, a potassium tri-alkyl borohydride or a sodium tri-alkyl borohydride or a mixture thereof. Preferably, the reducing agent is lithium tri-sec-butylborohydride (L-selectride), lithium tri-amylborohydride, sodium tri-sec-butylborohydride, potassium tri-sec-butylborohydride, or potassium tri-amylborohydride or a mixture thereof. More preferably, the reducing agent is lithium tri-sec-butylborohydride.

Step (c) of Scheme 2 pertains to an enzymatic hydrolysis reaction which was conducted in the presence of an enzyme, preferably a *Candida antarctica* lipase, such as Lipase 435, in an aqueous phase (water or a buffer), and/or an organic solvent such as hexane, toluene, tetrahydrofuran, or methylisobutylketone, or a mixture thereof.

Step (d) of Scheme 2 pertains to an enzymatic or chemical hydrolysis reaction, preferably a chemical hydrolysis reaction. For example, a compound of Formula IV-3 was dissolved in an alcohol, such as methanol or ethanol, and reacted with a base, such as potassium hydroxide or lithium hydroxide to produce a compound of Formula IV-1.

The compounds of Formula IV-1 produced according to Scheme 2 would be accompanied not only with the by-products (8-isomer and 12-isomer) of the conjugate addition reaction of step (a), but the by-product (9-isomer) of the 9-keto reduction reaction of step (b), and even the resultant isomers (5,6-trans isomer and 15β-isomer) produced from the impurities in the starting material.

In Scheme 2, suitable protective groups for hydroxyl groups (i.e., $P_1$ and $P_2$) include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl and $SiR_aR_bR_c$ wherein $R_a$, $R_b$ and $R_c$ are each independently a $C_{1-8}$ alkyl, phenyl, benzyl, a substituted phenyl, or a substituted benzyl. Preferably, the protective group is trimethylsilyl, triethylsilyl, tert-butyldimethylsilyl, n-octyldimethylsilyl, methoxymethyl, tetrahydrofuranyl, or tetrahydropyranyl.

In Scheme 2, suitable protective groups for carbonyl group

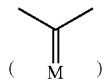

include, but are not limited to, dialkyl ketal, diaralkyl ketal, diacetyl ketal, dithio ketal, 1,3-dioxane, 1,3-dioxolane, 1,3-dithiane, 1,3-dithiolane, and 1,3-oxathiolane. Preferred protective groups for carbonyl groups include dialkyl ketal, 1,3-dioxane, and 1,3-dioxolane.

Synthesis of Prostaglandin Analogues of Formula I-2 Substantially Free of the 5,6-Trans Isomer When used herein, the term "substantially free of the 5,6-trans isomer" or "substantially isomers free" means that a compound in question does not contain more than 0.5% of 5,6-trans isomer or does not contain more than 0.5% of 5,6-trans isomer and, if present, the 15β-isomer.

According to the present invention, a novel approach for the synthesis of a prostaglandin analogue of Formula I-2 substantially free of the 5,6-trans isomer:

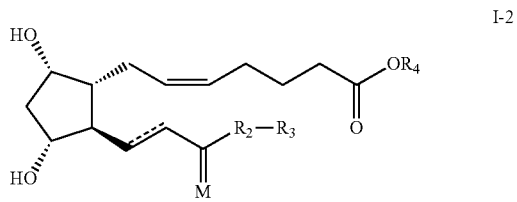

wherein

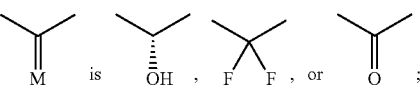

═══ is a single or double bond; $R_2$ is a single bond or a $C_{1-4}$-alkylene or —$CH_2O$—; $R_3$ is a $C_{1-7}$-alkyl or an aryl or an aralkyl, each of which is unsubstituted or substituted by a $C_{1-4}$-alkyl, a halogen or a trihalomethyl; and $R_4$ is $C_{1-7}$-alkyl, is depicted in Scheme 3.

Scheme 3

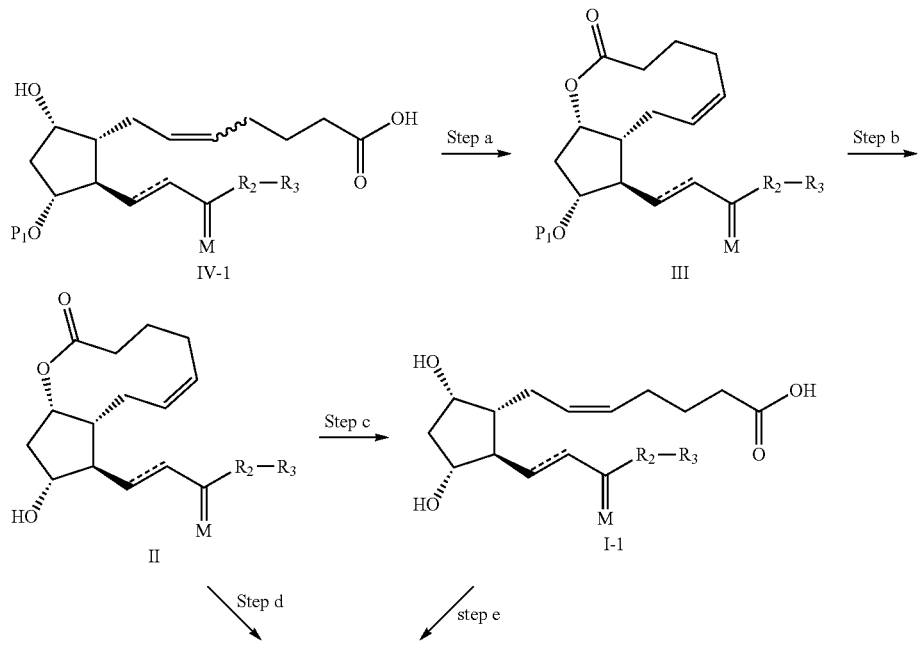

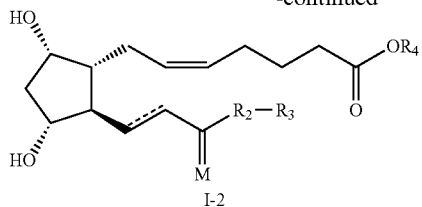

I-2

As shown in Step (a) of Scheme 3, a compound of Formula III wherein

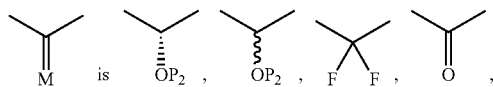

or a protective group for carbonyl group; $P_1$ and $P_2$ are protective groups for hydroxyl groups; and ====, $R_2$ and $R_3$ are as defined above for Formula I-2, is prepared by the macrolactonization of a compound of Formula IV-1 wherein

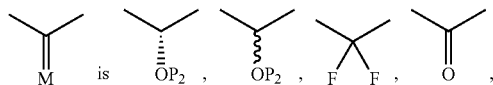

or a protective group for carbonyl group; $P_1$ and $P_2$ are protective groups for hydroxyl groups; and ====, $R_2$ and $R_3$ are as defined above, which contains 0~5% 5,6-trans isomer or/and other isomers, and can be prepared from the method of Scheme 1 or Scheme 2.

The macrolactonization may involve the activation of the carboxyl or/and hydroxyl functional groups. In this route, the macrolactonization comprises the initial formation of a thioester with a suitable reagent, which includes, but is not limited to, S-pyridin-2-yl chloromethanethioate, 2,2'-dipyridyl disulfide/triphenylphosphine, or 4-tert-butyl-2-(2-(4-tert-butyl-1-isopropyl-1H-imidazol-2-yl)disulfanyl)-1-isopropyl-1H-imidazole/triphenylphosphine. Optionally, a catalytic amount of an amine, such as triethylamine, can be added to the reaction, and in addition, a metal ion, such as $Ag^+$, $Hg^{2+}$, or $Cu^{2+}$, can also be added to promote the cyclization rate. Suitable sources for providing the metal ion include $AgClO_4$, $AgBF_4$, AgOTf, $CuBr_2$, $CuCl_2$, and $(CF_3CO_2)_2Hg$.

The macrolactonization may alternatively involve the initial formation of a mixed anhydride with a suitable reagent in the presence or absence of a base or a Lewis acid. Suitable reagents for forming the mixed anhydrides include, but are not limited to, 2,4,6-trichlorobenzoyl chloride, 2-nitro-6-nitrobenzoic anhydride, p-nitrofluoromethylbenzoic anhydride, p-nitrobenzoic anhydride and the like. Examples of the suitable bases include 4-(dimethylamino)pyridine, pyrolidinopyridine, triethylamine, N,N-diisopropylethylamine, and isopropyldiethylamine. Examples of suitable Lewis acids include $Sc(OTf)_3$, $TiCl_4$, $AgClO_4$, trimethylsilyl chloride (TMSCl) and $TiCl_2(OTf)$.

The macrolactonization can also be achieved by using a condensation reagent and a base in an appropriate solvent. Suitable condensation reagents include, but are not limited to, N,N'-dicyclohexylcarbodiimide, 2-chloro-1-methyl-pyridium iodide, 2-chloro-4,5-dihydro-1,3-dimethyl-1H-imidazolium chloride, N,N-diphenylchlorophenylmethyl-eniminium chloride, cyanuric chloride, 1,3-dimethyl-2-chloroimidazolium chloride and N,N,N,N-tetramethylchloroformamidinium chloride, and the like. Examples of suitable bases include pyridine, triethylamine, diisopropylethylamine, 4-dimethylaminopyridine (DMAP), and the like. Suitable solvents for the condensation reaction include methylene chloride, tetrahydrofuran, and 1,2-dichloroethane, and a mixture thereof.

Upon analyzing a resultant compound of Formula III by HPLC or UPLC, it is unexpectedly found that the resultant compound of Formula III is substantially free of the 5,6-trans isomer, which reveals that the macrolactonization reaction exhibits a high cis-selectivity, that is, the 5,6-cis compounds of Formula IV-1 dominate in the macrolactonization reaction whereas the 5,6-trans compounds of Formula IV-1 hardly undergo the macrolactonization reaction.

Step (b) of Scheme 3 involves a deprotection reaction by removing the $P_1$ or/and the $P_2$ at the ω-side chain. The conditions for carrying out such deprotection reactions are obvious to persons skilled in the art. For example, the macrolactone of Formula III when $P_1$ and, if present, $P_2$ are tetrahydropyranyl protective groups is dissolved in a suitable solvent, such as methanol or a solvent mixture of acetone and water in a volumetric ratio of 5 to 1, treated with a deprotecting agent such as hydrogen chloride, p-toluenesulfonic acid, or pyridium p-toluenesulfonate, and stirred at room temperature for 10 minutes to 10 hours. The reaction is quenched with a base, e.g., ammonium hydroxide or the like, and subjected to a work-up procedure conducted in a conventional manner. It is unexpectedly found that the resultant deprotected compound of formula II substantially free of the 5,6-trans isomer exhibits excellent crystallizability, for example, as evidenced from the working examples provided thereinafter as having a melting point higher than 100° C., compared to Compounds IIa, IIb, and IIe disclosed in WO2011008756 (Example 9, 12a-12c) each of which contains a certain amount of a5,6-trans isomer and is not in a solid form.

The crude product of the compound of Formula II contains a small amount of isomers (such as 15β-isomer, an enantiomer) derived from the impurity in the starting compound of Formula IV-1, and such isomer can be further removed by purifying the crude product via crystallization.

Step (c) in combination with Step (e), and alternatively Step (d) of Scheme 3 involve transesterification reactions of the macrolactone of Formula II to form a prostaglandin analogue of Formula I-2. In Step (d), the transesterification includes the direct reaction of a compound of Formula II with a nucleophile selected from the group consisting of a $C_{1-7}$ alkanol, a $C_{1-7}$ alkoxide, a $C_{1-7}$ alkoxide salt, or a mixture thereof to form a prostaglandin analogue of Formula I-2 containing a hydroxyl group and an ester group. According to an embodiment of the present invention, the nucleophile is selected from 2-propanol, sodium 2-propoxide, or a mixture thereof.

In Step (c) and Step (e), the transesterification includes hydrolyzing the macrolactone of Formula II to form a compound of Formula I-1 containing a hydroxyl group and a carboxyl group, and then esterificating the compound of Formula I-1 to obtain a prostaglandin analogue of Formula I-2.

According to the present invention, the resultant compound of Formula I-2 can be further purified by silylating all the hydroxyl groups in the compound of Formula I-2 with a silylating agent of formula $XSiR_aR_bR_c$ wherein X is a halogen, such as F, Cl, or Br, $R_a$, $R_b$ and $R_c$ are each independently a $C_{1-8}$ alkyl, phenyl, benzyl, a substituted phenyl, or a substituted benzyl, in a suitable solvent, such as tetrahydrofuran (THF), dimethylformamide (DMF), or ethyl acetate, and in the presence of a base such as imidazole or triethylamine to form a compound of Formula I-2",

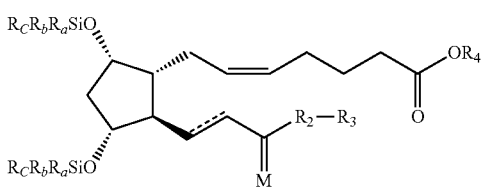

I-2"

wherein

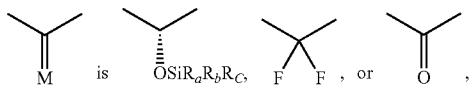

$R_a$, $R_b$ and $R_c$ are each independently a $C_{1-8}$ alkyl, benzyl, a substituted phenyl, or a substituted benzyl; and ====, $R_2$ and $R_3$ are as defined above; removing the impurities; and then desilylating the resultant compound to form a compound of Formula I-2 having an improved purity. According to an embodiment of the present invention, the silylating agent suitable for the purification reaction is selected from the group consisting of chlorotrimethylsilane, chlorotriethylsilane, chlorodimethyl(octyl)silane, and tert-butylchlorodimethylsilane. As for the conditions for carrying out the desilylation reaction, they can be those obvious to persons skilled in the art for the deprotection reaction described hereinbefore.

According to some preferred embodiments of the present invention, certain conventionally known prostaglandin analogues substantially free of isomers can be prepared in the following manners:

Synthesis of Isomers Free Travoprost

As shown in the following Scheme, isomers free Travoprost can be easily produced from commercially available compound Xa, without the need of utilizing chromatography for separating the isomers.

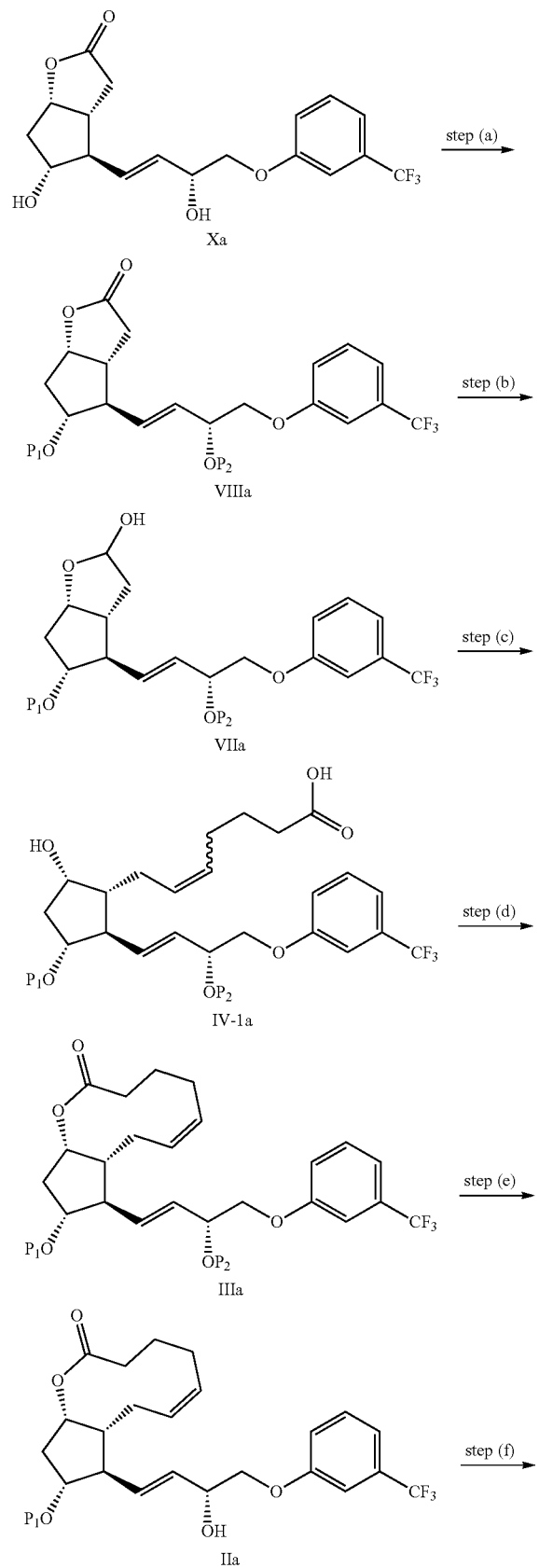

Scheme 4

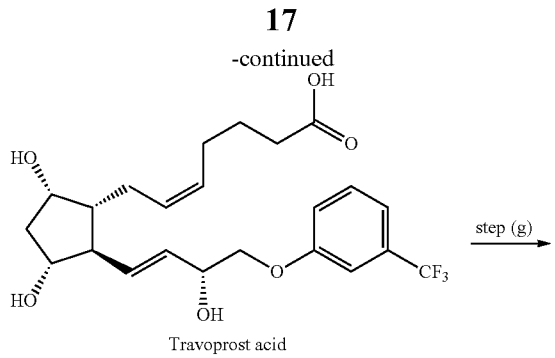

Travoprost acid

Travoprost

The reaction in step (a) of Scheme 4 is a protection reaction. Examples of suitable protective groups are described by T. W. Greene in "Protective Groups in Organic Synthesis," John Wiley & Sons, Inc., 1981. Preferred protective groups are base stable, and may include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, and benzyl and substituted benzyl. The reaction conditions for conducting the protection can be those conventionally known in the art. For example, the Lactone of Formula Xa is dissolved in methylene chloride and p-toluenesulfonic acid in a catalytic amount is added thereto. The reaction mixture is subjected to an ice bath, and an appropriate amount of 3,4-dihydro-2H-pyran is added, and then is stirred at room temperature for about 10 minutes to about 10 hours to obtain a protected Lactone of Formula VIIIa.

In Step (b) of Scheme 4, the Lactone of Formula VIIIa is subjected to a semi-reductive reaction with diisobutyl aluminium hydride (DIBAL) to obtain the Lactol of Formula VIIa. The reaction can be conducted at a temperature ranging from −60° C. to −100° C. preferably from −60° C. to −80° C.

In Step (c) of Scheme 4, the Lactol of Formula VIIa is then subjected to a Wittig reaction with the ylide generated from (4-carboxybutyl)triphenylphosphonium bromide and potassium tert-butoxide, to produce a compound of Formula IV-1a containing 2~4% 5,6-trans isomer.

Step (d) of Scheme 4 is a macrolactonization reaction. No matter whether the macrolactonization undergoes through the formation of a thioester or a mixed anhydride or condensation with 1,3-dicyclohexylcarbodiimide, the compound of IIIa can be obtained.

Upon analysis of a resultant compound of Formula IIIa by UPLC, it is found that no matter what reagents and reaction conditions were used, all the obtained compounds of Formula IIIa contain the 5,6-trans isomer in an amount less than 0.03% or even less than the amount that can be detected by UPLC.

Step (e) of Scheme 4 is a deprotection reaction. The macrolactone of Formula IIIa wherein each of $P_1$ and $P_2$ is a tetrahydropyranyl protective group is dissolved in a suitable solvent, such as methanol, treated with a deprotecting agent such as hydrogen chloride, p-toluenesulfonic acid, or pyridium p-toluenesulfonate, and stirred at room temperature for 10 minutes to 10 hours. The reaction is quenched with a base, e.g., aqueous sodium bicarbonate solution or the like, and subjected to a work-up procedure conducted in a conventional manner to obtain the compound of Formula IIa as a solid. After crystallization, the resultant crystalline compound and the filtrate of the crystallization were analyzed by UPLC. It was found that either the isomers or the impurities resulting from the reactions could be effectively removed by the crystallization process.

The compound of Formula IIa substantially free of isomers and impurities was subjected to hydrolysis reaction in step (f) of Scheme 4 to obtain isomers free Travoprost acid ((+)-fluprostenol), which was then subjected to an esterification reaction in step (g) of Scheme 4 to obtain isomers free Travoprost.

Synthesis of Isomers Free Latanoprost

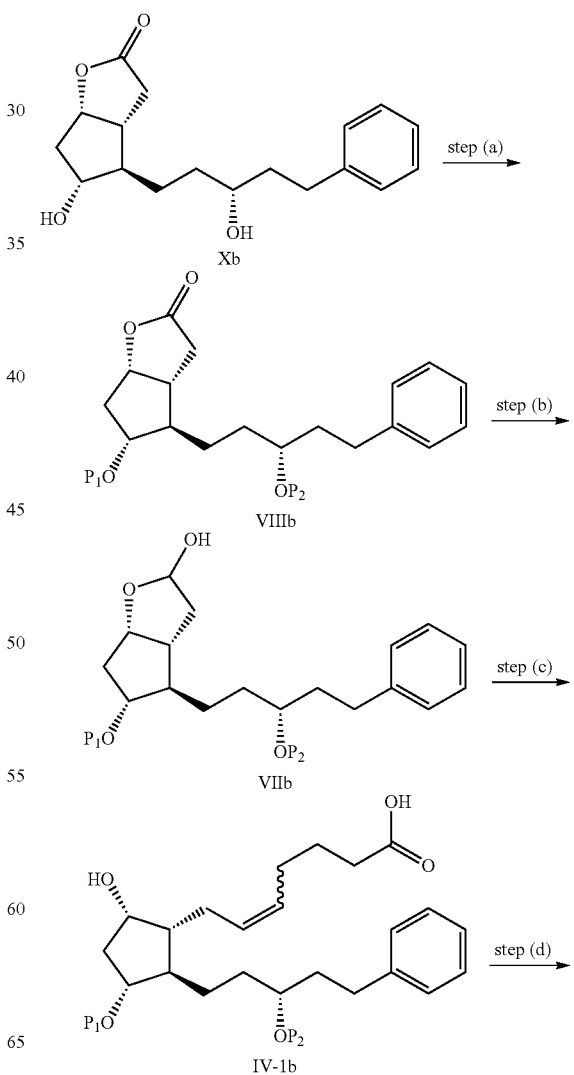

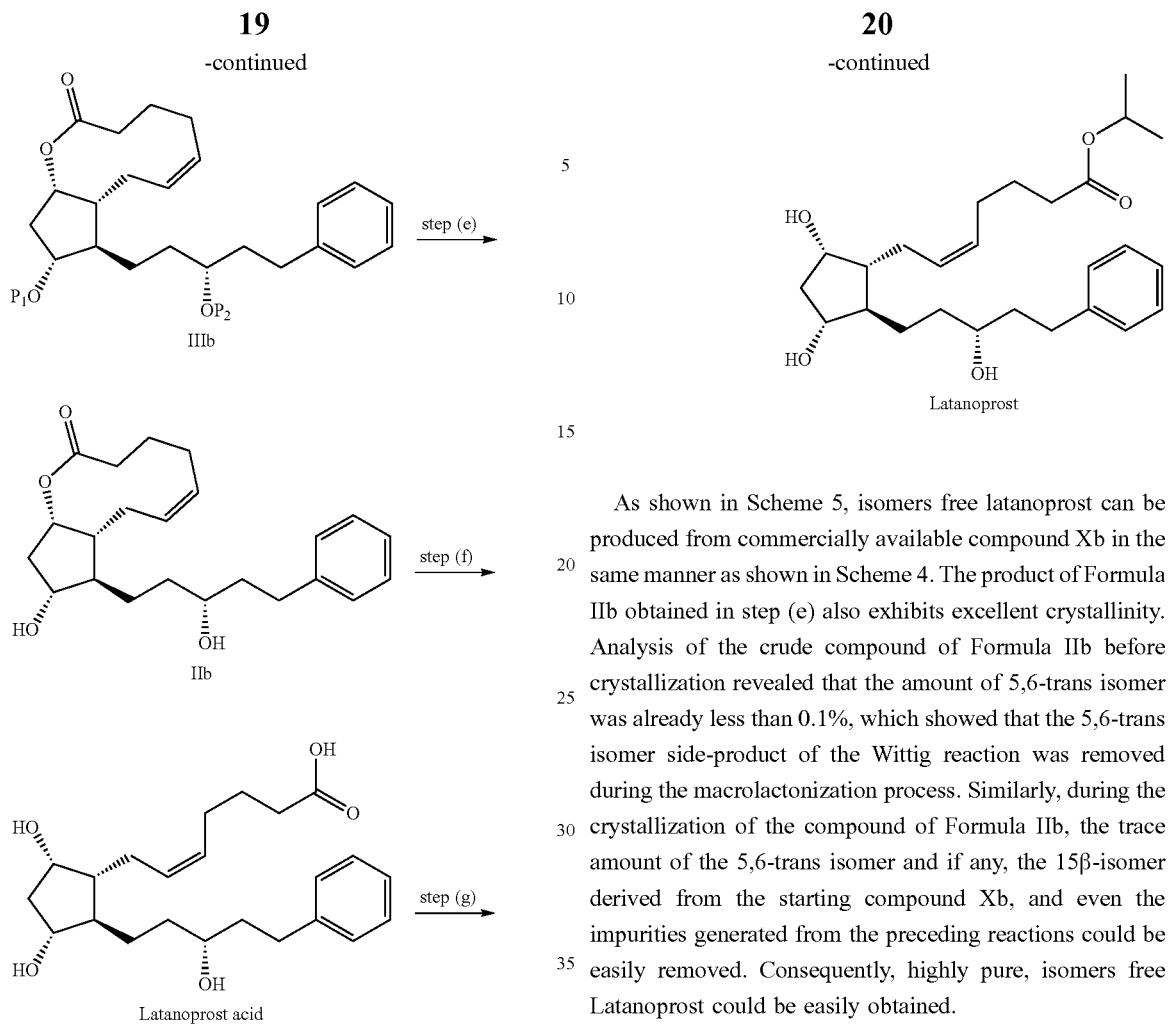

As shown in Scheme 5, isomers free latanoprost can be produced from commercially available compound Xb in the same manner as shown in Scheme 4. The product of Formula IIb obtained in step (e) also exhibits excellent crystallinity. Analysis of the crude compound of Formula IIb before crystallization revealed that the amount of 5,6-trans isomer was already less than 0.1%, which showed that the 5,6-trans isomer side-product of the Wittig reaction was removed during the macrolactonization process. Similarly, during the crystallization of the compound of Formula IIb, the trace amount of the 5,6-trans isomer and if any, the 15β-isomer derived from the starting compound Xb, and even the impurities generated from the preceding reactions could be easily removed. Consequently, highly pure, isomers free Latanoprost could be easily obtained.

Synthesis of Pure Tafluprost

Scheme 6

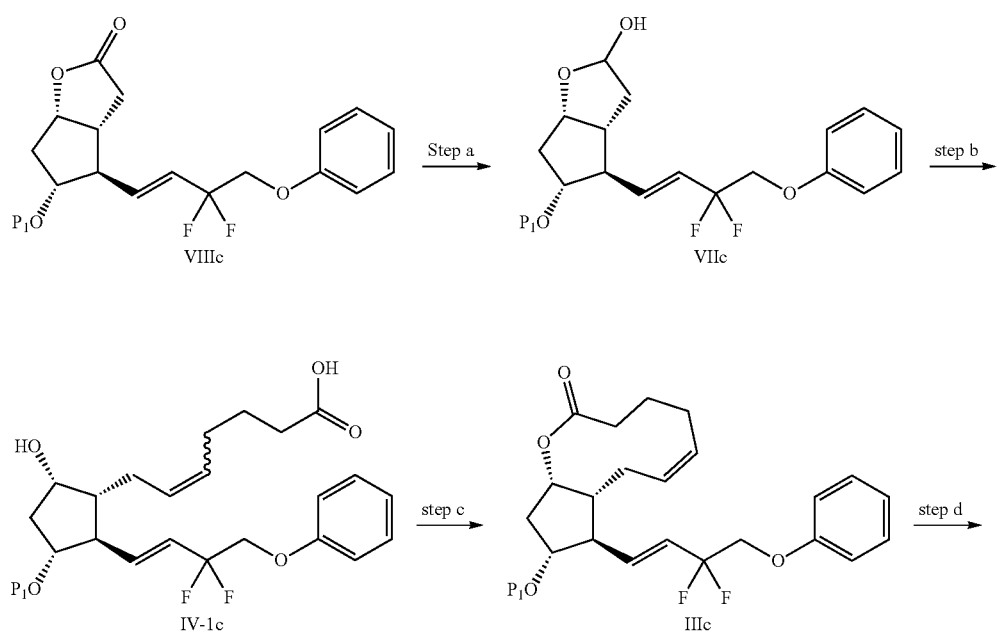

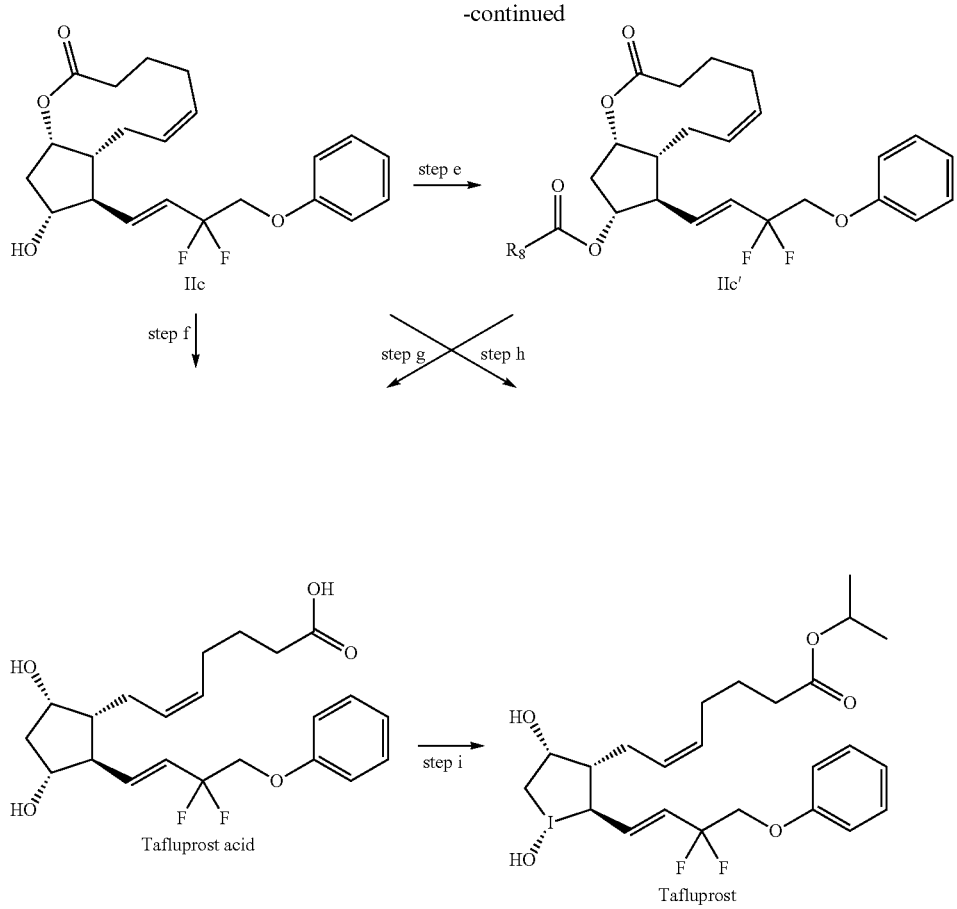

As shown in Scheme 6, similar to the reactions shown in Schemes 4 and 5, step (a) is a DIBAL reduction reaction, step (b) is a Wittig reaction, step (c) is a microlactonization reaction, and step (d) is a deprotection reaction. The compound of Formula IIc obtained in step (d) is substantially free of the 5,6-trans isomer. It was subjected to the hydrolysis reaction of step (f) and the esterification reaction of step (i) to obtain Tafluprost substantially free of the 5,6-trans isomer. As an alternative, the compound of Formula IIc could be acylated with an acylating agent of Formula $R_8COCl$ or $(R_8CO)_2O$ wherein $R_8$ is $C_{1-7}$-alkyl, unsubstituted phenyl or substituted phenyl such as acetyl chloride, acetic anhydride, benzoyl chloride, benzoic anhydride, or 4-phenyl benzoyl chloride, into the compound of Formula IIc' wherein $R_8$ is $C_{1-7}$-alkyl, unsubstituted phenyl or substituted phenyl which has better crystallinity and the compound of Formula IIc' could be purified by crystallization so as to remove the trace amount of the isomer, and if present, even the enantiomer to obtain isomer free Tafluprost. Step (g) is a hydrolysis reaction which simultaneously opens the macrolactone ring and deacylates the compound to form isomer free Tafluprost acid. In Step (h), the transesterification includes the direct reaction of a compound of Formula IIc with a nucleophile selected from 2-propanol, sodium 2-propoxide, or a mixture thereof to form Tafluprost.

Synthesis of Pure Isopropyl Unoprostone

Scheme 7

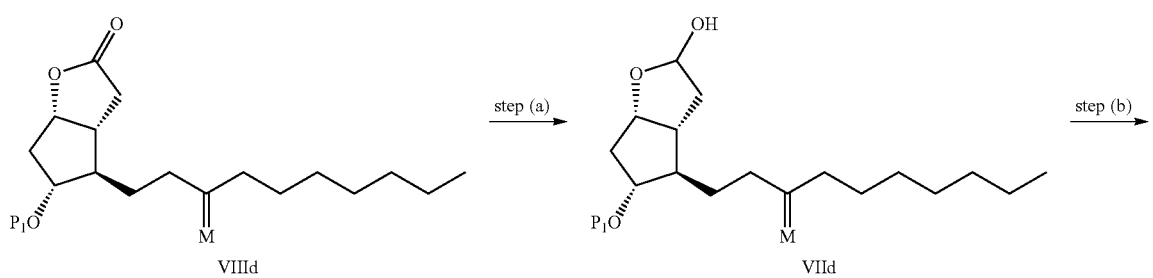

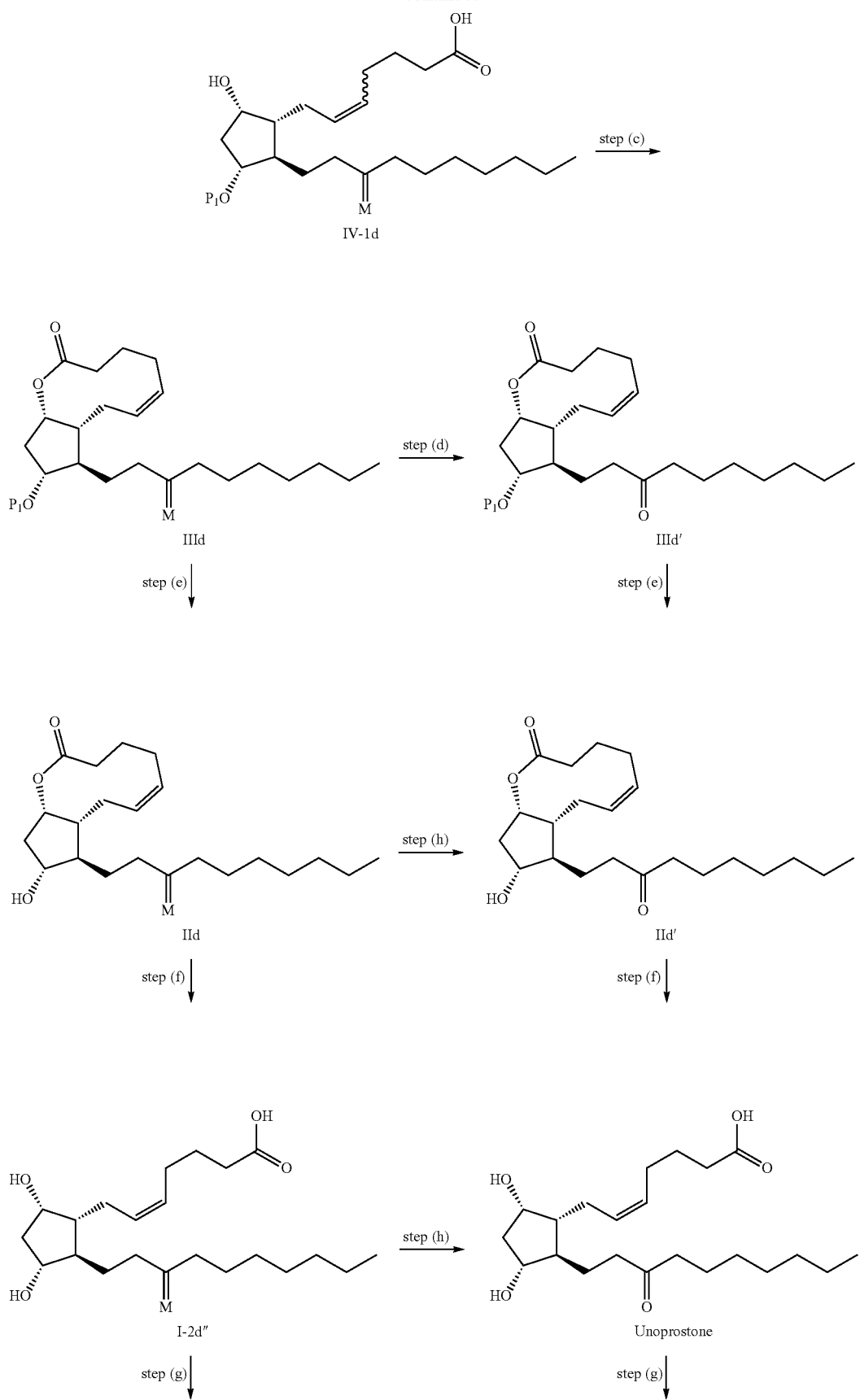

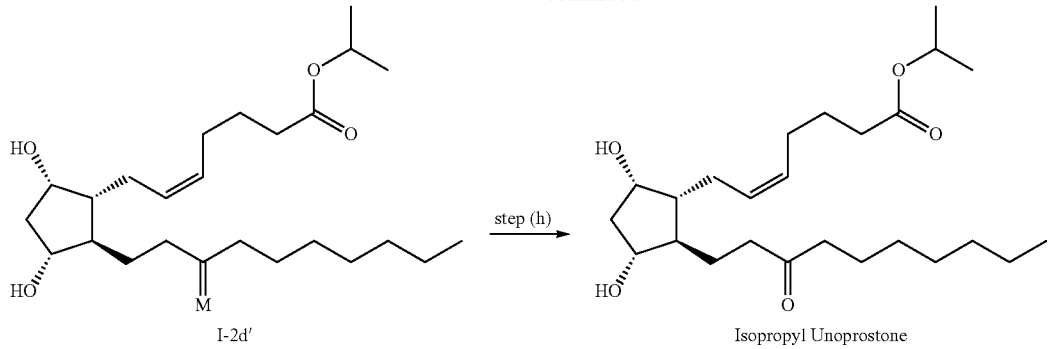

I-2d'  →  Isopropyl Unoprostone step (h)

As shown in Scheme 7, similarly, step (a) is a DIBAL reduction reaction, step (b) is a Wittig reaction, step (c) is a microlactonization reaction, step (e) is a deprotection reaction, step (f) is a hydrolysis reaction, and step (g) is an esterification reaction. For the synthesis of Isopropyl Unoprostone, the starting compound of Formula VIIId, wherein

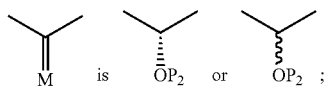

$P_1$ and $P_2$ are protective groups for the hydroxyl groups, was subjected to step (a)~step (c) to form the macrolactone of Formula IIId. Thereafter, the macrolactone of Formula IIId was preferably subjected to step (d) for selectively removing $P_2$ and oxidizing the resultant hydroxy group into a keto group. For example, the macrolactone of Formula IIId, wherein

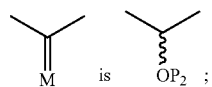

$P_1$ is tetrahydropyranyl; and $P_2$ is tert-butyldimethylsilyl, was reacted in a suitable solvent, such as THF, with tetra-n-butylammonium fluoride (TBAF), so as to selectively remove tert-butyldimethylsilyl; and then oxidized at proper oxidation conditions, such as Collins oxidation, Swern oxidation, PCC oxidation, PDC oxidation, or TEMPO oxidation, preferably TEMPO oxidation, to form a compound of Formula IIId' substantially free of the 5,6-trans isomer.

The compound of Formula IIId' was then subjected to the deprotection reaction in step (e) to remove $P_1$ so as to form the novel crystalline compound of Formula IId', followed by the ring-opening hydrolysis reaction in step (f) to obtain isomer free Unoprostone, which was further subjected to the esterification reaction of step (g) to obtain isomer free isopropyl Unoprostone.

As mentioned above, the macrolactone of Formula IIId could be subjected to step (d) for removing the protection group for carbonyl to form a compound of Formula IIId'. Alternatively, the macrolactone of Formula IIId could be first subjected to step (e) for removing the protection group $P_1$, followed by the ring-opening hydrolysis reaction of step (f) and the esterification reaction of step (g), and then subjected to step (h) to remove the protection group for carbonyl, so as also to obtain isopropyl Unoprostone. Alternatively, compound of Formula IId and I-2d" subjected to step (h) to remove the protection group for carbonyl to obtain compound of Formula IId' and Unoprostone Synthesis of Prostaglandin Analogues of Formula IV According to the present invention, a novel approach for the synthesis of a prostaglandin analogue of Formula IV substantially free of the 5,6-trans isomer:

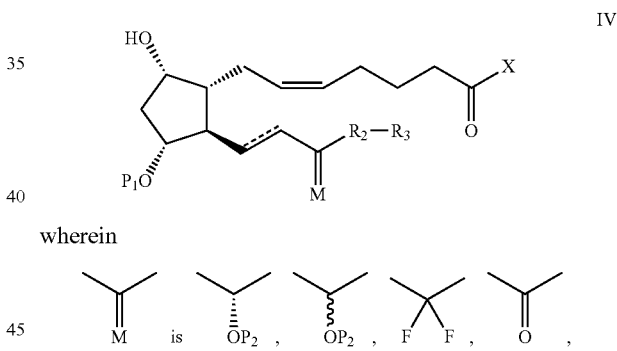

wherein

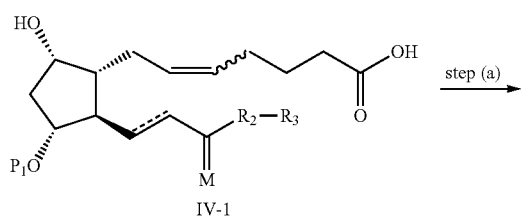

or a protective group for carbonyl group; $P_1$ and $P_2$ are protective groups for hydroxyl groups; ==== is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl; X is OH, $OR_6$, or $NR_4R_5$ wherein $R_4$ and $R_6$ are $C_{1-7}$-alkyl, and $R_5$ is H or $C_{1-7}$-alkyl is depicted in Scheme 8:

Scheme 8

[Structure IV-1 with step (a) arrow]

IV-1

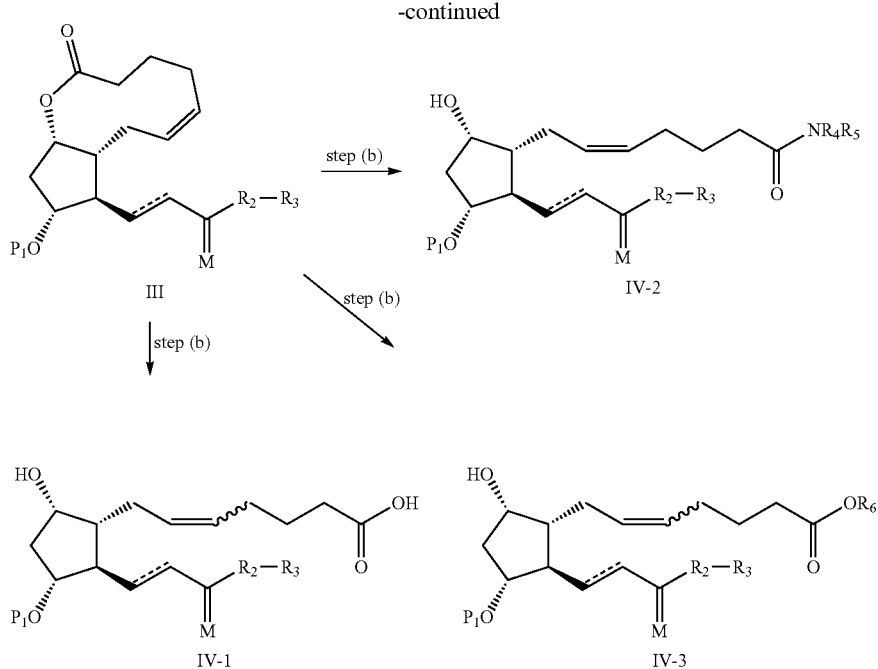

Step (a) illustrated in Scheme 8 is macrolactonization reaction of the compound of Formula IV-1 which contains 1~10% 5,6-trans isomer and step (b) is related to an amidation reaction. The macrolactone of Formula III is reacted with an alkyl amine of Formula $HNR_4R_5$ where $R_4$ is $C_{1-7}$-alkyl and $R_5$ is H or $C_{1-7}$-alkyl, such as, but not limited to, ethylamine, in an aprotic solvent, such as, but not limited to, tetrahydrofuran, to form a compound of Formula IV-2, wherein X is $NR_4R_5$, substantially free of the 5,6-trans isomer. Step (b) is also related to a transesterification reaction. The macrolactone of Formula III is reacted with a nucleophile selected from the group consisting of a $C_{1-7}$ alkanol, a $C_{1-7}$ alkoxide, a $C_{1-7}$ alkoxide salt, or a mixture thereof to form a compound of Formula IV-3 wherein X is $OR_6$ substantially free of the 5,6-trans isomer. Step (b) is also related to a hydrolysis reaction. The macrolactone of Formula III is hydrolyzed to form a compound of Formula IV-1 wherein X is OH, substantially free of the 5,6-trans isomer Synthesis of Bimatoprost According to the present invention, isomers free Bimatoprost can be synthesized as shown in Scheme 9:

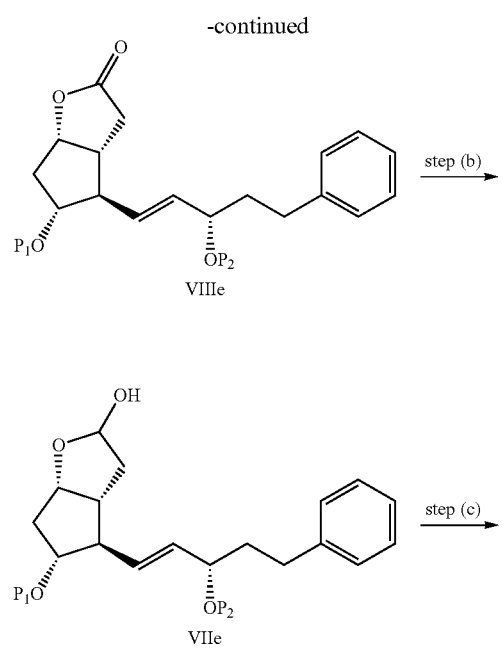

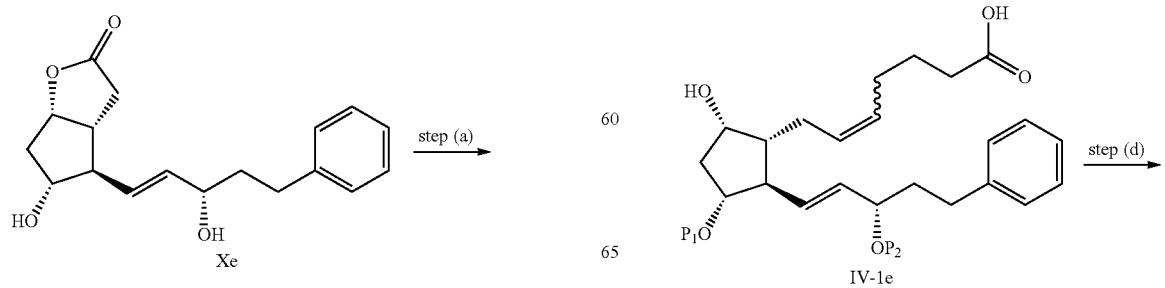

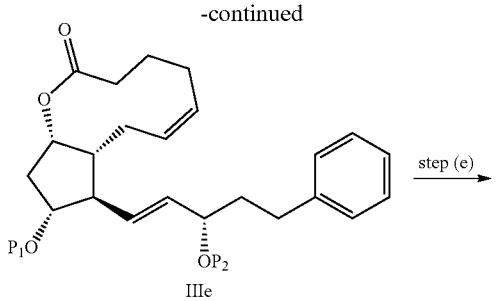

IIIe

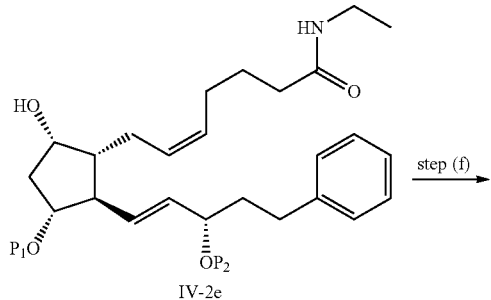

IV-2e

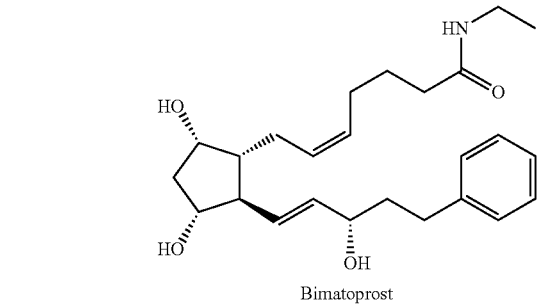

Bimatoprost

As shown in Scheme 9, isomers free Bimatoprost can be easily produced from commercially available compound Xe. Commercially available compound Xe is subjected to a protection reaction in step (a), reduction with DIBAL in step (b), Wittig reaction in step (c), and macrolactonization reaction in step (d) to obtain a protected macrolactone of Formula IIIe substantially free of the 5,6-trans isomer. Step (e) of Scheme 9 represents an amidation reaction of the protected macrolactone of Formula IIIe to form a protected Bimatoprost in a high yield, and then the protected Bimatoprost is subjected to the deprotection reaction of step (f) to obtain crude Bimatoprost substantially free of the 5,6-trans isomer. Isomers free Bimatoprost can be obtained by one-time crystallization of the crude Bimatoprost. As compared to the prior art processes where Wittig reaction product of Formula IV-1e containing 2~3% 5,6-trans isomer was subjected to esterification and amidation to obtain crude Bimatoprost which still contained 2~3% 5,6-trans isomer and requires recrystallization many times to obtain isomers free Bimatoprost in a significantly lower yield, the process according to the present invention includes a macrolactonization reaction in step (d) to allow the removal of the 5,6-trans isomer produced in the Wittig reaction and the resultant Bimatoprost upon further purification-by-crystallization can be obtained in a higher yield.

Synthesis of Compounds of Formula III

According to another aspect of the present invention, a process for the synthesis of compounds of Formula III substantially free of the 5,6-trans isomer

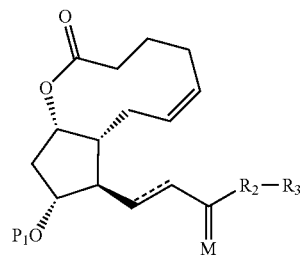

is provided, wherein

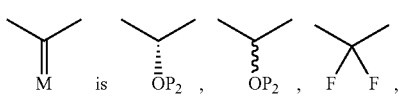

or a protecting group for carbonyl group; $P_1$ and $P_2$ are protecting groups for the hydroxyl groups; ==== is a single or double bond; $R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl, by macrolactonizing a compound of Formula IV-1 obtained either from Scheme 1 or from Scheme 2. The macrolactonization can be conducted in a same manner as described hereinbefore.

Novel Compounds of Formula III

The present invention also provides novel compounds selected from the group consisting of:

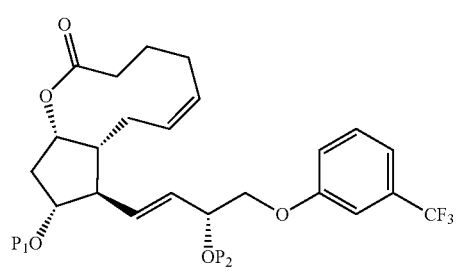

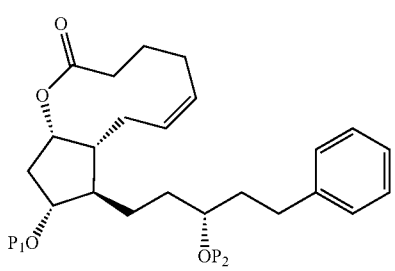

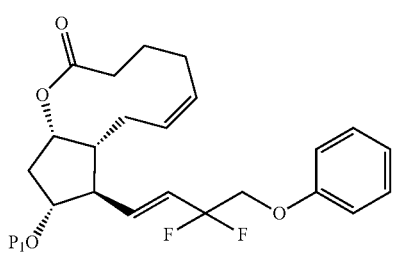

IIId

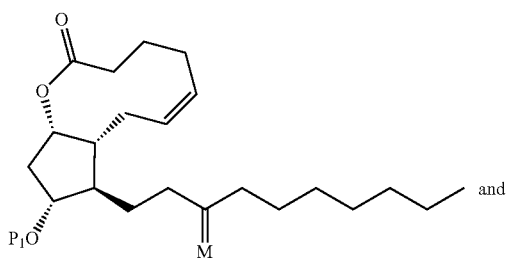 and

IIIe

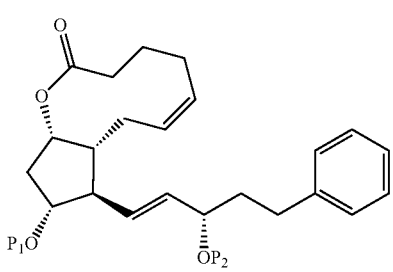

wherein

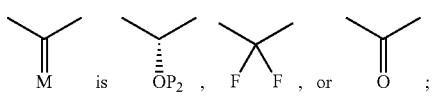

and $P_1$ and $P_2$ are protecting groups for the hydroxyl groups, which are independently selected from the group consisting of methoxymethyl, methoxythiomethyl, tert-butylthiomethyl, benzyloxymethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl.

Novel Isomer Free Compounds of Formula II

Given the above, the invention further provides crystalline compounds substantially free of the 5,6-trans isomer and 15β-isomer selected from the group consisting of compound IIa, IIb, IIc, IId, and IIe:

IIa

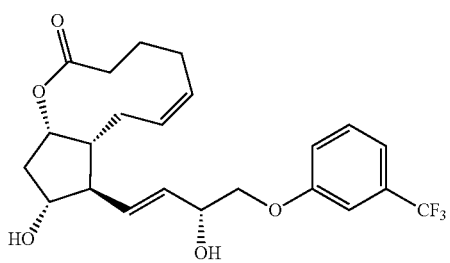

IIb

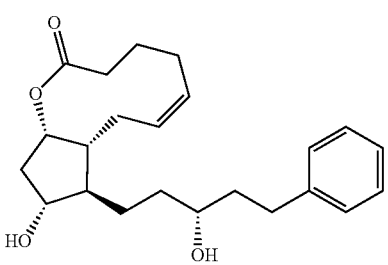

IIc

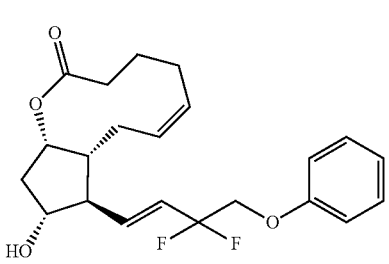

IId

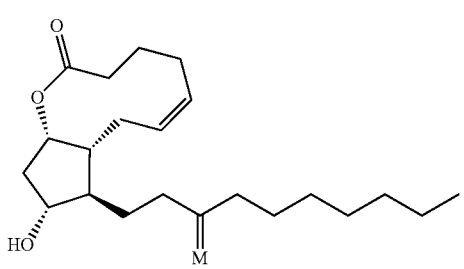

IIe

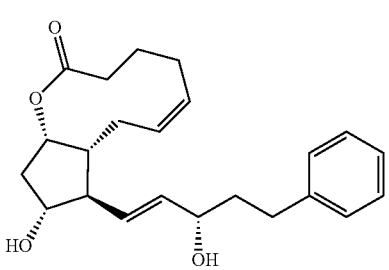

wherein

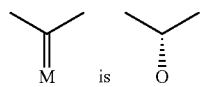

or a protecting group of the carbonyl group. For the compounds of Formula IId, the invention provides in particular the compound of Formula IId':

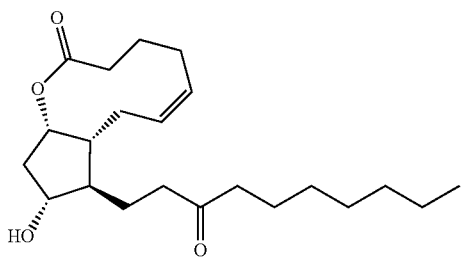

IId'

Novel Compounds of Formula IIc'

The invention further provides crystalline compound of Formula IIc' substantially free of the 5,6-trans isomer and 15β-isomer

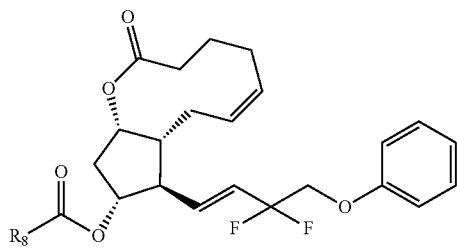

IIc' wherein $R_8$ is $C_{1-7}$-alkyl, unsubstituted phenyl or substituted phenyl.

Novel Isomers Free Compounds of Formula I-1

According to yet another aspect of the present invention, a compound substantially free of the 5,6-trans isomer selected from the group consisting of travoprost free acid, latanoprost free acid, bimatoprost free acid, tafluprost free acid, fluprostenol, cloprostenol, and unoprostone. Preferably, the compound substantially free of the 5,6-trans isomer contains less than 0.1% of the 5,6-trans isomer.

Novel Isomer Free Prostaglandin Analogues of Formula I-2

As mentioned above, the processes according to the present invention are useful in the production of isomers free prostaglandin analogues. Therefore, the present invention further provides an isomer free prostaglandin analogue selected from the group consisting of Latanoprost containing less than 0.2% isomers, Travoprost containing less than less than 0.5% isomers and less then 0.1% for each single isomer, Tafluprost containing less than 0.5% isomers and less than 0.1% for each single isomer, and Unoprostone Isopropyl ester containing less than 0.5% isomers and less than 0.1% for each single isomer, among which, preferably, Latanoprost contains less than 0.1% isomers; Travoprost contains less than 0.2% isomers, Tafluprost contains less than 0.2% isomers, and Unoprostone Isopropyl ester contains less than 0.2% isomers. More preferably, Latanoprost contains less than 0.1% isomers; Travoprost contains less than 0.1% isomers, Tafluprost contains less than 0.1% isomers, and Unoprostone Isopropyl ester contains less than 0.1% isomers.

The following examples are provided to further illustrate the present invention but are not intended to limit the scope thereof. Any modifications or changes without departing from the spirits of the invention and obvious to a person of ordinary skill in the art fall within the scope of the disclosure in the specification and the appended claims.

Examples 1~12 Preparation of Travoprost and its Intermediates Via Wittig Reaction Example 1

(3aR,4R,5R,6aS)-5-((tetrahydro-2H-pyran-2-yl)oxy)-4-((3R,E)-3-((tetrahydro-2H-pyran-2-yl)oxy)-4-(3-(trifluoromethyl)phenoxy)but-1-en-1-yl)hexahydro-2H-cyclopenta[b]furan-2-one

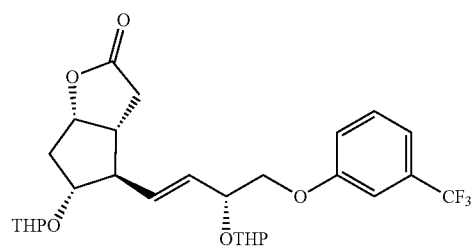

p-Toluenesulfonic acid monohydrate (0.35 g, 1.8 mmol) was added to a solution of (3aR,4R,5R,6aS)-4-((R,E)-4-(3-(trifluoromethyl)phenoxy)-3-hydroxybut-1-enyl)-hexahydro-5-hydroxycyclopenta[b]furan-2-one (15.0 g, 40.3 mmol) and 3,4-dihydro-2H-pyran (8.47 g, 100.7 mmol) in THF (200 mL) at room temperature and the mixture was stirred for 2.5 hr (TLC monitoring). Saturated aqueous solution of sodium bicarbonate (200 mL) was poured into the reaction mixture and the mixture was stirred for 5 minutes. The organic layer was separated and the aqueous layer was extracted with ethyl acetate (200 mL). The combined organic layers were dried over magnesium sulfate, filtered off solid and concentrated under reduced pressure to give 24.0 g of crude product. The crude product was purified by column chromatography and then concentrated under reduced pressure to provide 19.0 g of the titled compound (87.5% yield).

$^1$H-NMR (400 MHz, CDCl$_3$): δ 7.390 (t, 1H), 7.196 (d, 1H), 7.129 (s, 1H), 7.029-7.097 (m, 1H), 5.484-5.727 (m, 2H), 4.923-5.002 (m, 1H), 4.645-4.709 (m, 2H), 4.443-4.490 (m, 1H), 3.772-4.160 (m, 5H), 3.448-3.529 (m, 2H), 2.362-2.805 (m, 4H), 2.078-2.202 (m, 2H), 1.452-1.790 (m, 12H).

13C-NMR (100 MHz, CDCl$_3$): δ 177.175 (176.977, 176.605), 158.890, 134.874, 134.676 (132.384), 131.770 (q), 130.008 (129.948), 129.196 (129.006), 128.422, 123.917 (q), 118.251 (118.167), 117.609 (q), 111.393 (q), 98.713 (98.448, 98.394), 95.874 (95.844, 94.964), 83.707

(83.434, 83.123, 82.857), 79.616 (79.373), 74.606 (74.553, 73.680, 73.642), 70.796 (70.705, 70.644), 62.371 (61.718), 54.735 (54.196), 42.355 (42.029, 41.960), 35.903 (35.842), 35.341 (35.068, 34.772, 34.499), 30.582 (30.560, 30.476), 30.377, 25.390 (25.375), 19.349 (19.288, 19.273, 19.220), 18.939 (18.908).

Example 2

(3aR,4R,5R,6aS)-5-((tetrahydro-2H-pyran-2-yl)oxy)-4-((3R,E)-3-((tetrahydro-2H-pyran-2-yl)oxy)-4-(3-(trifluoromethyl)phenoxy)but-1-en-1-yl)hexahydro-2H-cyclopenta[b]furan-2-ol

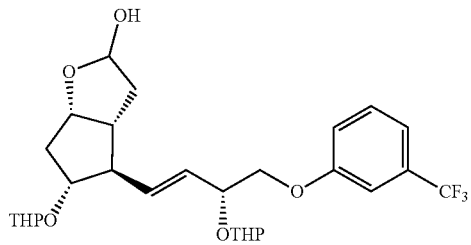

(3aR,4R,5R,6aS)-5-((tetrahydro-2H-pyran-2-yl)oxy)-4-((3R,E)-3-((tetrahydro-2H-pyran-2-yl)oxy)-4-(3-(trifluoromethyl)phenoxy)but-1-en-1-yl)hexahydro-2H-cyclopenta[b]furan-2-one (19.0 g, 35.3 mmol) was dissolved in toluene (200 mL), followed by cooling to −70° C., and DIBAL (1.0M in hexane, 53 mL, 53 mmol) was added dropwisely. Then the reaction was quenched by adding saturated aqueous solution of ammonium chloride (10 mL) at −70° C. The resulting mixture was poured into a 2M sodium bisulfate aqueous solution (200 mL) at room temperature and stirring was continued for 30 minutes. After separation of the organic layers, toluene (200 mL) was added to the aqueous layer. The combined organic layers were concentrated under reduced pressure to give 25.0 g of crude titled compound.

$^1$H-NMR (400 MHz, CDCl$_3$): δ7.345 (t, 1H), 7.468 (d, 1H), 7.128 (s, 1H), 7.020-7.093 (m, 1H), 5.440-5.850 (m, 3H), 4.414-4.920 (m, 5H), 3.760-4.025 (m, 4H), 3.416-3.514 (m, 3H), 2.232-2.501 (m, 3H), 1.848-2.211 (m, 3H), 1.352-1.804 (m, 12H).

$^{13}$C-NMR (100 MHz, CDCl$_3$): δ 158.996, 137.098, 136.399 (133.308), 134.418 (134.388, 133.636, 133.591), 131.694 (q), 129.932 (129.864), 128.634 (128.361, 128.240, 127.966), 127.784 (127.519, 127.420, 127.025), 123.940 (q), 118.312 (118.258, 118.160), 117.446 (q), 111.439 (q), 99.897 (99.867), 94.683, 83.350 (83.312, 83.039, 82.758), 80.307 (79.889, 79.494), 73.916 (73.885, 73.862, 73.824), 71.153 (71.054, 70.895, 70.811), 62.318 (61.604, 61.574), 54.780 (54.287, 54.226, 54.094), 45.141 (45.080, 44.875, 44.852), 39.152 (39.076, 38.985), 38.932 (38.894, 38.727, 38.583), 30.658 (30.620, 30.575, 30.544), 30.491 (30.461, 30.385), 25.413 (25.375, 25.345, 25.284), 19.394 (19.349, 19.273, 19.159), 19.022 (18.954, 18.916, 18.863).

Example 3

(Z)-7-((1R,2R,3R,5S)-5-hydroxy-3-((tetrahydro-2H-pyran-2-yl)oxy)-2-((3R,E)-3-((tetrahydro-2H-pyran-2-yl)oxy)-4-(3-(trifluoromethyl)phenoxy)but-1-en-1-yl)cyclopentyl)hept-5-enoic acid

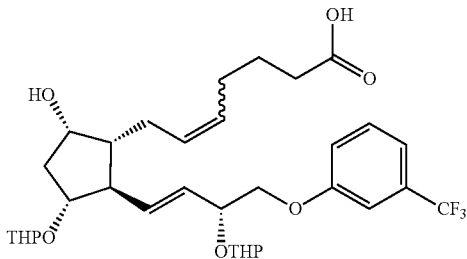

A suspension of (4-carboxybutyl)triphenylphosphonium bromide (62.33 g, 140.6 mmol) and potassium tert-butoxide (31.55 g, 281.1 mmol) in THF (500 mL) was cooled to −20° C. for 30 min. And, a solution of (3aR,4R,5R,6aS)-5-((tetrahydro-2H-pyran-2-yl)oxy)-4-((3R,E)-3-((tetrahydro-2H-pyran-2-yl)oxy)-4-(3-(trifluoromethyl)phenoxy)but-1-en-1-yl)hexahydro-2H-cyclopenta[b]furan-2-ol (25.0 g crude product from example 2) in THF (50 mL) at −20° C. was added and the reaction mixture was stirred for 16 hr. Then saturated aqueous solution of ammonium chloride (300 mL) was added and the resulting suspension was stirred for 30 min at room temperature. After separation of the organic layers, the aqueous layer was adjusted to have a pH of 6.0 by addition of a 2M sodium bisulfate solution and extracted with ethyl acetate (300 mL). The combined organic layers were dried over magnesium sulfate and concentrated under reduced pressure to give 44.0 g of crude titled compound.

$^1$H-NMR (400 MHz, CDCl$_3$): δ 7.362 (t, 1H), 7.185 (d, 1H), 7.145 (s, 1H), 7.039-7.112 (m, 1H), 5.616-5.822 (m, 2H), 5.419-5.551 (m, 1H), 5.300-5.364 (m, 1H), 4.760-4.948 (m, 1H), 4.644-4.662 (m, 1H), 4.493-4.581 (m, 1H), 3.772-4.162 (m, 5H), 3.423-3.538 (m, 2H), 2.403-2.583 (m, 1H), 1.974-2.315 (m, 7H), 1.410-1.957 (m, 17H).

$^{13}$C-NMR (100 MHz, CDCl$_3$): δ 177.797 (177.577), 158.996, 137.879 (137.538), 134.950 (134.562), 131.785 (q), 129.963 (129.887), 129.553 (129.447, 129.249, 129.113), 128.073 (127.997, 127.094, 127.048), 125.410 (q), 118.213 (118.099), 117.526 (q), 111.496 (q), 98.675 (98.546, 98.144, 97.939), 96.375 (96.337, 94.501, 94.410), 82.014 (81.916, 80.959, 80.610), 75.160 (74.948, 73.893, 73.870), 73.399 (73.202, 73.035, 72.807), 71.213 (71.084, 70.879, 70.819), 62.735 (62.621, 62.522, 62.447), 61.763 (61.695, 61.596, 61.498), 53.369 (53.110, 52.905, 52.807), 50.666 (50.552, 50.416), 41.452 (41.383, 39.645, 39.539), 33.117 (32.950), 30.924, 30.651 (30.620, 30.582, 30.552), 30.324, 26.385 (26.271), 25.724 (25.687, 25.656, 25.633), 25.406 (25.353), 24.487 (24.427), 19.607 (19.531, 19.341, 19.273), 18.992 (18.946, 18.810, 18.779).

Determination of Isomer Content of the Product:

A sample of the product was esterified using K$_2$CO$_3$ and 2-iodopropane in DMF. After 4 h at 60° C., water and ethyl acetate were added and the resultant solution was extracted with ethyl acetate. After drying-concentration of the extracts, a crude 11,15-protected travoprost was obtained. The crude 11,15-protected travoprost was deprotected using 3N HCl in THF and water. After 1 h at 25° C., saturated aqueous solution of sodium bicarbonate was added and the solution was extracted with ethyl acetate. After drying-concentration of the extracts, a crude travprost was obtained. UPLC (ACQUITY UPLC HSS C18) analysis showed that the crude product contains 2.8% 5,6-trans isomer.

Examples 4~7 Preparation of Protected Travoprost 1,9-Lactone from Wittig Reaction Product (8aR,9R, 10R,11aS,Z)-10-((tetrahydro-2H-pyran-2-yl)oxy)-9-((3R,E)-3-((tetrahydro-2H-pyran-2-yl)oxy)-4-(3-(trifluoromethyl)phenoxy)but-1-en-1-yl)-4,5,8,8a,9,10,11,11a-octahydrocyclopenta[b]oxecin-2(3H)-one

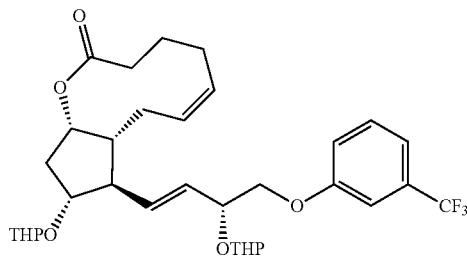

<sup>1</sup>H-NMR (400 MHz, CDCl<sub>3</sub>): δ 7.369 (t, 1H), 7.196 (d, 1H), 7.151 (s, 1H), 7.043-7.116 (m, 1H), 5.543-5.790 (m, 2H), 5.316-5.362 (m, 1H), 5.195 (m, 2H), 4.653-4.944 (m, 2H), 4.524-4.553 (m, 1H), 3.963-4.068 (m, 2H), 3.785-3.935 (m, 3H), 3.446-3.508 (m, 2H), 2.103-2.627 (m, 7H), 1.505-1.898 (m, 17H).

<sup>13</sup>C-NMR (100 MHz, CDCl<sub>3</sub>): δ 173.600 (173.554, 173.509, 173.455), 159.064 (159.034, 158.958, 158.927), 136.612 (136.475), 133.857 (133.667), 131.822 (q), 131.633 (131.375), 130.069, 129.948 (129.887), 129.158 (129.059), 127.420 (127.291), 123.917 (q), 118.289 (118.152), 117.526 (q), 111.420 (q), 99.427 (99.396, 99.146, 98.098), 95.844 (95.814, 94.842, 94.804), 81.703 (81.476, 78.295, 78.075), 74.766 (74.470), 73.946 (73.900), 71.304 (71.130, 70.948, 70.849), 62.538 (62.409, 62.052), 61.824 (61.642, 61.407), 44.898 (44.822, 44.791, 44.632), 39.531, 37.619, 36.047, 30.734 (30.689, 30.643), 30.529 (30.476), 26.711 (26.453), 25.489 (25.451, 25.413, 25.375), 19.591 (19.516), 19.068 (19.007), 18.810 (18.787).

Example 4

A solution of (Z)-7-((1R,2R,3R,5S)-5-hydroxy-3-((tetrahydro-2H-pyran-2-yl)oxy)-2-((3R,E)-3-((tetrahydro-2H-pyran-2-yl)oxy)-4-(3-(trifluoromethyl)phenoxy)but-1-en-1-yl)cyclopentyl)hept-5-enoic acid (22.0 g crude product from Example 3) in THF (125 mL) was treated with 2,2'-dipyridyl disulfide (8.39 g, 38.1 mmol) and triphenylphosphine (6.25 g, 23.9 mmol). This mixture was then stirred for 2 hr. at room temperature under an atmosphere of nitrogen. The resulting mixture was heated to 80° C. for 18 hr (TLC monitoring) followed by removal of THF under reduced pressure, and the residue was diluted with saturated aqueous solution of sodium bicarbonate (100 mL) and extracted with ethyl acetate (100 mL). The organic layer was dried over magnesium sulfate and concentrated under reduced pressure to give 25.0 g of a crude title compound. The crude title compound was purified by column chromatography to provide 8.0 g of the title compound (75% yield, 3 steps).

Determination of Isomer Content of the Product:

A sample of the product was hydrolyzed using methanol and 3N NaOH. After 2 h at 25° C., the mixture was acidified and extracted with ethyl acetate. After drying-concentration of the extracts, a crude 11,15-protected travoprost acid was obtained. The crude 11,15-protected travoprost acid was esterified using K<sub>2</sub>CO<sub>3</sub> and 2-iodopropane in DMF. After 2 h at 60° C. water and ethyl acetate were added and the resultant solution was extracted with ethyl acetate. After drying-concentration of the extracts, a crude 11,15-protected travoprost was obtained. The crude 11,15-protected travoprost was deprotected using 3N HCl in THF and water. After 1 h at 25° C., saturated aqueous solution of sodium bicarbonate was added and the resultant solution was extracted with ethyl acetate. After drying-concentration of the extracts, a crude travoprost was obtained. UPLC (ACQUITY UPLC HSS C18) analysis showed that no 5,6-trans isomer was detectable.

Example 5

To a solution of the (Z)-7-((1R,2R,3R,5S)-5-hydroxy-3-((tetrahydro-2H-pyran-2-yl)oxy)-2-((3R,E)-3-((tetrahydro-2H-pyran-2-yl)oxy)-4-(3-(trifluoromethyl)phenoxy)but-1-en-1-yl)cyclo pentyl)hept-5-enoic acid (5.00 g crude product from Example 3) and N,N-diisopropylethylamine (1.70 g, 13.2 mmol) in methylene chloride (100 mL) at room temperature under nitrogen, 2,4,6-trichlorobenzoyl chloride (1.90 g, 7.8 mmol) was added and the resulting mixture was stirred for 1 hr at room temperature. The reaction mixture was cooled to −15 to −20° C. and a solution of 4-dimethylaminopyridine (1.66 g, 13.6 mmole) in methylene chloride (15 mL) was added dropwise over 10 minutes. The reaction mixture was further stirred for 30 minutes at −15 to −16° C. The reaction mixture was quenched with saturated sodium bicarbonate solution (100 mL). The organic layer was separated. The aqueous layer was extracted with methylene chloride (50 mL). The combined organic layers were dried over magnesium sulfate, filtered and concentrated under reduced pressure to give 8.0 g of crude title compound. The crude title compound was purified by column chromatography providing 2.0 g of the title compound. (82.4% yield, 3 steps)

Determination of Isomer Content of the Product:

According to the same method as described in Example 4, UPLC (ACQUITY UPLC HSS C18) analysis of the crude product showed that no 5,6-trans isomer was detectable.

Example 6

To a solution of the (Z)-7-((1R,2R,3R,5S)-5-hydroxy-3-((tetrahydro-2H-pyran-2-yl)oxy)-2-((3R,E)-3-((tetrahydro-2H-pyran-2-yl)oxy)-4-(3-(trifluoromethyl)phenoxy)but-1-en-1-yl)cyclo pentyl)hept-5-enoic acid (3.0 g crude product from Example 3) and N,N-diisopropylethylamine (1.02 g, 7.9 mmole) in methylene chloride (60 mL) at room temperature under nitrogen, benzoyl chloride (0.66 g, 4.7 mmole) was added and the resulting mixture was stirred for 1 hr at room temperature. The reaction mixture was cooled to −15 to −20° C. and a solution of 4-dimethylaminopyridine (0.97 g, 7.9 mmole) in methylene chloride (10 mL) was added dropwise over 10 minutes. The reaction mixture was further stirred for 30 minutes at −15 to −16° C. The reaction mixture was quenched with saturated sodium bicarbonate solution (60 mL). The organic layer was separated. The aqueous layer was extracted with methylene chloride (50 mL). The combined organic layers were dried over magnesium sulfate, filtered and concentrated under reduced pressure to give 5.0 g of crude title compound. The crude title compound was purified by column chromatography providing 1.17 g of the title compound. (80.3% yield, 3 steps)
Determination of Isomer Content of the Product:

According to the same method as described in Example 4, UPLC (ACQUITY UPLC HSS C18) analysis of the crude product showed that no 5,6-trans isomer was detectable.

Example 7

To a solution of the (Z)-7-((1R,2R,3R,5S)-5-hydroxy-3-((tetrahydro-2H-pyran-2-yl)oxy)-2-((3R,E)-3-((tetrahydro-2H-pyran-2-yl)oxy)-4-(3-(trifluoromethyl)phenoxy)but-1-en-1-yl)cyclo pentyl)hept-5-enoic acid (3.0 g, 4.8 mmole) and 4-dimethylaminopyridine (0.03 g, 0.25 mmole) in methylene chloride (30 mL) under nitrogen. The reaction mixture was cooled to 0° C. and a solution of N,N'-dicyclohexyl-carbodiimide (1.98 g, 9.6 mmole) in methylene chloride (20 mL) was added dropwise over 5 minutes. The reaction mixture was further stirred for 3 hr at room temperature. The reaction mixture was quenched with saturated sodium bicarbonate solution (20 mL). The organic layer was separated. The aqueous layer was extracted with methylene chloride (20 mL). The combined organic layers were dried over magnesium sulfate, filtered and concentrated under reduced pressure to give 5.0 g of crude title compound. The crude title compound was purified by column chromatography providing 1.05 g of the title compound (72.0% yield, 3 steps)
Determination of Isomer Content of the Product:

According to the same method as described in Example 4, UPLC (ACQUITY UPLC HSS C18) analysis of the crude product showed that no 5,6-trans isomer was detectable.

Example 8

(8aR,9R,10R,11aS,Z)-10-hydroxy-9-((R,E)-3-hydroxy-4-(3-(trifluoromethyl)phenoxy)but-1-en-1-yl)-4,5,8,8a,9,10,11,11a-octahydrocyclopenta[b]oxecin-2(3H)-one

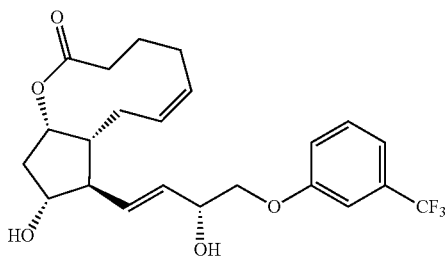

p-Toluenesulfonic acid monohydrate (0.20 g, 1.1 mmol) was add to a stirred solution of (8aR,9R,10R,11aS,Z)-10-((tetrahydro-2H-pyran-2-yl)oxy)-9-((3R,E)-3-((tetrahydro-2H-pyran-2-yl)oxy)-4-(3-(trifluoromethyl)phenoxy)but-1-en-1-yl)-4,5,8,8a,9,10,11,11a-octahydrocyclopenta[b]oxecin-2(3H)-one (14.0 g, 23.0 mmol) in methanol (150 mL). The mixture was stirred for 2 hr at room temperature (TLC monitoring). Then, the reaction mixture was quenched with saturated sodium bicarbonate aqueous solution (200 mL), and the methanol was removed under reduced pressure. The residue was extracted with ethyl acetate (200 mL). The organic layer was separated. The aqueous layer was extracted with ethyl acetate (200 mL). The combined organic layers were dried over magnesium sulfate, filtered and concentrated under reduced pressure to give 15.0 g of the crude product. The crude product was subjected to further purification by flash column chromatography to obtain 8.2 g of the title compound as a solid. DSC analysis showed that the solid contained two crystalline forms (mp 92~97° C. and mp 113~118° C.) The solid was recrystallized from a mixture of hexane and ethyl acetate to give 7.3 g of title compound as a single crystalline form (mp 113~118° C.). The x-ray powder diffraction pattern of crystalline title compound (mp 115~120° C.) has characteristic peaks expressed in degrees 2θ at approximately 10.7, 12.1, 13.4, 14.5, 14.8, 16.0, 16.6, 17.7, 18.4, 18.5, 19.4, 20.5, 21.0, 22.0, 22.4, 23.3, 24.6, 24.7, 25.1, 28.9, 29.9, 37.9, 44.1.

¹H-NMR (400 MHz, CDCl₃): δ 7.387 (t, 1H), 7.227 (d, 1H), 7.145 (s, 1H), 7.080 (m, 1H), 5.721-5.776 (m, 1H), 5.623-5.683 (m, 1H), 5.309-5.354 (m, 1H), 5.222 (m, 2H), 4.527 (m, 1H), 3.947-4.033 (m, 2H), 3.812-3.874 (m, 1H), 3.510 (br s, 1H), 3.409 (br s, 1H), 2.561-2.635 (m, 1H), 2.098-2.418 (m, 6H), 1.587-1.870 (m, 5H).

¹³C-NMR (100 MHz, CDCl₃): δ 173.471, 158.593, 135.147, 131.937 (q), 131.534, 131.147, 130.099, 127.276, 123.856 (q), 118.099, 117.928 (q), 111.446 (q), 75.935, 71.897, 70.993, 56.222, 44.981, 40.260, 36.040, 26.711, 26.559, 25.269.

Example 9

(Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoic acid (Travoprost acid)

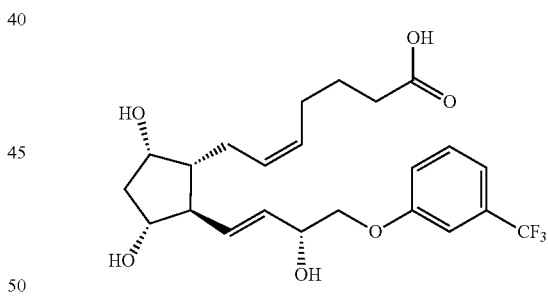

A solution of (8aR,9R,10R,11aS,Z)-10-hydroxy-9-((R,E)-3-hydroxy-4-(3-(trifluoromethyl)phenoxy)but-1-en-1-yl)-4,5,8,8a,9,10,11,11a-octahydrocyclopenta[b]oxecin-2(3H)-one (3.0 g from Example 8) in 2-propanol (25 mL) was treated with 3N potassium hydroxide aqueous solution (6.8 mL). This mixture was stirred at 50° C. for 2 hr. The reaction mixture was cooled and further adjusted with 3N hydrochloric acid aqueous solution to a pH of 8.5±0.2, and most of the solvent was removed under reduced pressure. The residue was diluted with saturated aqueous solution of sodium bicarbonate (20 mL) and ethyl acetate (20 mL). The mixture was stirred at room temperature for 5 minutes. The organic phase and the aqueous phase were separately collected. The aqueous layer was adjusted to a pH of 3.0±0.2 with 3N hydrochloric acid aqueous solution at room temperature and extracted with ethyl acetate (100 mL). The organic layer was dried over magnesium sulfate and concentrated under reduced pressure to give 3.3 g of crude Travoprost acid.

Determination of Isomer Content of the Product:

A sample of this product was esterified using $K_2CO_3$ and 2-iodopropane in DMF. After 4 h at 60° C., water and ethyl acetate were added and the reaction was extracted with ethyl acetate. After drying-concentration of the extracts, crude travprost was obtained. UPLC (ACQUITY UPLC HSS C18) analysis of the crude product showed that no isomer was detectable.

$^1$H-NMR (400 MHz, $CDCl_3$): δ 7.343 (t, 1H), 7.179 (d, 1H), 7.116 (s, 1H), 7.055 (d, 1H), 5.631-5.704 (m, 2H), 5.278-5.422 (m, 2H), 4.520-4.527 (m, 1H), 3.950-4.008 (m, 2H), 2.034-2.361 (m, 8H), 1.337-1.745 (m, 7H).

$^{13}$C-NMR (100 MHz, $CDCl_3$): δ 171.411, 158.794, 135.472, 131.877 (q), 130.113, 130.010, 129.682, 129.106, 123.960 (q), 118.097, 117.769 (q), 111.549 (q), 77.382, 71.751, 71.065, 70.907, 55.292, 49.952, 42.597, 31.527, 26.120, 25.094, 24.227.

Example 10

(Z)-isopropyl 7-((1R,2R,3R,5S)-3,5-dihydroxy-2-((R,E)-3-hydroxy-4-(3-(trifluoromethyl) phenoxy) but-1-en-1-yl)cyclopentyl)hept-5-enoate (Travoprost)

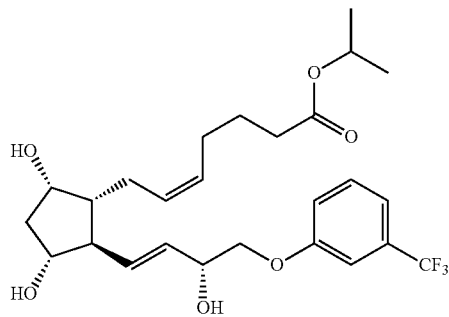 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

A solution of crude Travoprost acid (1.1 g from Example 9) in DMF (11 mL) was treated with $K_2CO_3$ (0.90 g, 6.5 mmol) and 2-iodopropane (0.74 g, 4.4 mmol). This mixture was then stirred at 80° C. for 2 hr under an atmosphere of nitrogen (TLC monitoring). Water (30 mL) and ethyl acetate (30 mL) were added and the mixture was stirred for 10 min. The aqueous layer was separated and extracted with ethyl acetate (30 mL), and the combined organic layer was dried over magnesium sulfate and concentrated under reduced pressure to give 1.0 g of crude Travoprost. The crude Travoprost was purified by column chromatography and then concentrated under reduced pressure to provide 0.89 g of Travoprost (78.3% yield, 2 steps). UPLC (ACQUITY UPLC HSS C18) analysis of the product showed that no isomer and impurities were detectable.

$^1$H-NMR (400 MHz, $CDCl_3$): δ 7.337 (t, 1H), 7.209 (d, 1H), 7.142 (s, 1H), 7.084 (d, 1H), 5.647-5.744 (m, 2H), 5.334-5.434 (m, 2H), 4.970 (heptet, 1H), 4.518-4.528 (m, 1H), 4.163-4.170 (m, 1H), 3.939-4.020 (m, 3H), 3.294 (br s, 1H), 3.262 (br s, 1H), 2.588 (br s, 1H), 2.360-2.410 (m, 1H), 2.015-2.305 (m, 7H), 1.760 (dd, 1H), 1.646 (quintet, 2H), 1.494-1.554 (m, 1H), 1.201 (d, 6H)

13C-NMR (100 MHz, CDCl3): δ 173.511, 158.656, 135.420, 131.857 (q), 130.015, 129.794, 128.901, 123.857 (q), 118.038, 117.748 (q), 111.466 (q), 77.710, 72.649, 71.992, 70.840, 67.672, 55.748, 50.176, 42.824, 33.970, 26.565, 25.450, 24.802, 21.771

Example 11

(Z)-isopropyl 7-((1R,2R,3R,5S)-3,5-bis((triethylsilyl)oxy)-2-((R,E)-3-((triethylsilyl)oxy)-4-(3-(trifluoromethyl)phenoxy)but-1-en-1-yl)cyclopentyl)hept-5-enoate

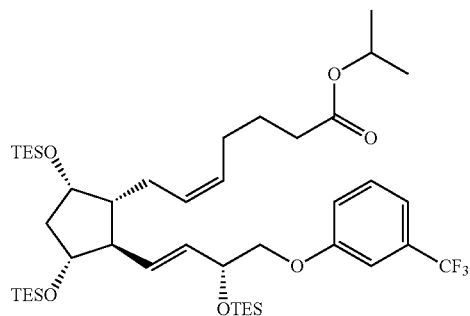

A solution of crude Travoprost acid (1.1 g from Example 9) in DMF (11 mL) was treated with $K_2CO_3$ (0.90 g, 6.5 mmol) and 2-iodopropane (0.74 g, 4.4 mmol). This mixture was then stirred at 80° C. for 2 hr under an atmosphere of nitrogen (TLC monitoring). Water (30 mL) and ethyl acetate (30 mL) were added and the mixture was stirred for 10 min. The aqueous layer was separated and extracted with ethyl acetate (30 mL), and the combined organic layer was dried over magnesium sulfate and concentrated under reduced pressure to give 1.2 g of crude Travoprost. The crude Travoprost was dissolved in 10 mL ethyl acetate in 25 mL round-bottom flask, followed by addition of imidazole (0.82 g, 12 mmol) at room temperature. Chlorotriethylsiliane (1.6 g, 10.6 mmol) was added into this flask and stirred for 10 minutes. White solid was produced and filtered off and washed with 50 mL ethyl acetate twice. All organic solvent was combined and washed with 15 mL saturated $NaHCO_3$ aqueous solution twice. The organic layer was dried over anhydrous $MgSO_4$, solid was filtered off and solvent was evaporated under vacuum. The crude product was purified by chromatography on silica gel using a mixture of hexane and ethyl acetate as a gradient eluent. Yield of the title compound was 1.85 g. (91.6%)

1H-NMR (400 MHz, CDCl3): δ 7.360 (t, 1H), 7.181 (d, 1H), 7.088 (s, 1H), 7.035 (d, 1H), 5.582-5.679 (m, 2H), 5.396-5.458 (m, 1H), 5.266-5.347 (m, 1H), 4.985 (heptet, 1H), 4.516-4.554 (m, 1H), 4.114-4.148 (m, 1H), 3.813-3.871 (m, 3H), 2.385-2.450 (m, 1H), 2.157-2.276 (m, 4H), 2.006-2.087 (m, 3H), 1.577-1.682 (m, 3H), 1.395-1.457 (m, 1H), 1.208 (d, 6H), 0.905-0.987 (m, 27H), 0.514-0.666 (m, 18H)

$^{13}$C-NMR (100 MHz, $CDCl_3$): δ 173.137, 159.026, 133.644, 131.769 (q), 130.798, 129.849, 129.811, 128.801, 123.955 (q), 117.985, 117.260 (q), 111.059 (q), 76.853, 72.891, 71.540, 71.145, 67.312, 54.484, 49.437, 44.928, 34.127, 26.726, 25.034, 24.905, 21.785, 6.878, 6.794, 4.995, 4.897, 4.874

Example 12

(Z)-isopropyl 7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate (Travoprost)

The product of Example 11 (0.8 g) was dissolved in 10 ml acetone and 2 ml water, followed by addition of 0.1 g p-toluenesulfonic acid monohydrate. The reaction solution was stirred at room temperature for 1 hour and concentrated until two separate layers were observed. 30 ml ethyl acetate was added for extraction and phase separation. The organic layer was washed with saturated sodium bicarbonate solution and brine, dried over anhydrous magnesium sulfate, and subjected to vacuum evaporation for removal of the solvent until dryness. The crude Travoprost was purified by column chromatography and then concentrated under reduced pressure to provide 0.44 g of Travoprost. UPLC (ACQUITY UPLC HSS C18) analysis of the product showed that no isomer and impurities were detectable and the purity was higher then 99.9%.

Examples 13~18 Preparation of Travoprost and its Intermediates Via Conjugate Addition

Example 13

(5Z)-isopropyl 7-((1R,2R,3R)-2-((R,E)-4-(3-(trifluoromethyl)phenoxy)-3-(triethylsilyloxy)but-1-enyl)-3-triethylsilyloxy-5-oxocyclopentyl)hept-5-enoate

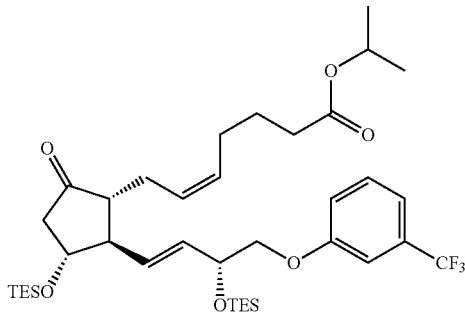

A 500 mL three-necked flask was flame dried and allowed to be cooled under nitrogen. (R,E)-triethyl((4-(tributylstannyl)-1-(3-(trifluoromethyl)phenoxy)but-3-en-2-yl)oxy)silane (22.53 g, 35.46 mmol) and 200 mL tetrahydrofuran were added to the reaction flask, followed by dropwise addition of n-butyl lithium (22.2 mL, 1.6 M in hexane) at −70° C. A suspension solution of copper cyanide (3.18 g, 35.46 mmol) in 30 mL tetrahydrofuran was cooled to −10° C. and followed by dropwise addition of methyl lithium (17.76 mL, 2 M in ether). The homogenous organo-metallic solution was cooled and added into the reaction flask while stirring for 30 minutes. Then, a solution of (R,Z)-isopropyl 7-(3-triethylsilyloxy-5-oxocyclopent-1-en-1-yl)hept-5-enoate (4.5 g, containing 5% of 5,6-trans isomer) in 15 mL tetrahydrofuran at −70° C. was added to the reaction mixture for 10 minutes. After being stirred for another 20 minutes, the reaction mixture was poured into a mixture of 9/1 (v/v) saturated aqueous NH$_4$Cl/NH$_4$OH solution to be phase separated. The aqueous layer was extracted with ethyl acetate. The organic layers were combined and dried over anhydrous MgSO$_4$. The solid was filtered off and organic solvent was evaporated off under vacuum. The crude product was purified by chromatography on silica gel using a mixture of hexane and ethyl acetate as a gradient eluent. Yield of the title compound was 5.10 g (59.3%).

$^1$H-NMR (400 MHz, CDCl$_3$): δ 7.346 (t, 1H), 7.167 (d, 1H), 7.068 (s, 1H), 7.019 (d, 1H), 5.670-5.782 (m, 2H), 5.264-5.408 (m, 2H), 4.956 (heptet, 1H), 4.539-4.546 (m, 1H), 4.033-4.087 (m, 1H), 3.862 (d, 2H), 2.491-2.656 (m, 2H), 2.119-2.400 (m, 5H), 1.999-2.049 (m, 3H), 1.586-1.655 (m, 2H), 1.182 (d, 6H), 0.894-0.969 (m, 18H), 0.528-0.652 (m, 12H), $^{13}$C-NMR (100 MHz, CDCl$_3$): δ 214.785, 172.954, 158.882, 132.255, 131.800 (q), 131.428, 130.927, 129.910, 126.464, 123.910 (q), 117.985, 117.389 (q), 111.930 (q), 72.678, 72.564, 70.864, 67.335, 53.961, 52.837, 47.706, 33.968, 26.605, 25.079, 24.723, 21.740, 6.764, 6.680, 4.859, 4.752.

Example 14

(5Z)-isopropyl 7-((1R,2R,3R,5S)-2-((R,E)-4-(3-(trifluoromethyl)phenoxy)-3-(triethylsilyloxy)but-1-enyl)-5-dihydroxy-3-(triethylsilyloxy)cyclopentyl)hept-5-enoate

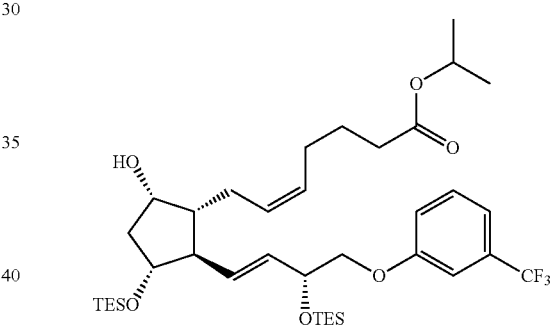

A 100 mL three-necked flask was flame dried and allowed to be cooled under nitrogen. (Z)-isopropyl 7-((1R,2R,3R,5S)-3-triethylsilyloxy-2-((R,E)-3-triethylsilyloxy-4-(3-(trifluoromethyl)phenoxy)but-1-en-1-yl)-5-hydroxycyclopentyl)hept-5-enoate (3.6 g, 4.95 mmol) and 50 mL tetrahydrofuran were added to the reaction flask, followed by dropwise addition of L-Selectride (4.95 ml, 1M in tetrahydrofuran) at −70° C. Then, the reaction mixture was warmed to room temperature and quenched by 50 mL saturated aqueous ammonium chloride. The reaction mixture was phase separated and the aqueous layer was extracted with ethyl acetate. The organic layers were combined and dried over anhydrous MgSO$_4$. The solid was filtered off and organic solvent was evaporated off under vacuum. The crude product was purified by chromatography on silica gel using a mixture of hexane and ethyl acetate as a gradient eluent. Yield of the titled compound was 2.4 g (66.5%).

$^1$H-NMR (400 MHz, CDCl$_3$): δ 7.352 (t, 1H), 7.173 (d, 1H), 7.082 (s, 1H), 7.029 (d, 1H), 5.541-5.667 (m, 2H), 5.295-5.465 (m, 2H), 4.975 (heptet, 1H), 4.471-4.512 (m, 1H), 4.101-4.135 (m, 1H), 4.007-4.034 (m, 1H), 3.825-3.909 (m, 2H), 2.626-2.647 (m, 1H), 2.295-2.368 (m, 2H), 2.235 (t, 2H), 2.036-2.172 (m, 2H), 1.906-1.967 (m, 1H), 1.799-1.834 (m, 1H), 1.611-1.685 (m, 2H), 1.455-1.527 (m, 1H), 1.198 (d, 6H), 0.902-0.973 (m, 18H), 0.532-0.650 (m, 12H)

$^{13}$C-NMR (100 MHz, CDCl3): δ 173.159, 158.958, 133.553, 131.781 (q), 130.023, 129.879, 129.363, 129.310, 123.932 (q), 117.962, 117.344 (q), 111.135 (q), 79.290, 74.250, 72.678, 71.198, 67.335, 56.382, 51.448, 43.175, 34.066, 26.552, 26.461, 24.905, 21.770, 6.749, 6.688, 4.843, 4.638.

Comparative Example 15

Preparation of Travoprost Using Conjugate Addition Approach without Macrocyclic Lactonization The product of Example 14 (0.8 g) was dissolved in 10 ml acetone and 2 ml water, followed by addition of 0.1 g p-toluenesulfonic acid monohydrate. The reaction solution was stirred at room temperature for 1 hour and concentrated until two separate layers were observed. 30 ml ethyl acetate was added for extraction and phase separation. The organic layer was washed with saturated sodium bicarbonate solution and brine, dried over anhydrous magnesium sulfate, and subjected to vacuum evaporation for removal of the solvent until dryness. The crude Travoprost was purified by column chromatography and then concentrated under reduced pressure to provide 0.69 g of Travoprost. UPLC (ACQUITY UPLC HSS C18) analysis of the product showed that 4.95% 5,6-trans isomer, 0.5% 15β-isomer and some other isomers were found.

Examples 16~18 Preparation of Travoprost Using Conjugate Addition Approach and Via Macrocyclic Lactonization Example 16

(5Z)-7-((1R,2R,3R,5S)-2-((R,E)-4-(3-(trifluoromethyl)phenoxy)-3-(triethylsilyloxy)but-1-enyl)-5-hydroxy-3-(triethylsilyloxy)cyclopentyl)hept-5-enoic acid

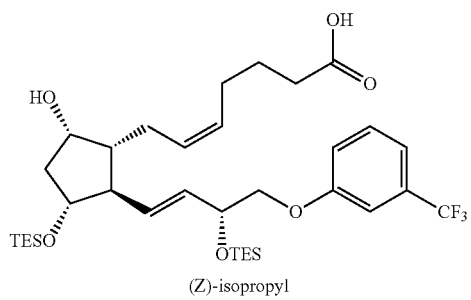

(Z)-isopropyl 7-((1R,2R,3R,5S)-3-((triethylsilyl)oxy)-2-((R,E)-3-((triethylsilyl)oxy)-4-(3-(trifluoro methyl)phenoxy)but-1-en-1-yl)-5-hydroxycyclopentyl)hept-5-enoate (1.5 g from Example 14) in 10 mL methyl isobutyl ketone and 0.2 g *Candida antarctica* lipase was added into 25 mL round-bottom flask. The reaction mixture was stirred at room temperature for 3 days. Then, the Lipase was filtered off and solvent was evaporated off under vacuum to obtain 1.5 g crude product.

Example 17

(8aR,9R,10R,11aS,Z)-10-(triethylsilyloxy)-9-((3R,E)-3-(triethylsilyloxy)-4-(3-(tri fluoromethyl)phenoxy)but-1-en-1-yl)-4,5,8,8a,9,10,11,11a-octahydro-cyclopenta[b]oxecin-2(3H)-one

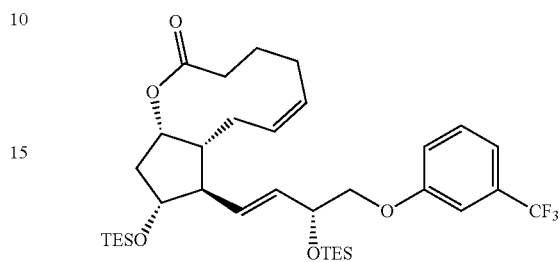

To a solution of (Z)-7-((1R,2R,3R,5S)-5-hydroxy-3-((triethylsilyl)oxy)-2-((R,E)-3-((triethylsilyl)oxy)-4-(3-(trifluoromethyl)phenoxy)but-1-en-1-yl)cyclopentyl)hept-5-enoic acid (1.5 g, 2.19 mmole) and N,N-diisopropylethylamine (0.48 g from Example 16) in methylene chloride (30 mL) at room temperature under nitrogen, benzoyl chloride (0.30 g, 2.13 mmole) was added and the resulting mixture was stirred for 1 hr at room temperature. The reaction mixture was cooled to −15 to −20° C. and a solution of 4-dimethylaminopyridine (0.45 g, 3.69 mmole) in methylene chloride (5 mL) was added dropwise over 5 minutes. The reaction mixture was further stirred for 30 minutes at −15 to −16° C. The reaction mixture was quenched with saturated sodium bicarbonate solution (30 mL). The organic layer was separated. The aqueous layer was extracted with methylene chloride (30 mL). The combined organic layer was dried over magnesium sulfate, filtered and concentrated under reduced pressure to give 2.7 g of crude title compound. The crude title compound was purified by column chromatography providing 0.9 g of the title compound. (61.6% yield).

Example 18

(8aR,9R,10R,11aS,Z)-10-hydroxy-9-((R,E)-3-hydroxy-4-(3-(trifluoromethyl)phenoxy)but-1-en-1-yl)-4,5,8,8a,9,10,11,11a-octahydrocyclopenta[b]oxecin-2(3H)-one

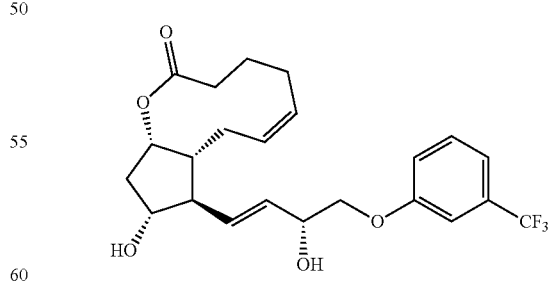

p-Toluenesulfonic acid monohydrate (0.20 g, 1.1 mmol) was add to a stirred solution of (8aR,9R,10R,11aS,Z)-10-(triethylsilyloxy)-9-((3R,E)-3-(triethylsilyloxy)-4-(3-(trifluoromethyl)phenoxy)but-1-en-1-yl)-4,5,8,8a,9,10,11,11a-octahydrocyclopenta[b]oxecin-2(3H)-one (0.9 g from example 17) in methanol (50 mL). The mixture was stirred for 2 hr at room temperature (TLC monitoring). Then, the reaction mixture was quenched with saturated sodium bicarbonate aqueous solution (20 mL), and the methanol was removed under reduced pressure. The residue was extracted with ethyl acetate. The organic layer was separated. The aqueous layer was extracted with ethyl acetate. The combined organic layer was dried over magnesium sulfate, filtered and concentrated under reduced pressure to give 1.1 g of the crude product. The crude product was subjected to further purification by flash column chromatography to obtain 0.7 g of the product.

Determination of Isomer Content of the Product Before Crystallization:

A sample of the product before crystallization was hydrolyzed using methanol and 3N NaOH. After 2 h at 25° C., the mixture was acidified and extracted with ethyl acetate. After drying-concentration of the extracts, crude travprost acid was obtained. The crude travprost acid was esterified using $K_2CO_3$ and 2-iodopropane in DMF. After 2 h at 60° C., water and ethyl acetate were added and extracted with ethyl acetate. After drying-concentration of the extracts, crude travprost was obtained. UPLC (ACQUITY UPLC HSS C18) analysis of the crude product showed that 0.02% 5,6-trans isomer and 0.01% 15β-isomer were found.

The product was recrystallized from a mixture of hexane and ethyl acetate to give 0.5 g of title compound as a single crystalline form (mp 113~118° C.).

Determination of Isomer Content of the Crystalline Product:

A sample of the crystalline product was also subjected to the same method as described above for determining the isomer content. Crude travoprost was obtained and UPLC (ACQUITY UPLC HSS C18) analysis of the crude product showed that no 5,6-trans isomer, 15β-isomer or any other isomers were found.

Comparative Examples 19~23 Preparation of Travoprost and its Intermediates Via Grubb's Catalysis Cyclization Comparative Example 19

(2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentanone

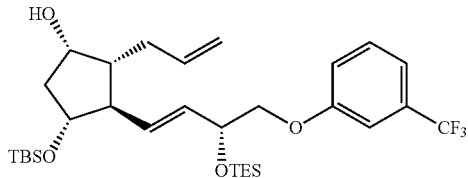

A 100 ml three-necked flask was flame dried and allowed to be cooled under nitrogen. (R,E)-triethyl(4-(tributylstannyl)-1-(3-(trifluoromethyl) phenoxy)but-3-en-2-yloxy)silane (15.11 g, 23.8 mmol) and 20 ml tetrahydrofuran were added to the reaction flask, followed by dropwise addition of n-butyl lithium (14.9 ml, 1.6 M in hexane) at −70° C. A suspension solution of copper cyanide (2.13 g, 23.8 mmol) in 20 ml tetrahydrofuran was cooled to −20° C., followed by dropwise addition of methyl lithium (11.9 ml, 2 M in ether). The homogenous organo-metallic solution was cooled and added into the reaction flask while stirring for 60 minutes. Then, a solution of (R)-2-allyl-4-(tert-butyldimethylsilyloxy)cyclopent-2-enone (3 g, 11.9 mmol) in 20 ml tetrahydrofuran at −70° C. was added to the reaction mixture for 10 minutes. After being stirred for another 20 minutes, the reaction mixture was poured into a mixture of 9/1 (v/v) saturated aqueous $NH_4Cl/NH_4OH$ solution to be phase separated. The aqueous layer was extracted with ethyl acetate. The organic layers were combined and dried over magnesium sulfate. The solid was filtered off and organic solvent was evaporated off under vacuum. The crude product was purified by chromatography and then concentrated under reduced pressure to provide 2.68 g of the title compound (37.7% yield).

$^1$H-NMR (400 MHz, $CDCl_3$): δ 7.376 (t, 1H), 7.201 (d, 1H), 7.088 (s, 1H), 7.036 (d 1H), 5.691-5.753 (m, 3H), 5.024 (d, 2H), 4.561 (s, 1H), 4.088-4.143 (m, 1H), 3.877 (d, 2H), 2.563-2.635 (m, 2H), 2.438-2.473 (m, 1H), 2.261-2.311 (m, 1H), 2.070-2.200 (m, 2H), 0.970 (t, 9H), 0.867 (s, 9H), 0.644 (q, 6H), 0.052 (s, 6H)

$^{13}$C-NMR (100 MHz, $CDCl_3$): δ 214.838, 158.867, 134.874, 132.369, 131.982 (q), 131.268, 129.932, 123.917 (q), 118.031, 117.370, 111.010, 72.929, 72.625, 70.788, 53.528, 52.609, 74.501, 31.736, 25.671, 6.802, 4.866, −4.675 (d)

Comparative Example 20

(1S,2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentanol

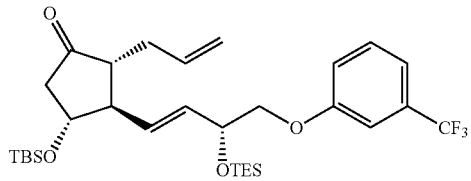

A 500 ml three-necked flask was flame dried and allowed to be cooled under nitrogen. (2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentanone (2.68 g, 4.48 mmol) and 30 ml tetrahydrofuran were added to the reaction flask, followed by dropwise addition of L-Selectride (4 ml, 1M in tetrahydrofuran) at −70° C. Then, the reaction mixture was warmed to room temperature and quenched by 30 ml saturated aqueous ammonium chloride. The reaction mixture was phase separated and the aqueous layer was extracted with ethyl acetate. The organic layers were combined and dried over anhydrous magnesium sulfate. The solid was filtered off and organic solvent was evaporated off under vacuum. The crude product was purified by chromatography and then concentrated under reduced pressure to provide 2.5 g of the title compound (93% yield).

$^1$H-NMR (400 MHz, $CDCl_3$): δ 7.369 (t, 1H), 7.193 (d, 1H), 7.095 (s, 1H), 7.038 (d 1H), 5.820-5.882 (m, 1H), 5.544-5.663 (m, 2H), 5.061 (d, 1H), 4.965 (d, 1H), 4.500 (d, 1H), 4.150 (s, 1H), 4.033 (d, 1H), 3.841-3.918 (m, 2H), 2.329-2.372 (m, 2H), 2.152-2.187 (m, 1H), 1.967-2.003 (m, 1H), 1.798-1.834 (m, 1H), 1.551-1.572 (m, 1H), 0.964 (t, 9H), 0.869 (s, 9H), 0.630 (q, 6H), 0.046 (s, 6H)

$^{13}$C-NMR (100 MHz, $CDCl_3$): δ 158.935, 137.697, 133.401, 131.625 (q), 130.327, 129.894, 123.936 (q), 117.970, 115.382, 108.862, 79.373, 74.060, 72.640, 71.168, 60.115, 56.131, 50.803, 43.099, 33.034, 25.732, 6.779, 4.843, −4.778 (d)

Comparative Example 21

(1S,2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentyl hex-5-enoate

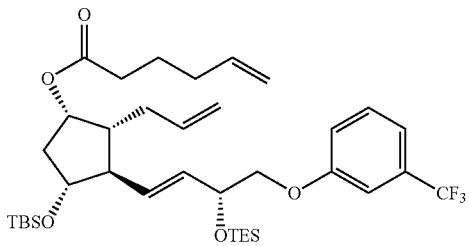

A 50 ml two-necked round-bottom flask was flame dried and allowed to be cooled under nitrogen. (1S,2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentanol (1 g, 1.66 mmol) in 10 ml of DMF, 0.05 g (0.33 mmol) of DMAP, 0.21 g (1.83 mmol) of 5-hexenoic acid, and 0.41 g (2.00 mmol) of N,N'-dicyclohexylcarbodiimide were added to the reaction flask. The reaction mixture was heated at 40° C. for 24 hours. The reaction was quenched with 10 ml saturated aqueous sodium bicarbonate. The reaction mixture was phase separated and the aqueous layer was extracted with ethyl acetate. The organic layers were combined and dried over anhydrous magnesium sulfate. The solid was filtered off and organic solvent was evaporated off under vacuum. The crude product was purified by chromatography and then concentrated under reduced pressure to provide 1.05 g of the title compound (90.52% yield).

$^1$H-NMR (400 MHz, CDCl$_3$): δ 7.379 (t, 1H), 7.202 (d, 1H), 7.093 (s, 1H), 7.038 (d 1H), 5.643-5.824 (m, 4H), 4.926-5.085 (m, 4H), 4.553 (d, 1H), 3.865-3.925 (m, 3H), 3.203 (s, 1H), 2.293 (q, 2H), 2.114 (s, 3H), 1.912 (s, 2H), 1.675-1.760 (m, 3H), 1.564-1.602 (m, 2H), 0.978 (t, 9H), 0.854 (s, 9H), 0.655 (q, 6H), 0.026 (s, 6H)

$^{13}$C-NMR (100 MHz, CDCl$_3$): δ 173.099, 158.943, 136.581, 132.521, 132.027, 131.663 (q), 129.902, 123.938 (q), 117.985, 117.401, 115.769, 115.359, 111.116, 73.855, 72.754, 70.879, 55.744, 55.357, 46.727, 42.233, 34.916, 33.080, 31.653, 28.806, 25.755, 6.809, 4.904, −4.599 (d)

Comparative Example 22

(8aR,9R,10R,11aS,Z)-10-(tert-butyldimethylsilyloxy)-9-((R,E)-3-(triethylsilyloxy)-4-(3-(trifluoromethyl)phenoxy)but-1-enyl)-4,5,8,8a,9,10,11,11a-octahydrocyclopenta[b]oxecin-2(3H)-one

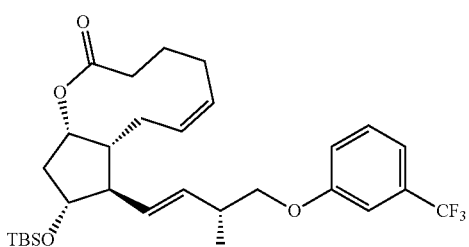

A 50 ml two-necked round-bottom flask was flame dried and allowed to be cooled under nitrogen. (1S,2R,3R,4R)-2-allyl-4-(tert-butyldimethylsilyloxy)-3-((R,E)-3-(triethylsilyloxy)-4-(3-(trifluoromethyl)phenoxy)but-1-enyl)cyclopentyl hex-5-enoate (0.2 g, 0.29 mmol) in 4 ml of dichloromethane, and 0.02 g of Grubb's catalyst were added to the reaction flask. The reaction mixture was heated at 40° C. for 18 hours. The reaction was quenched with 0.4 ml ethylamine with stirring for 1 hour. The reaction mixture was phase separated and the aqueous layer was extracted with ethyl acetate and 4 ml saturated aqueous sodium bicarbonate solution. The organic layers were combined and dried over anhydrous magnesium sulfate. The solid was filtered off and organic solvent was evaporated off under vacuum. The crude product was purified by chromatography and then concentrated under reduced pressure to provide 30 mg of the title compound (16% yield).

$^1$H-NMR (400 MHz, CDCl$_3$): δ 7.346 (t, 1H), 7.187 (d, 1H), 7.075 (s, 1H), 7.023 (d 1H), 5.588-5.723 (m, 2H), 5.182-5.425 (m, 3H), 4.539 (q, 1H), 2.189-2.557 (m, 4H), 2.012-2.085 (m, 2H), 1.873-1.920 (m, 2H), 1.513-1.711 (m, 4H), 0.960 (t, 9H), 0.855 (s, 9H), 0.635 (q, 6H), 0.018 (s, 6H)

$^{13}$C-NMR (100 MHz, CDCl$_3$): δ 173.569, 158.912, 132.088, 131.944, 131.299 (q), 129.902, 127.686, 125.295 (q), 118.008, 117.340, 111.040, 76.972, 72.739, 71.950, 70.895, 55.547, 44.533, 41.581, 36.123, 34.006, 31.888, 29.694, 28.806, 25.755, 6.817, 4.866, −4.588 (d)

Comparative Example 23

(8aR,9R,10R,11aS,Z)-10-hydroxy-9-((R,E)-3-hydroxy-4-(3-(trifluoromethyl)phenoxy)but-1-enyl)-4,5,8,8a,9,10,11,11a-octahydrocyclopenta[b]oxecin-2(3H)-one

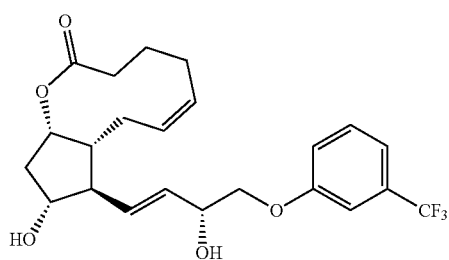 [SMILES: O=C1CCC/C=C\C[C@@H]2[C@@H](/C=C/[C@@H](O)COc3cccc(C(F)(F)F)c3)[C@H](O)C[C@@H]2O1]

(8aR,9R,11R,11aS,Z)-10-(tert-butyldimethylsilyloxy)-9-((R,E)-3-(triethyl silyloxy)-4-(3-(trifluoromethyl)phenoxy)but-1-enyl)-4,5,8,8a,9,10,11,11a-octahydrocyclopenta[b]oxecin-2(3H)-one (20 mg, 0.003 mmol) and 1 ml TBAF (1M in tetrahydrofuran) was added into 10 ml round-bottom flask. The reaction mixture was stirred for 2 hours and quenched by 1 ml saturated NaHCO$_3$ aqueous solution. Then, the mixture was phase separated and the aqueous layer was extracted with ethyl acetate. The organic layers were combined and dried over anhydrous MgSO$_4$. The solid was filtered off and organic solvent was evaporated under vacuum. The crude product was purified by chromatography and then concentrated under reduced pressure to provide 10 mg of the title compound as an oil. (80% yield).
Determination of Isomer Content of the Product:
A sample of this product was hydrolyzed using methanol and 3N NaOH. After 2 h at 25° C., the mixture was acidified and extracted with ethyl acetate. After drying-concentration of the extracts, crude travoprost acid was obtained. The crude travoprost acid was esterified using $K_2CO_3$ and 2-iodopropane in DMF. After 2 h at 60° C., water and ethyl acetate were added and phase separated, the aqueous layer was extracted with ethyl acetate. After drying-concentration of the extracts, crude travoprost was obtained. UPLC (ACQUITY UPLC HSS C18) analysis of the crude product showed that 2.6% 5,6-trans isomer and some other isomers were found.

$^1$H-NMR (400 MHz, CDCl$_3$): δ 7.387 (t, 1H), 7.227 (d, 1H), 7.145 (s, 1H), 7.080 (m, 1H), 5.721-5.776 (m, 1H), 5.623-5.683 (m, 1H), 5.309-5.354 (m, 1H), 5.222 (m, 2H), 4.527 (m, 1H), 3.947-4.033 (m, 2H), 3.812-3.874 (m, 1H), 3.510 (br s, 1H), 3.409 (br s, 1H), 2.561-2.635 (m, 1H), 2.098-2.418 (m, 6H), 1.587-1.870 (m, 5H)

$^{13}$C-NMR (100 MHz, CDCl3): δ 173.471, 158.593, 135.147, 131.937 (q), 131.534, 131.147, 130.099, 127.276, 123.856 (q), 118.099, 117.928 (q), 111.446 (q), 75.935, 71.897, 70.993, 56.222, 44.981, 40.260, 36.040, 26.711, 26.559, 25.269

Example 24~30 Preparation of Latanoprost and its Intermediates Via Wittig Reaction Example 24

(3aR,4R,5R,6aS)-4-((3R)-5-phenyl-3-((tetrahydro-2H-pyran-2-yl)oxy)pentyl)-5-((tetrahydro-2H-pyran-2-yl)oxy)hexahydro-2H-cyclopenta[b]furan-2-one

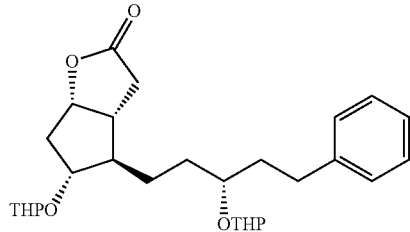

p-Toluenesulfonic acid monohydrate (0.46 g, 2.4 mmol) was added to a solution of (3aR,4R,5R,6aS)-hexahydro-5-hydroxy-4-((R)-3-hydroxy-5-phenylpentyl)cyclopenta[b]furan-2-one (15.0 g, 49.3 mmol) and 3,4-dihydro-2H-pyran (12.4 g, 147.4 mmol) in THF (200 mL) at room temperature and the mixture was stirred for 2.5 hr (TLC monitoring). Saturated aqueous solution of sodium bicarbonate (200 mL) was poured into reaction mixture and the reaction was stirred for 5 minutes. The organic layer was separated and the aqueous layer was extracted with ethyl acetate (200 mL). The combined organic layers were dried over magnesium sulfate, the solid was filtered off and the filtrate was concentrated under reduced pressure to give 26.0 g of crude product. The crude product was purified by column chromatography and then concentrated under reduced pressure to provide 22.1 g of the title compound (95.0% yield).

$^1$H-NMR (400 MHz, CDCl$_3$): δ 7.209-7.247 (m, 2H), 7.117-7.171 (m, 3H), 4.892-4.925 (m, 1H), 4.531-4.622 (m, 2H), 3.746-4.046 (m, 3H), 3.604-3.630 (m, 1H), 3.397-3.454 (m, 2H), 1.134-2.765 (m, 26H)

$^{13}$C-NMR (100 MHz, CDCl3): δ177.706 (177.531, 177.425, 177.235), 142.434 (142.403, 142.130, 142.100), 128.369, 128.240, 125.811 (125.689), 98.797 (98.607, 98.152), 97.742 (97.681, 95.692, 95.624), 84.185 (84.155, 84.094, 84.071), 82.887 (82.705), 79.813 (79.677), 76.360 (76.314, 76.086, 76.011), 63.562 (62.948, 62.454, 61.877), 53.277 (52.943), 52.086 (51.623), 42.985 (42.894, 42.484, 42.416), 39.000 (38.924, 36.670, 36.609), 36.093 (36.040, 35.546, 35.508), 33.019 (32.875, 31.751, 31.615), 31.895 (31.258), 31.417 (30.491), 31.334 (31.296, 30.749, 30.719), 28.867 (28.556), 28.677 (28.343), 25.428, 20.517 (20.434, 20.024), 19.402 (19.371, 18.954, 18.916)

Example 25

(3aR,4R,5R,6aS)-4-((3R)-5-phenyl-3-((tetrahydro-2H-pyran-2-yl)oxy)pentyl)-5-((tetrahydro-2H-pyran-2-yl)oxy)hexahydro-2H-cyclopenta[b]furan-2-ol

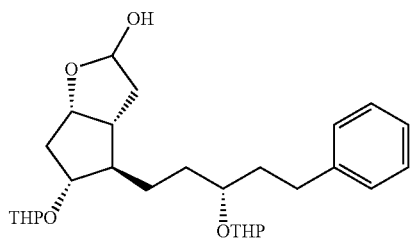

(3aR,4R,5R,6aS)-4-((3R)-5-phenyl-3-((tetrahydro-2H-pyran-2-yl)oxy)pentyl)-5-((tetrahydro-2H-pyran-2-yl)oxy) hexahydro-2H-cyclopenta[b]furan-2-one (22.0 g, 46.6 mmol) was dissolved in toluene (200 mL), followed by cooling to −70° C., and DIBAL (1.0M in hexane, 60 mL, 60.0 mmol) was added dropwisely. Then the reaction was quenched by adding saturated aqueous solution of ammonium chloride (10 mL) at −70° C. The resulting mixture was poured into 200 mL of a 2M sodium bisulfate aqueous solution at room temperature and the stirring was continued for 30 minutes. After separation of the organic layers, toluene (200 mL) was added to the aqueous layer. The combined organic layers were concentrated under reduced pressure to give 30.0 g of crude title compound.

$^1$H-NMR (400 MHz, CDCl3): δ 7.237-7.274 (m, 2H), 7.133-7.205 (m, 3H), 5.410-5.609 (m, 1H), 4.587-4.729 (m, 3H), 3.779-3.935 (m, 3H), 3.603-3.688 (m, 1H), 3.446-3.504 (m, 2H), 1.183-2.833 (m, 26H)

$^{13}$C-NMR (100 MHz, CDCl$_3$): δ142.661 (142.593, 142.297, 142.191), 128.392, 128.262, 125.811 (125.765, 125.682, 125.613), 101.605 (101.537, 101.469, 101.400), 98.182 (97.833, 97.689, 97.499), 96.224 (96.155, 95.973, 95.874), 85.726 (85.460, 85.210, 85.119), 80.967 (80.899, 80.861, 80.557), 76.678 (76.587, 76.420, 76.071), 63.251 (63.137, 62.910, 62.887), 62.310 (62.105, 62.044, 62.006), 53.247 (52.594, 52.564), 51.554 (51.516, 51.433, 51.380), 47.645 (47.304, 45.346, 44.799) 42.142 (42.112, 38.567, 38.545), 41.960 (41.899, 41.095, 41.042), 40.769 (39.562), 36.715 (36.624, 35.417, 35.326), 33.155 (33.133, 33.004), 31.987 (31.918, 31.243, 31.182), 30.871 (30.802, 30.476, 30.385), 29.163 (28.928, 28.624, 28.373), 25.482 (25.436, 25.292), 20.275 (20.206, 20.070, 19.994), 19.523 (19.295, 19.045, 18.931)

Example 26

(Z)-7-((1R,2R,3R,5S)-5-hydroxy-2-((3R)-5-phenyl-3-((tetrahydro-2H-pyran-2-yl)oxy)pentyl)-3-((tetrahydro-2H-pyran-2-yl)oxy)cyclopentyl)hept-5-enoic acid

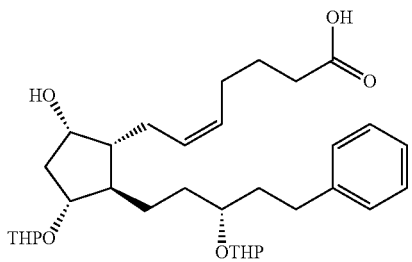

A suspension of (4-carboxybutyl)triphenylphosphonium bromide (84.0 g, 189.5 mmol) and potassium tert-butoxide (44.0 g, 392.1 mmol) in THF (700 mL) was cooled to −20° C. for 30 min. A solution of (3aR,4R,5R,6aS)-4-((3R)-5-phenyl-3-((tetrahydro-2H-pyran-2-yl)oxy)pentyl)-5-((tetrahydro-2H-pyran-2-yl)oxy)hexahydro-2H-cyclopenta[b]furan-2-ol (30 g from Example 25) in THF (50 mL) at −20° C. was added and the reaction mixture was stirred for 16 hr. Then saturated aqueous solution of ammonium chloride (500 mL) was added and the resulting suspension was stirred for 30 min at room temperature. After separation of the organic layers, the aqueous layer was adjusted to have a pH of 6.0 by addition of a 2M sodium bisulfate solution and extracted with ethyl acetate (300 mL). The combined organic layers were dried over magnesium sulfate and concentrated under reduced pressure to give 54.0 g of crude title compound.

$^1$H-NMR (400 MHz, CDCl$_3$): δ 7.248-7.289 (m, 2H), 7.140-7.211 (m, 3H), 5.463-5.577 (m, 1H), 5.314-5.388 (m, 1H), 4.666-4.714 (m, 1H), 4.609-4.641 (m, 1H), 4.084-4.119 (m, 1H), 3.913-4.054 (m, 2H), 3.794-3.874 (m, 1H), 3.665-3.740 (m, 1H), 3.465-3.539 (m, 2H), 2.555-2.834 (m, 2H), 1.311-2.383 (m, 30H)

$^{13}$C-NMR (100 MHz, CDCl3): δ 177.789 (177.364), 142.616 (142.517, 142.327, 142.214), 129.856 (129.788, 129.697, 129.606), 129.226 (129.151, 129.105, 129.037), 128.392, 128.308 (128.293, 128.270), 125.818 (125.780, 125.689, 125.659), 98.895 (98.622), 97.393 (96.914, 96.641, 96.558), 82.796 (82.766, 82.014, 81.992), 77.195 (76.231, 76.086), 74.728 (74.758, 74.675), 63.547 (63.456, 62.818, 62.781), 62.644 (62.598, 62.378, 62.295), 52.040 (51.820), 51.737 (51.463), 49.998 (49.968), 49.869 (49.839), 40.548 (40.510), 36.753 (36.708), 33.338 (33.292, 33.087, 33.019), 32.070 (32.040, 31.744), 31.569 (31.440, 31.326, 31.296), 31.136 (31.098, 30.787), 29.580 (29.375, 28.950, 28.730), 27.341 (27.189, 27.007, 26.871), 26.499 (26.370), 25.444 (25.398), 24.677 (24.563), 20.426 (20.373), 19.326 (19.288)

Example 27

(8aR,9R,10R,11aS,Z)-9-((3R)-5-phenyl-3-((tetrahydro-2H-pyran-2-yl)oxy)pentyl)-10-((tetrahydro-2H-pyran-2-yl)oxy)-4,5,8,8a,9,10,11,11a-octahydrocyclopenta[b]oxecin-2(3H)-one

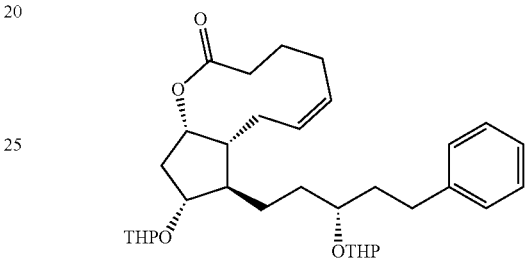

A solution of (Z)-7-((1R,2R,3R,5S)-5-hydroxy-2-((3R)-5-phenyl-3-((tetrahydro-2H-pyran-2-yl)ox y)pentyl)-3-((tetrahydro-2H-pyran-2-yl)oxy)cyclopentyl)hept-5-enoic acid (52 g from Example 26) in xylene (250 mL) was treated with 2,2'-dipyridyl disulfide (28.9 g, 131.2 mmol) and triphenylphosphine (39.2 g, 149.5 mmol). This mixture was then stirred for 2 hr at room temperature under an atmosphere of nitrogen. The resulting mixture was heated to 80° C. for 18 hr (TLC monitoring), followed by removal of xylene under reduced pressure. The residue was diluted with saturated aqueous solution of sodium bicarbonate (200 mL) and extracted with ethyl acetate (200 mL). The organic layer was dried over magnesium sulfate and concentrated under reduced pressure to give 80.0 g of crude product. The crude product was purified by column chromatography providing 17.1 g of the title compound (68.0% yield, 3 steps).

$^1$H-NMR (400 MHz, CDCl$_3$): δ 7.240-7.282 (m, 2H), 7.153-7.218 (m, 3H), 5.245-5.350 (m, 2H), 5.102-5.117 (m, 1H), 4.560-4.695 (m, 2H), 3.890-3.978 (m, 2H), 3.808-3.876 (m, 1H), 3.632-3.715 (m, 1H), 3.442-3.520 (m, 2H), 2.580-2.815 (m, 2H), 1.352-2.507 (m, 30H)

$^{13}$C-NMR (100 MHz, CDCl3): δ 173.873 (173.843, 173.797, 173.759), 142.722 (142.593, 142.464, 142.320), 131.139 (130.995), 128.392 (128.361), 128.300 (128.262), 127.632 (127.837, 127.868), 125.788 (125.727, 125.667, 125.606), 100.413 (100.391, 98.129, 97.871), 97.840 (97.704, 96.504, 96.391), 79.085 (84.231, 84.254), 76.375 (76.542, 76.694), 73.695 (73.582), 63.077 (62.970, 62.932, 62.856), 62.796 (62.758, 62.507, 62.393), 49.110, 44.974 (44.928, 44.609, 44.564), 39.843, 37.224 (37.201), 36.882 (36.814), 36.063, 35.516 (35.440), 32.047 (32.017, 31.956), 31.417 (31.273), 31.076 (30.985, 30.780, 30.711), 27.129, 26.681, 26.552 (26.506), 25.497, 25.428 (25.406), 20.176 (20.100, 20.047), 20.024 (19.850, 19.561, 19.493)

Example 28

(8aR,9R,10R,11aS,Z)-10-hydroxy-9-((R)-3-hydroxy-5-phenylpentyl)-4,5,8,8a,9,10,11,11a-octahydrocyclopenta[b]oxecin-2(3H)-one

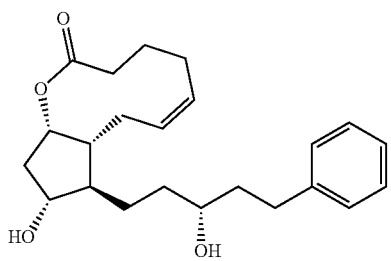 [SMILES: O=C1CCC/C=C\C[C@@H]2[C@@H](CC[C@@H](O)CCc3ccccc3)[C@H](O)C[C@@H]2O1]

p-Toluenesulfonic acid monohydrate (0.34 g, 1.8 mmol) was added to a stirred solution of (8aR,9R,10R,11aS,Z)-9-((3R)-5-phenyl-3-((tetrahydro-2H-pyran-2-yl)oxy)pentyl)-10-((tetrahydro-2H-pyran-2-yl)oxy)-4,5,8,8a,9,10,11,11a-octahydrocyclopenta[b]oxecin-2(3H)-one (17.0 g, 31.4 mmol) in methanol (170 mL). The mixture was stirred for 2 hr at room temperature (TLC monitoring). Then, the reaction mixture was quenched with saturated sodium bicarbonate aqueous solution (200 mL), and the methanol was removed under reduced pressure. The residue was extracted with ethyl acetate (200 mL). The organic layer was separated. The aqueous layer was extracted with ethyl acetate (200 mL). The combined organic layers were dried over magnesium sulfate, filtered and concentrated under reduced pressure to give 16.3 g of crude product. The crude product was purified by column chromatography providing 9.2 g of the product (78.6% yield). The product was crystallized from a mixture of hexane and ethyl acetate to give 8.1 g white crystals (mp 114~118° C.).

The x-ray powder diffraction pattern of crystalline title compound has characteristic peaks expressed in degrees 2θ at approximately 9.0, 10.6, 14.5, 15.1, 17.3, 18.2, 19.6, 21.0, 21.2, 23.4, 27.69, 37.8, 44.1.

Determination of Isomer Content:

Four samples (the product before crystallization, the product of the first crystallization, the filtrate of the first crystallization, and the product of the second crystallization) were hydrolyzed using methanol and 3N NaOH. After 2 h at 25° C., the mixture was acidified and extracted with ethyl acetate. After drying-concentration of the extracts, crude Latanoprost acid was obtained. The crude Latanoprost acid was esterified using $K_2CO_3$ and 2-iodopropane in DMF. After 2 h at 60° C., water and ethyl acetate were added and phase separated, the aqueous layer extracted with ethyl acetate. After drying-concentration of the extracts, crude Latanoprost was obtained. HPLC (Phenomenex Luna 5 µm silica) analysis of the crude product showed the following results:

| Sample | 5,6-trans isomer | 15β-isomer |
| --- | --- | --- |
| Before crystallization | 0.10% | 0.06% |
| After $1^{st}$ crystallzation | 0.01% | not detectable |
| $1^{st}$ filtrate | 0.16% | 0.12% |
| After $2^{nd}$ crystallization | not detectable | not detectable |

$^1$H-NMR (400 MHz, CDCl$_3$): δ 7.239-7.276 (m, 2H), 7.140-7.186 (m, 3H), 5.275-5.338 (m, 1H), 5.190-5.243 (m, 1H), 5.112 (m, 1H), 3.792-3.853 (m, 1H), 3.626 (br s, 1H), 3.477-3.489 (m, 1H), 3.070 (br s, 1H), 2.737-2.810 (m, 2H), 2.603-2.678 (m, 1H), 1.443-2.455 (m, 17H)

$^{13}$C-NMR (100 MHz, CDCl3): δ 173.880, 142.092, 131.162, 128.422, 128.399, 127.648, 125.849, 77.392, 74.083, 71.525, 52.033, 46.165, 40.920, 39.023, 36.100, 34.765, 32.131, 27.827, 27.485, 26.696, 25.428

Example 29

(Z)-7-((1R,2R,3R,5S)-3,5-dihydroxy-2-((R)-3-hydroxy-5-phenylpentyl)cyclopentyl)hept-5-enoic acid

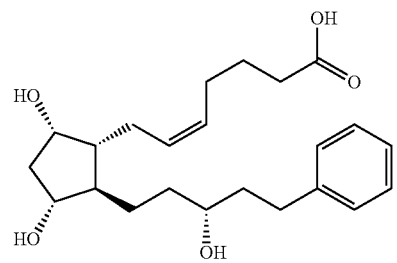 [SMILES: O=C(O)CCC/C=C\C[C@@H]1[C@@H](CC[C@@H](O)CCc2ccccc2)[C@H](O)C[C@@H]1O]

A solution of (8aR,9R,10R,11aS,Z)-10-hydroxy-9-((R)-3-hydroxy-5-phenylpentyl)-4,5,8,8a,9,10,11,11a-octahydrocyclopenta[b]oxecin-2(3H)-one (1.0 g, product after the second crystallization of Example 28) in 10 mL 2-propanol was treated with 3N potassium hydroxide aqueous solution (2.7 mL). This mixture was stirred at 50° C. for 2 hr. The reaction mixture was cooled and further adjusted to have a pH of 8.5±0.2 with 3N hydrochloric acid aqueous solution. Most of the solvent was removed under reduced pressure. The residue was diluted with saturated aqueous solution of sodium bicarbonate (20 mL) and ethyl acetate (20 mL). The mixture was stirred at room temperatures for 5 minutes. The organic phase and the aqueous phase were separately collected. The aqueous layer was adjusted to have a pH of 3.0±0.2 with 3N hydrochloric acid aqueous solution at room temperature and extracted with ethyl acetate (20 mL). The organic layer was dried over magnesium sulfate and concentrated under reduced pressure to give 1.3 g of crude Latanoprost acid.

Determination of Isomer Content of the Product:

A sample of this product was esterified using $K_2CO_3$ and 2-iodopropane in DMF. After 2 h at 60° C., water and ethyl acetate were added and phase separated, the aqueous layer extracted with ethyl acetate. After drying-concentration of the extracts, crude Latanoprost was obtained. HPLC (Phenomenex Luna 51 µm silica) analysis of the crude product showed that no isomer was detectable.

$^1$H-NMR (400 MHz, CDCl$_3$): δ 7.253-7.282 (m, 2H), 7.157-7.194 (m, 3H), 5.455-5.506 (m, 1H), 5.342-5.394 (m, 1H), 4.142-4.152 (m, 1H), 3.936 (m, 1H), 3.664-3.711 (m, 1H), 2.754-2.813 (m, 1H), 2.618-2.678 (m, 1H), 2.327 (t, 2H), 2.241 (t, 2H), 2.133 (q, 2H), 1.496-1.892 (m, 10H), 1.307-1.382 (m, 2H)

$^{13}$C-NMR (100 MHz, CDCl3): δ 177.382, 142.178, 129.555, 129.512, 128.487, 125.902, 78.493, 74.354, 71.477, 52.234, 51.536, 42.396, 38.634, 35.077, 32.923, 31.982, 28.893, 26.490, 26.229, 24.500

Example 30

(Z)-isopropyl 7-((1R,2R,3R,5S)-3,5-dihydroxy-2-((R)-3-hydroxy-5-phenylpentyl)cyclopentyl) hept-5-enoate (Latanoprost)

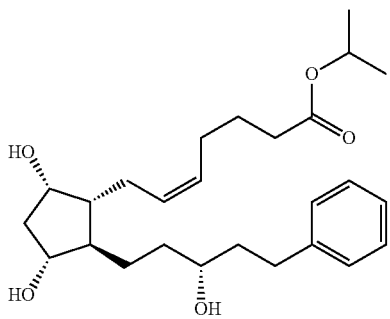 [SMILES: CC(C)OC(=O)CCC/C=C\C[C@@H]1[C@@H](CC[C@@H](O)CCc2ccccc2)[C@H](O)C[C@@H]1O]

A solution of crude Latanoprost acid (1.3 g from Example 29) in DMF (13 mL) was treated with $K_2CO_3$ (1.38 g, 1.0 mmol) and 2-iodopropane (1.13 g, 6.6 mmol). This mixture was then stirred at 80° C. for 2 hr under an atmosphere of nitrogen (TLC monitoring). Water (40 mL) and ethyl acetate (40 mL) were added and the mixture was stirred for 10 min. The aqueous layer was separated and extracted with ethyl acetate (40 mL), and the combined organic layer was dried over magnesium sulfate and concentrated under reduced pressure to give 1.1 g of crude Latanoprost. The crude Latanoprost could be purified by column chromatography and then concentrated under reduced pressure to provide 0.7 g of Latanoprost (60.3% yield, 2 steps; HPLC (Phenomenex Luna 5 m silica) analysis of the product showed that no isomer was detectable).

$^1$H-NMR (400 MHz, $CDCl_3$): δ 7.262-7.293 (m, 2H), 7.165-7.206 (m, 3H), 5.433-5.484 (m, 1H), 5.360-5.411 (m, 1H), 4.993 (heptet, 1H), 4.158 (m, 1H), 3.939 (m, 1H), 3.659 (m, 1H), 2.766-2.824 (m, 3H), 2.089-2.702 (m, 8H), 1.314-1.898 (m, 12H), 1.221 (d, 6H)

$^{13}$C-NMR (100 MHz, $CDCl_3$): δ 173.476, 142.072, 129.590, 129.322, 128.393, 125.806, 78.788, 74.709, 71.292, 67.651, 52.895, 51.883, 42.490, 39.046, 35.793, 34.033, 32.108, 29.631, 26.898, 26.613, 24.913, 21.819

The crude Latanoprost could also be purified via silylation and desilylation as described in Examples 11 and 12. HPLC (Phenomenex Luna 5 μm silica) analysis of the product showed that no isomer or impurity was detectable.

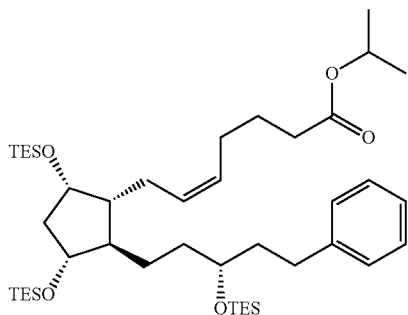

$^1$H-NMR (400 MHz, $CDCl_3$): δ 7.257-7.294 (m, 2H), 7.172-7.190 (m, 3H), 5.422-5.484 (m, 1H), 5.326-5.387 (m, 1H), 5.001 (heptet, 1H), 4.074-4.119 (m, 1H), 3.676-3.769 (m, 2H), 2.578-2.733 (m, 2H), 2.238-2.306 (m, 2H), 2.067-2.191 (m, 4H), 1.586-1.799 (m, 7H), 1.501-1.552 (m, 2H), 1.370-1.437 (m, 3H), 1.222 (d, 6H), 0.932-0.999 (m, 27H), 0.546-0.645 (m, 18H)

$^{13}$C-NMR (100 MHz, $CDCl_3$): δ 173.197, 142.692, 130.122, 128.953, 128.293, 128.278, 125.606, 76.238, 72.352, 71.768, 67.297, 50.264, 48.162, 44.230, 39.121, 34.484, 34.241, 31.728, 28.062, 26.764, 25.846, 25.041, 21.823, 6.991, 6.885, 6.870, 5.177, 4.972, 4.942

Example 31~37 Preparation of Tafluprost and its Intermediates

Example 31

(3aR,4R,5R,6aS)-4-((E)-3,3-difluoro-4-phenoxybut-1-en-1-yl)-5-((tetrahydro-2H-pyran-2-yl)oxy)hexahydro-2H-cyclopenta[b]furan-2-ol

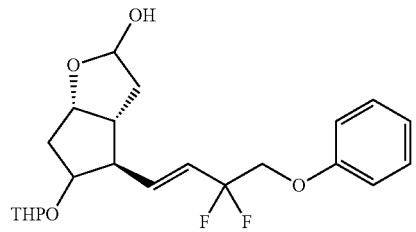

(3aR,4R,5R,6aS)-4-((E)-3,3-difluoro-4-phenoxybut-1-enyl)-hexahydro-5-(tetrahydro-2H-pyran-2-yloxy)cyclopenta[b]furan-2-one (47.0 g, 0.11 mol) was dissolved in toluene (500 mL), followed by cooling to −70° C., and DIBAL (1.0M in Hexane, 172 mL, 0.16 mol) was added dropwisely. Then the reaction was quenched by adding saturated aqueous solution of ammonium chloride (25 mL) at −70° C. The resulting mixture was poured into a 2M sodium bisulfate aqueous solution (500 mL) at room temperature and stirring was continued for 30 minutes. After separation of the organic layers, 500 mL of toluene was added to the aqueous layer. The combined organic layers were concentrated under reduced pressure to give 48 g of crude title compound.

$^1$H-NMR (400 MHz, $CDCl_3$): δ 7.266-7.316 (m, 2H), 6.971-7.010 (m, 1H), 6.892-6.914 (m, 2H), 6.078-6.222 (m, 1H), 5.736-5.912 (m, 1H), 5.516-5.644 (m, 1H), 4.517-4.699 (m, 2H), 4.139-4.211 (m, 2H), 3.725-4.064 (m, 2H), 3.398-3.493 (m, 1H), 3.339 (br s, 1H), 2.337-2.554 (m, 2H), 1.905-2.112 (m, 3H), 1.353-1.808 (m, 7H)

$^{13}$C-NMR (100 MHz, $CDCl_3$): δ 157.963 (157.895), 138.050, 129.576, 123.617, 121.826, 118.220 (t), 114.706, 101.028 (100.899), 99.821 (95.935), 83.168 (83.009), 80.291 (79.935), 69.498 (t), 62.401 (61.665), 54.386 (53.733), 45.733 (44.951), 38.932 (38.818), 36.693, 30.613 (30.461), 25.337 (25.315), 19.485 (18.779)

Example 32

(Z)-7-((1R,2R,3R,5S)-2-((E)-3,3-difluoro-4-phenoxybut-1-en-1-yl)-5-hydroxy-3-((tetrahydro-2H-pyran-2-yl)oxy)cyclopentyl)hept-5-enoic acid

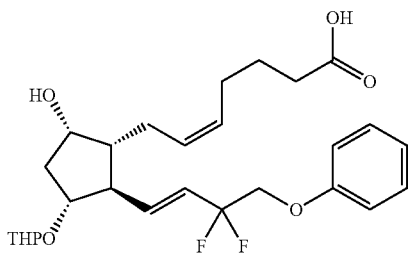

A suspension of (4-carboxybutyl)triphenylphosphonium bromide (198.0 g, 0.45 mol.) and potassium-tert butoxide (102.0 g, 0.91 mol.) in THF (1 L) was cooled to −20° C. for 30 min, and a solution of (3aR,4R,5R,6aS)-4-((E)-3,3-difluoro-4-phenoxybut-1-en-1-yl)-5-((tetrahydro-2H-pyran-2-yl)oxy)hexahydro-2H-cyclopenta[b]furan-2-ol (48.0 g from example 31) in THF (100 mL) at −20° C. was added and the reaction mixture was stirred for 3 hr. Then saturated aqueous solution of ammonium chloride (600 mL) was added and the resulting suspension was stirred for 30 min at room temperature. After separation of the organic layers, the aqueous layer was adjusted to a pH of 6.0 by addition of a 2M sodium bisulfate solution and extracted with ethyl acetate (600 mL). The combined organic layers were dried over magnesium sulfate and concentrated under reduced pressure to give 145.0 g of crude title compound.

Determination of Isomer Content of the Product:

A sample of this product was esterified using $K_2CO_3$ and 2-iodopropane in DMF. After 4 h at 60° C., water and ethyl acetate were added and phase separated, the aqueous layer was extracted with ethyl acetate. After drying-concentration of the extracts, crude 11-protected Tafluprost was obtained. The crude 11-protected Tafluprost was deprotected using 3N HCl in THF and water. After 1 h at 25° C., saturated aqueous solution of sodium bicarbonate was added and extracted with ethyl acetate. After drying-concentration of the extracts, crude Tafluprost was obtained. HPLC (Phenomenex Luna 5 μm silica) analysis of the crude product showed that 2.8% 5,6-trans isomer was found.

$^1$H-NMR (400 MHz, CDCl$_3$): δ 7.244-7.302 (m, 2H), 6.941-6.984 (m, 1H), 6.879-6.901 (m, 2H), 6.085-6.187 (m, 1H), 5.730-5.875 (m, 1H), 5.305-5.435 (m, 2H), 4.608-4.651 (m, 1H), 4.034-4.195 (m, 3H), 3.739-3.853 (m, 1H), 3.378-3.458 (m, 1H), 2.500-2.670 (m, 1H), 2.226-2.331 (m, 4H), 2.071-2.176 (m, 3H), 1.399-1.783 (m, 12H)

$^{13}$C-NMR (100 MHz, CDCl3): δ 177.516 (177.448), 157.971 (157.926), 138.983 (dt), 129.568, 128.619, 128.498, 123.754 (t), 121.780 (121.750), 118.235 (t), 114.706, 98.387 (96.467), 82.174 (80.868), 72.800, 69.528 (t), 62.743 (61.558), 52.405, 49.907, 41.528, 33.444, 26.544, 25.724, 25.550, 25.337, 24.639, 18.893

Example 33

(8aR,9R,10R,11aS,Z)-9-((E)-3,3-difluoro-4-phenoxybut-1-en-1-yl)-10-((tetrahydro-2H-pyran-2-yl)oxy)-4,5,8,8a,9,10,11,11a-octahydrocyclopenta[b]oxecin-2(3H)-one

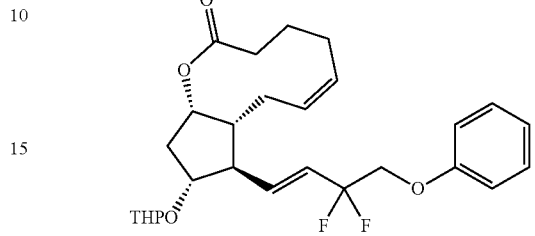

A solution of (Z)-7-((1R,2R,3R,5S)-2-((E)-3,3-difluoro-4-phenoxybut-1-en-1-yl)-5-hydroxy-3-((tetrahydro-2H-pyran-2-yl)oxy)cyclopentyl)hept-5-enoic acid (145.0 g from Example 32) in xylene (2 L) was treated with 2,2'-dipyridyl disulfide (90.0 g, 0.41 mol.) and triphenylphosphine (123.0 g, 0.47 mol.). This mixture was then stirred for 1 hr at room temperature under an atmosphere of nitrogen. The resulting mixture was heated to 80° C. for 18 hr (TLC monitoring), followed by removal of xylene under reduced pressure. The residue was diluted with saturated aqueous solution of sodium bicarbonate (1.6 L) and extracted with ethyl acetate (1.6 L). The organic layer is dried over magnesium sulfate and concentrated under reduced pressure to give 322.0 g of crude product. The crude product was purified by column chromatography providing 26.0 g of the title compound (48% yield, 3 steps).

Determination of Isomer Content of the Product:

A sample of this product was hydrolyzed using methanol and 3N NaOH. After 2 h at 25° C., the mixture was acidified and extracted with ethyl acetate. After drying-concentration of the extracts, crude 11-protected Tafluprost acid was obtained. The crude 11-protected Tafluprost acid was esterified using $K_2CO_3$ and 2-iodopropane in DMF. After 2 h at 60° C., water and ethyl acetate were added and phase separated, the aqueous layer was extracted with ethyl acetate. After drying-concentration of the extracts, crude 11-protected Tafluprost was obtained. The crude 11-protected Tafluprost was deprotected using 3N HCl in THF and water. After 1 h at 25° C., saturated aqueous solution of sodium bicarbonate was added and phase separated, the aqueous layer was extracted with ethyl acetate. After drying-concentration of the extracts, crude Tafluprost was obtained. HPLC (Phenomenex Luna 5 μm silica) analysis of the crude product showed that 0.4% 5,6-trans isomer was found and HPLC (Chiralcel OD-H) analysis of the crude product showed that 0.1% enantiomer was found.

$^1$H-NMR (400 MHz, CDCl$_3$): δ 7.257-7.306 (m, 2H), 6.984 (t, 1H), 6.89 (d, 2H), 6.061-6.157 (m, 1H), 5.816-5.974 (m, 1H), 5.315-5.371 (m, 1H), 5.247-5.305 (m, 2H), 4.589-4.632 (m, 1H), 4.141-4.247 (m, 2H), 3.893-4.047 (m, 1H), 3.733-3.822 (m, 1H), 3.374-3.456 (m, 1H), 2.536-2.672 (m, 2H), 2.334-2.416 (m, 3H), 2.179-2.253 (m, 1H), 2.051-2.108 (m, 1H), 1.330-1.895 (m, 11H)

$^{13}$C-NMR (100 MHz, CDCl$_3$): δ 173.546 (173.448), 157.956 (157.888), 137.872 (t), 131.572, 129.568, 127.048, 124.930 (t), 121.811, 118.061 (t), 114.691, 99.388 (96.117), 81.172 (78.204), 72.451 (72.010), 69.544 (t), 62.629, 61.308, 44.852, 37.816, 36.040, 30.643, 30.529, 26.734 (26.529), 25.383, 25.322, 18.726

Example 34

(8aR,9R,10R,11aS,Z)-9-((E)-3,3-difluoro-4-phenoxybut-1-en-1-yl)-10-hydroxy-4,5,8,8a,9,10,11,11a-octahydrocyclopenta[b]oxecin-2(3H)-one

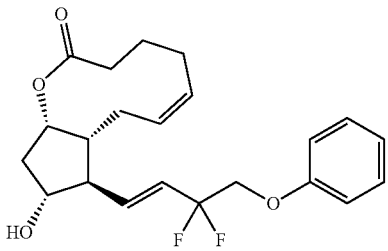 [SMILES: O=C1CCC/C=C\C[C@@H]2[C@@H](/C=C/C(F)(F)COc3ccccc3)[C@H](O)C[C@@H]2O1]

p-toluenesulfonic acid monohydrate (10.37 g, 54.5 mmol) was add to a stirred solution of (8aR,9R,10R,11aS,Z)-9-((E)-3,3-difluoro-4-phenoxybut-1-en-1-yl)-10-((tetrahydro-2H-pyran-2-yl)oxy)-4,5,8,8a,9,10,11,11a-octahydrocyclopenta[b]oxecin-2(3H)-one (26.0 g from example 33) in methanol (200 mL). The mixture was stirred for 2 hr at room temperature (TLC monitoring). Then, the reaction mixture was quenched with saturated sodium bicarbonate aqueous solution (300 mL), and the methanol was removed under reduced pressure. The residue was extracted with ethyl acetate (200 mL). The organic layer was separated. The aqueous layer was extracted with ethyl acetate (200 mL). The combined organic layers were dried over magnesium sulfate, filtered and concentrated under reduced pressure to give 30.0 g of crude product. The crude product was purified by column chromatography providing 20.0 g of the titled compound (90.0% yield).

$^1$H-NMR (400 MHz, CDCl$_3$): δ 7.273-7.313 (m, 2H), 6.976-7.018 (m, 1H), 6.894-6.919 (m, 2H), 6.050-6.100 (m, 1H), 5.836-5.931 (m, 1H), 5.305-5.373 (m, 1H), 5.214-5.233 (m, 2H), 4.206 (t, 2H), 3.901-3.961 (m, 1H), 2.536-2.612 (m, 1H), 2.340-2.453 (m, 4H), 2.176-2.238 (m, 3H), 1.787-1.932 (m, 3H), 1.620-1.723 (m, 2H)

$^{13}$C-NMR (100 MHz, CDCl$_3$): δ 173.463, 157.880, 137.492 (t), 131.633, 129.743, 127.018, 125.378 (t), 121.902, 118.023 (t), 114.767, 76.094, 72.246, 69.399 (t), 55.843, 45.649, 40.594, 36.040, 26.734, 26.582, 25.322

Example 35

(6Z,8aR,9R,10R,11aS)-9-((E)-3,3-difluoro-4-phenoxybut-1-enyl)-2,3,4,5,8,8a,9,10,11,11a-decahydro-2-oxocyclopenta[b]oxecin-10-yl 4-phenylbenzoate

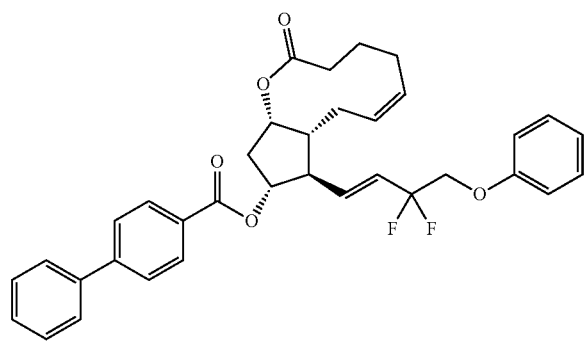 [SMILES: O=C1CCC/C=C\C[C@@H]2[C@@H](/C=C/C(F)(F)COc3ccccc3)[C@H](OC(=O)c3ccc(-c4ccccc4)cc3)C[C@@H]2O1]

A solution of (8aR,9R,10R,11aS,Z)-9-((E)-3,3-difluoro-4-phenoxybut-1-en-1-yl)-10-hydroxy-4,5,8,8a,9,10,11,11a-octahydrocyclopenta[b]oxecin-2(3H)-one (20.0 g, from Example 34) in THF (200 mL) was treated with triethylamine (20.6 g, 0.20 mol), 4-(dimethylamino)pyridine (0.62 g, 5.09 mmol) and biphenyl-4-carbonyl chloride (33.0 g, 0.15 mol). This mixture was then stirred for 18 hr at room temperature under an atmosphere of nitrogen. Saturated aqueous solution of sodium bicarbonate (200 mL) was poured into the reaction mixture and the resulting mixture was stirred for 5 minutes. The organic layer was separated and the aqueous layer was extracted with ethyl acetate (400 mL). The combined organic layers were dried over magnesium sulfate, the solid was filtered off and filtrate was concentrated under reduced pressure to give 40.0 g of crude product. The crude product was purified by column chromatography and then concentrated under reduced pressure to provide 20.0 g of the title compound (69.0% yield). The residue was crystallized from methanol to give white crystalline compound (mp 105~109° C.). The x-ray powder diffraction pattern of crystalline title compound has characteristic peaks expressed in degrees 2θ at approximately 5.0, 6.2, 7.6, 9.5, 10.1, 11.5, 12.6, 13.7, 15.2, 18.0, 19.4, 21.2, 23.1, 23.6, 24.4, 25.7, 28.0, 37.9, 44.1.

Determination of Isomer Rate of the Product:

Four samples (the product before crystallization, the product of the first crystallization, the filtrate of the first crystallization, and the product of the second crystallization) were hydrolyzed using methanol and 3N NaOH. After 2 h at 25° C., the mixture was acidified and extracted with ethyl acetate. After drying-concentration of the extracts, crude Latanoprost acid was obtained. The crude Latanoprost acid was esterified using K$_2$CO$_3$ and 2-iodopropane in DMF. After 2 h at 60° C., water and ethyl acetate were added and phase separated, the aqueous layer was extracted with ethyl acetate. After drying-concentration of the extracts, crude Latanoprost was obtained. HPLC (Phenomenex Luna 5 μm silica and Chiralcel OD-H) analysis of the crude product showed the following results:

| Sample | 5,6-trans isomer | enantiomer |
| --- | --- | --- |
| before crystallization | 0.44% | 0.1% |
| After 1$^{st}$ crystallization | 0.03% | not detectable |
| 1$^{st}$ filtrate | 0.87% | 0.17% |
| After 2$^{nd}$ crystallization | not detectable | not detectable |

$^1$H-NMR (400 MHz, CDCl$_3$): δ 8.055 (d, 2H), 67.601 (d, 4H), 67.477 (t, 2H), 67.389-7.425 (m, 1H), 7.206-7.258 (m, 2H), 6.948 (t, 1H), 6.832 (d, 2H) 6.161-6.222 (m, 1H), 5.890-5.984 (m, 1H), 5.380-5.424 (m, 1H), 5.321-5.371 (m, 2H), 5.166-5.224 (m, 1H), 4.126-4.199 (m, 2H), 2.805-2.882 (m, 2H), 2.394-2.507 (m, 3H), 2.154-2.296 (m, 2H), 1.949-1.991 (m, 3H), 1.802-1.855 (m, 1H), 1.647-1.769 (m, 1H)

$^{13}$C-NMR (100 MHz, CDCl$_3$): δ 173.401, 166.042, 157.833, 145.780, 139.924, 136.440 (t), 131.856, 130.099, 129.541, 128.941, 128.634, 128.205, 127.279, 127.044, 126.763, 125.628 (t), 121.738, 118.000 (t), 114.668, 77.779, 72.416, 69.452 (t), 52.811, 44.997, 38.404, 36.040, 26.818, 26.666, 25.444

Example 36

(Z)-7-((1R,2R,3R,5S)-2-((E)-3,3-difluoro-4-phenoxybut-1-en-1-yl)-3,5-dihydroxy cyclopentyl)hept-5-enoic acid (Tafluprost acid)

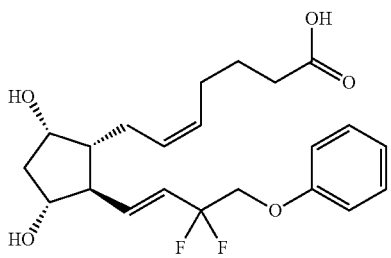 [SMILES: O=C(O)CCC/C=C\C[C@@H]1[C@@H](/C=C/C(F)(F)COc2ccccc2)[C@H](O)C[C@@H]1O]

A solution of (6Z,8aR,9R,10R,11aS)-9-((E)-3,3-difluoro-4-phenoxybut-1-enyl)-2,3,4,5,8,8a,9,10,11,11a-decahydro-2-oxocyclopenta[b]oxecin-10-yl 4-phenylbenzoate (10.0 g from Example 35) in methanol (60 mL) and THF (160 mL) was treated with 3N sodium hydroxide aqueous solution (80 mL). This mixture was stirred at room temperature under an atmosphere of nitrogen for 2 hr. The reaction mixture was further adjusted to a pH of 8.5±0.2 with 3N hydrochloric acid aqueous solution and most of solvent was removed under reduced pressure. The residue was diluted with saturated aqueous solution of sodium bicarbonate (200 mL) and ethyl acetate (200 mL). The mixture was stirred at room temperatures for 5 minutes. The organic phase and the aqueous phase were separately collected. The aqueous layer was adjusted to a pH of 3.0±0.2 with 3N hydrochloric acid aqueous solution at room temperature and extracted with ethyl acetate (200 mL). The organic layer was dried over magnesium sulfate and concentrated under reduced pressure to give 12 g of crude Tafluprost acid.

Determination of Isomer Content of the Product:

A sample of this product was esterified using $K_2CO_3$ and 2-iodopropane in DMF. After 2 h at 60° C., water and ethyl acetate were added and the mixture was extracted with ethyl acetate. After drying-concentration of the extracts, crude Tafluprost was obtained. HPLC (Phenomenex Luna 5 μm silica) analysis of the crude product showed that no isomer was detectable, and HPLC (Chiralcel OD-H) analysis of the crude product showed that no enantiomer was detectable.

$^1$H-NMR (400 MHz, CDCl$_3$): δ 7.264-7.311 (m, 2H), 6.972-7.014 (m, 1H), 6.897-6.926 (m, 2H), 6.054-6.127 (m, 1H), 5.750-5.845 (m, 1H), 5.324-5.417 (m, 2H), 4.149-4.218 (m, 3H), 4.029 (m, 1H), 2.435-2.495 (m, 1H), 2.279-2.370 (m, 3H), 2.014-2.194 (m, 4H), 1.819-1.850 (m, 1H), 1.562-1.728 (m, 3H)

$^{13}$C-NMR (100 MHz, CDCl$_3$): δ 177.972, 157.926, 138.547 (t), 129.910, 129.606, 128.779, 123.723 (t), 121.826, 118.167 (t), 114.774, 77.863, 73.324, 69.437 (t), 55.532, 50.393, 42.788, 32.935, 26.377, 25.694, 24.427

Example 37

(Z)-isopropyl 7-((1R,2R,3R,5S)-2-((E)-3,3-difluoro-4-phenoxybut-1-en-1-yl)-3,5-dihydroxy cyclopentyl)hept-5-enoate (Tafluprost)

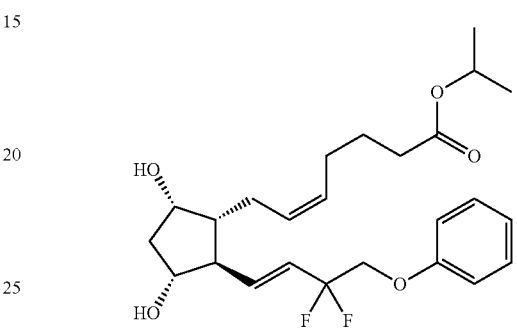

A solution of crude Tafluprost acid (12.0 g from Example 36) in DMF (100 mL) was treated with $K_2CO_3$ (21.1 g, 0.12 mol.) and 2-iodopropane (11.4 g, 0.08 mol.). This mixture was then stirred at 80° C. for 2 hr under an atmosphere of nitrogen (TLC monitoring). Water (100 mL) and ethyl acetate (100 mL) was added and the mixture was stirred for 10 min. The aqueous layer was separated and extracted with ethyl acetate (100 mL), the combined organic layer was dried over magnesium sulfate and concentrated under reduced pressure to give 14.0 g of crude Tafluprost. The crude Tafluprost was purified by column chromatography and then concentrated under reduced pressure to provide 6.8 g of Tafluprost (86% yield, 2 steps). HPLC (Phenomenex Luna 5 μm silica) analysis of the crude product showed that no isomer was detectable, and HPLC (Chiralcel OD-H) analysis of the crude product showed that no enantiomer was detectable.

$^1$H-NMR (400 MHz, CDCl$_3$): δ 7.293 (dd, 2H), 6.994 (t, 1H), 6.912 (d, 2H), 6.101 (dd, 1H), 5.795 (dt, 1H), 5.346-5.421 (m, 2H), 4.994 (heptet, 1H), 4.170-4.216 (m, 3H), 4.019 (m, 1H), 2.603 (m, 1H), 2.446-2.462 (m, 2H), 2.270-2.354 (m, 1H), 2.256 (t, 2H), 2.030-2.146 (m, 4H), 1.839 (d, 1H), 1.572-1.688 (m, 3H), 1.220 (d, 6H)

$^{13}$C-CMR (100 MHz, CDCl$_3$): δ 173.456, 157.949, 138.630 (t), 130.079, 129.581, 128.601, 123.567 (t), 121.793, 118.144 (t), 114.767, 77.910, 73.234, 69.461 (t), 67.656, 55.712, 50.507, 42.944, 33.966, 26.597, 25.703, 24.808, 21.812, 21.789

The crude Tafluprost could also be purified via silylation and desilylation as described in Examples 11 and 12. HPLC (Phenomenex Luna 5 μm silica) analysis of the crude product showed that no isomer or impurity was detectable, and HPLC (Chiralcel OD-H) analysis of the crude product showed that no enantiomer was detectable.

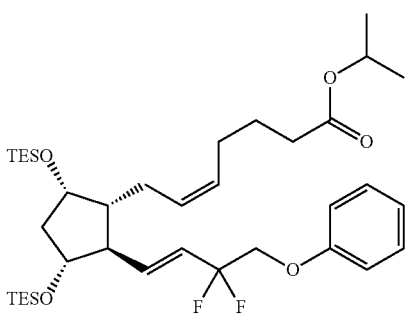

¹H-NMR (400 MHz, CDCl₃): δ7.257-7.304 (m, 2H), 6.962-6.999 (m, 1H), 6.898-6.923 (m, 2H), 6.003-6.076 (m, 1H), 5.757-5.852 (m, 1H), 5.389-5.452 (m, 1H), 5.267-5.330 (m, 1H), 4.985 (heptet, 1H), 4.088-4.226 (m, 3H), 3.837-3.892 (m, 1H), 2.495-2.519 (m, 1H), 2.163-2.308 (m, 4H), 1.985-2.100 (m, 3H), 1.594-1.740 (m, 3H), 1.461-1.512 (m, 1H), 1.21 (d, 6H), 10.887-0.991 (m, 18H), 0.498-0.616 (m, 12H)

¹³C-NMR (100 MHz, CDCl₃): δ 173.106, 158.070, 139.329 (t), 129.500, 129.333, 129.211, 124.179 (t), 121.644, 118.152 (t), 114.699, 76.428, 71.623, 69.544 (t), 67.312, 54.469, 49.323, 45.087, 34.112, 26.704, 25.049, 24.859, 21.793, 6.847, 6.688, 4.988, 4.745

Examples 38~45 Preparation of Isopropyl Unoprostone and its Intermediates

Example 38

(3aR,4R,5R,6aS)-4-[3-(tert-butyldimethylsilyloxy)decyl)-5-(tetrahydro-2H-pyran-2-yloxy)hexahydro-2H-cyclopenta[b]furan-2-ol

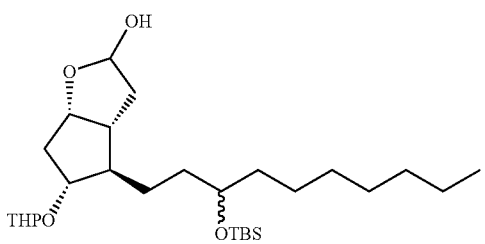

A solution of (3aR,4R,5R,6aS)-4-(3-(tert-butyldimethyl-silyloxydecyl)-5-(tetrahydro-2H-pyran-2-yloxy)-hexahydro-2H-cyclopenta[b]furan-2-one (29 g, 58.4 mmol) in 300 ml toluene was cooled to −70° C. and followed by dropwise addition of diisobutylaluminium hydride (88 ml, 20% in Hexane). The reaction mixture was quenched with 10 ml saturated ammonium chloride and 150 ml 2M NaHSO₄ while stirring for 30 minutes. Then, the mixture was phase separated and the aqueous layer was extracted with toluene. The organic layers were dried over anhydrous MgSO₄ and concentrated under reduced pressure to give 32 g of crude product.

¹H-NMR (CDCl₃): δ 4.972~5.616 (m, 1H), 4.606~4.754 (m, 2H), 3.501~4.057 (m, 4H), 1.177~2.300 (m, 28H), 0.826~0.952 (m, 12H), 0.595 (m, 1H), −0.037~0.031 (m, 6H)

¹³C-NMR (CDCl₃): δ 106.060 (105.909, 104.649, 104.064, 102.273), 100.550 (100.459, 100.147, 99.981), 90.310 (89.976, 89.916, 89.536, 89.437, 88.952, 88.899), 87.009 (86.014, 85.513, 85.445, 85.377, 84.314), 76.929 (76.845, 76.731, 76.640, 76.541, 76.496, 76.329), 66.735 (66.332, 66.211, 65.976), 58.120 (57.254, 56.123, 55.721, 52.343, 52.207, 51.987, 51.888, 49.870, 49.687, 49.322, 49.186), 46.734 (46.688, 46.620), 45.474 (45.277, 43.994, 42.954), 41.671 (41.565, 41.474, 41.079), 40.707, 39.584 (39.546, 39.493, 39.371), 36.244, 35.273 (35.181, 34.885, 34.825, 34.627), 34.225 (34.195, 34.104), 33.716, 33.307 (33.223, 33.079, 32.973), 30.331, 29.891 (29.800, 29.724, 29.640, 29.602, 29.352), 28.206, 24.320 (23.591, 23.500, 23.356), 22.490, 18.521, 11.386 (9.518), 0.053

Example 39

(Z)-7-[(1R,2R,3R,5S)-2-(3-(tert-butyldimethylsily-loxy)decyl)-5-hydroxy-3-(tetrahydro-2H-pyran-2-yloxy)cyclopentyl)hept-5-enoic acid

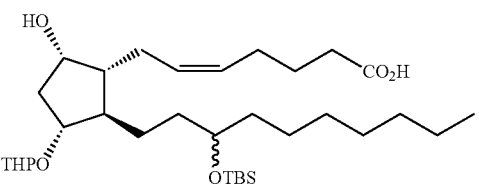

A suspension of (4-carboxybutyl)triphenylphosphonium bromide (102 g, 0.23 mol) and potassium tert-butoxide (52 g, 0.46 mol) in THF (700 mL) was cooled to −20° C. in 1-liter round-bottom flask, and a solution of (3aR,4R,5R,6aS)-4-[3-(tert-butyldimethyl-silyloxy)-decyl)-5-(tetra-hydro-2H-pyran-2-yloxy)hexahydro-2H-cyclopenta[b]furan-2-ol (32 g from example 38) in 150 ml tetrahydrofuran at −20° C. was added into the flask and the reaction mixture was stirred for 4 hours. Then saturated aqueous solution of ammonium chloride (300 mL) was added and the resulting suspension was stirred for 30 min at room temperature. Then, the mixture was phase separated and the aqueous layer was adjusted to a pH of 6.0 with 2M sodium bisulfate solution and extracted with 300 ml ethyl acetate. The organic layers were combined and dried over anhydrous MgSO₄. The solid was filtered off and organic solvent was evaporated off under vacuum to obtain 61 g crude product.

¹H-NMR (CDCl₃): δ 5.238~5.449 (m, 2H), 4.590~4.662 (m, 1H), 4.067 (m, 1H), 3.803~3.936 (m, 2H), 3.403~3.531 (m, 2H), 1.897~2.145 (m, 8H), 1.227~1.859 (m, 26H), 0.844~0.919 (m, 12H), 0.529~0.568 (m, 1H), 0.00 (m, 6H)

¹³C-NMR (CDCl₃): δ 172.165, 135.337 (133.272), 133.044 (132.923), 101.506 (101.400, 100.808, 100.717), 87.441 (87.312, 86.401, 84.815), 79.289 (79.213), 77.004 (76.860, 76.769), 67.114 (67.061, 66.575, 66.477), 56.298 (56.222, 55.964, 55.941, 54.476, 54.431, 54.385, 54.332), 44.988 (44.927), 42.870, 41.550 (41.512, 41.466, 41.428), 39.766 (39.667, 39.667, 39.607), 37.959, 35.274, 35.569 (35.181), 34.233 (34.217), 34.043 (33.876), 33.747 (33.663), 31.849 (31.758, 31.538, 31.485), 30.992, 30.346, 29.853 (29.807, 29.732), 29.193, 27.098, 24.077 (24.024, 23.614, 23.533), 22.612 (22.566), 18.543, 11.401 (9.518), 0.038

Example 40

(8aR,9R,10R,11aS,Z)-9-[3-(tert-butyldimethylsilyloxy)decyl]-10-(tetrahydro-2H-pyran-2-yloxy)-4,5,8,8a,9,10,11,11a-octahydrocyclo-penta[b]oxecin-2(3H)-one

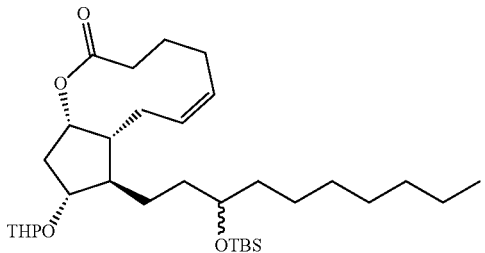

A solution of (Z)-7-[(1R,2R,3R,5S)-2-(3-(tert-butyldimethyl-silyloxy)decyl)-5-hydroxy-3-(tetrahydro-2H-pyran-2-yloxy)cyclopentyl)hept-5-enoic acid (61 g from Example 39) in 250 mL xylene was treated with 2,2'-dipyridyl disulfide (36 g, 0.17 mol) and triphenylphosphine (38 g, 0.43 mol). This mixture was then stirred for 1 hour at room temperature under an atmosphere of nitrogen and the resulting mixture was heated to 80° C. for 18 hours. Then, the xylene was removed under reduced pressure, and the residue was diluted with 200 ml saturated sodium bicarbonate aqueous solution and extracted with 200 ml ethyl acetate twice. The organic layer was dried over anhydrous MgSO$_4$. The solid was filtered off and organic solvent was evaporated off under vacuum. The crude product was purified by chromatography on silica gel using a mixture of hexane and ethyl acetate as a gradient eluent. Yield of the title compound was 25 g (75% in 3 steps).

$^1$H-NMR (CDCl$_3$): δ 5.246~5.388 (m, 2H), 5.098 (m, 1H), 4.589 (m, 1H), 3.459~3.918 (m, 4H), 1.249~2.477 (m, 33H), 0.867~1.021 (m, 12H), 0.579 (q, 1H), 0.026 (m, 6H)

$^{13}$C-NMR (CDCl$_3$): δ 173.751 (173.683), 131.033, 127.709 (127.769), 100.459 (100.391, 96.110, 96.011), 84.246 (83.874, 78.857, 78.599), 73.528, 72.823 (72.716, 72.572, 72.443), 62.758 (62.151, 62.006), 49.399, 44.928 (44.769, 44.640, 44.435), 39.873 (39.835), 37.178 (37.140), 37.042 (37.011), 36.017, 34.059 (34.013), 33.884 (33.839), 31.812, 31.030, 30.886, 29.831 (29.800), 29.300, 27.288 (27.216), 26.848 (26.658, 26.597), 25.907, 25.504 (25.428, 25.353, 25.254, 25.193), 22.635, 19.850 (19.311, 19.182), 18.111, 14.073, −4.409

Example 41

(8aR,9R,10R,11aS,Z)-9-(3-hydroxydecyl)-10-(tetrahydro-2H-pyran-2-yloxy)-4,5,8,8a,9,10,11,11a-octahydrocyclopenta[b]oxecin-2(3H)-one

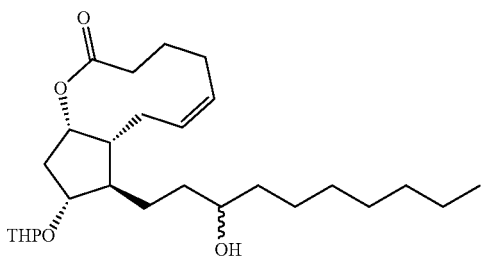

A solution of (8aR,9R,10R,11aS,Z)-9-[3-(tert-butyldimethylsilyloxy)decyl]-10-(tetrahydro-2H-pyran-2-yloxy)-4,5,8,8a,9,10,11,11a-octahydrocyclo-penta[b]oxecin-2(3H)-one (25 g, 44 mmol) in 350 ml tetrahydrofuran and 49 ml TBAF (1M in tetrahydrofuran) were added into 1-liter round-bottom flask. The reaction mixture was stirred at 50° C. for 3 hours and quenched by 200 ml saturated NaHCO$_3$ aqueous solution. Then, the mixture was phase separated and the aqueous layer was extracted with ethyl acetate. The organic layers were combined and dried over anhydrous MgSO$_4$. The solid was filtered off and organic solvent was evaporated off under vacuum. The crude product was purified by chromatography on silica gel using a mixture of hexane and ethyl acetate as a gradient eluent. Yield of the titled compound was 15 g (75%).

$^1$H-NMR (CDCl$_3$): δ 5.243~5.322 (m, 2H), 5.109 (m, 1H), 4.565~4.621 (m, 1H), 3.475~3.947 (m, 3H), 1.275~2.470 (m, 36H), 0.872 (m, 3H)

$^{13}$C-NMR (CDCl$_3$): δ173.797 (173.721), 131.132, 127.655, 100.322 (100.338, 97.408, 96.922), 84.489 (84.413, 79.950, 79.358), 73.361, 72.185 (72.020, 71.995, 71.692), 63.236 (62.834, 62.720), 48.693, 45.383 (44.966, 44.860), 39.865 (39.812), 37.717 (37.679), 37.459 (37.429), 36.017, 34.552 (34.499, 34.324, 33.960), 31.804, 31.129 (31.038, 30.985), 29.702 (29.664, 29.292), 28.085, 27.508, 27.113, 26.817 (26.660), 25.687 (25.633), 25.375, 22.643, 19.994 (19.736), 14.088

Example 42

(8aR,9R,10R,11aS,Z)-9-(3-oxodecyl)-10-(tetrahydro-2H-pyran-2-yloxy)-4,5,8,8a,9,10,11,11a-octahydrocyclopenta[b]oxecin-2(3H)-one

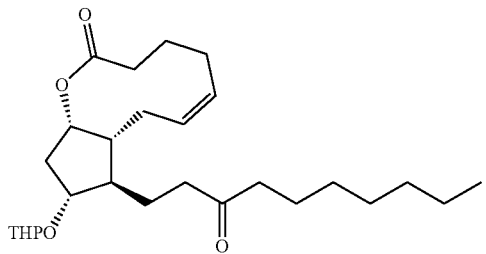

(8aR,9R,10R,11aS,Z)-9-[3-hydroxy)decyl) 10-(tetrahydro-2H-pyran-2-yloxy)-4,5,8,8a,9,10,11,11a-octahydrocyclopenta[b]oxecin-2(3H)-one (15 g, 33 mmol) was dissolved in 150 ml toluene in 1-liter round-bottom flask. Subsequently, (2,2,6,6-tetramethyl-piperidin-1-yl)oxyl (1.05 g, 6.7 mmol), potassium bromide (3.96 g, 33 mmol), 72 ml of 3% NaHCO$_3$ aqueous solution and 26 ml of 12% NaOCl aqueous solution was added into the flask at 0° C., followed by addition of 300 ml water and 300 ml ethyl acetate. The reaction mixture was stirred for 10 minutes. Then, the mixture was phase separated and the aqueous layer was extracted with ethyl acetate. The organic layers were combined and dried over anhydrous MgSO$_4$. The solid was filtered off and organic solvent was evaporated off under vacuum. The crude product was purified by chromatography on silica gel using a mixture of hexane and ethyl acetate. Yield of the titled compound was 14 g (94%).

$^1$H-NMR (CDCl$_3$): δ 5.184~5.263 (m, 2H), 5.055 (s, 1H), 4.475~4.528 (m, 1H), 3.413~3.3.885 (m, 3H), 2.609 (t, 1H), 1.974~2.537 (m, 11H), 1.474~1.817 (m, 13H), 1.213 (m, 8H), 0.813 (m, 3H)

$^{13}$C-NMR (CDCl$_3$): δ 211.400 (211.020), 173.653 (173.546), 131.124, 127.526, 100.330 (97.013), 84.762, 70.502, 63.031 (62.781), 45.141, 44.738, 42.924 (42.879), 40.169 (39.994, 39.843), 37.285, 31.615, 31.129 (31.114), 29.193 (29.163), 29.026, 26.969, 26.620, 25.580, 25.444 (25.406), 25.337, 33.834, 22.544

Example 43

(8aR,9R,10R,11aS,Z)-9-(3-oxodecyl)-10-hydroxy)-4,5,8,8a,9,10,11,11a-octa-hydrocyclopenta[b]oxecin-2(3H)-one

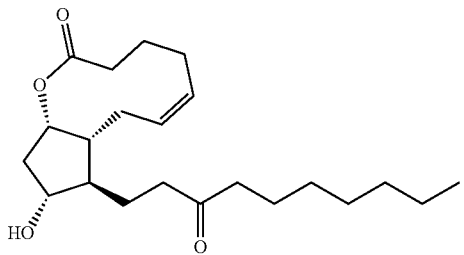 [SMILES: CCCCCCCC(=O)CC[C@@H]1[C@H]2C/C=C\CCCC(=O)O[C@H]2C[C@H]1O]

(8aR,9R,10R,11aS,Z)-9-(3-oxodecyl)-10-(tetrahydro-2H-pyran-2-yloxy)-4,5,8,8a,9,10,11,11a-octahydrocyclopenta[b]oxecin-2(3H)-one (14 g, 31 mmol) was dissolved in 140 ml methanol in 1-liter round-bottom flask. p-Toluenesulfonic acid monohydrate (0.3 g, 1.6 mmol) was added into this flask at room temperature for 3 hours. Then, the reaction mixture was quenched with 70 ml saturated NaHCO$_3$ aqueous solution and the mixture was phase separated and the aqueous layer was extracted with ethyl acetate. The organic layers were combined and dried over anhydrous MgSO$_4$. The solid was filtered off and organic solvent was evaporated off under vacuum. The crude product was purified by chromatography on silica gel using a mixture of hexane and ethyl acetate as a gradient eluent to obtain 7 g oil compound. The oil was dissolved in ethyl acetate (35 ml) at 0° C. and n-hexane (350 ml) was added while stirring for 12 h. The solid was filtrated off and washed with n-hexane to obtain 5.6 g white crystalline compound (mp 57~60° C.).

The x-ray powder diffraction pattern of the crystalline compound has characteristic peaks expressed in degrees 2θ at approximately 10.8, 14.2, 15.2, 16.2, 17.1, 20.1, 21.2, 21.9, 23.0, 25.3, 37.9, 44.1.

$^1$H-NMR (CDCl$_3$): δ 5.224~5.377 (m, 2H), 5.162 (s, 1H), 3.811 (q, 1H), 2.5592.652 (m, 2H), 2.238~2.441 (m, 6H), 1.9112.226 (m, 4H), 1.811~1.894 (m, 2H), 1.481~1.722 (m, 7H), 1.270 (m, 8H), 0.872 (t, 3H)

$^{13}$C-NMR (CDCl$_3$): δ 211.863, 173.569, 131.261, 127.458, 77.513, 73.999, 51.820, 46.249, 42.977, 41.072, 40.298, 36.093, 31.653, 29.193, 29.057, 27.394, 26.696, 25.542, 25.421, 23.842, 22.590, 14.058

Example 44

(Z)-7-[(1R,2R,3R,5S)-3,5-dihydroxy-2-3-oxodecyl-cyclopentyl]hept-5-enoic acid

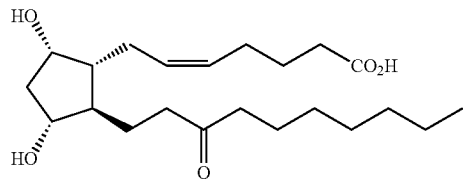 [SMILES: CCCCCCCC(=O)CC[C@@H]1[C@@H](C/C=C\CCCC(=O)O)[C@@H](O)C[C@H]1O]

(8aR,9R,10R,11aS,Z)-9-(3-oxodecyl)-10-hydroxy)-4,5,8,8a,9,10,11,11a-octahydrocyclopenta[b]oxecin-2(3H)-one (5.5 g, 15 mmol) in 60 ml 2-propanol and 8.5 ml of 3 N potassium hydroxide aqueous solution in 1-liter round-bottom flask was refluxed and stirred for 2 hours. The mixture was cooled to room temperature and adjusted to a pH of 8.5 with 3 N hydrochloric acid aqueous solution. Subsequently, 2-propanol was removed under reduced pressure and the reaction was diluted with 100 ml saturated NaHCO$_3$ aqueous solution. The basic aqueous solution was extracted with 30 ml ethyl acetate twice and the aqueous layer was adjusted to a pH of 3 with 3 N hydrochloric acid aqueous solution. Then, the acidic aqueous layer was extracted with 100 ml ethyl acetate. The organic layer was dried over anhydrous MgSO$_4$, the solid was filtered off and organic solvent was evaporated off under vacuum to obtain 6.5 g crude compound.

Determination of Isomer Content of the Product:

A sample of this product was esterified using K$_2$CO$_3$ and 2-iodopropane in DMF. After 2 h at 60° C., water and ethyl acetate were added and the mixture was extracted with ethyl acetate. After drying-concentration of the extracts, crude isopropyl Unoprostone was obtained. HPLC (Phenomenex Luna 5 μm silica) analysis of the crude product showed that no isomer was detectable, and HPLC (chiralcel OD-H) analysis of the crude product showed that no enantiomer was detectable.

$^1$H-NMR (CDCl$_3$): δ 5.320~5.458 (m, 2H), 4.128 (m, 1H), 3.862~3.870 (m, 1H), 2.540~2.652 (dd, 2H), 2.392 (t, 2H), 2.317 (t, 2H), 2.045~2.2826 (m, 8H), 1.340~1.9394 (m, 8H), 1.239 (m, 8H), 0.799~0.880 (m, 3H)

$^{13}$C-NMR (CDCl$_3$): δ 212.181, 177.956, 129.545, 129.280, 78.394, 74.242, 51.873, 51.433, 42.962, 42.400, 41.140, 33.186, 31.645, 293.178, 29.049, 27.250, 26.529, 26.423, 24.571, 23.819, 22.574, 14.043

The crude isopropyl Unoprostone could also be purified via silylation and desilylation as described in Examples 11 and 12. HPLC analysis using ODS Hypersil of the product showed that no isomer or impurity was detectable. HPLC analysis using Chiralcel OD-H of the product showed that no enantiomer was detectable.

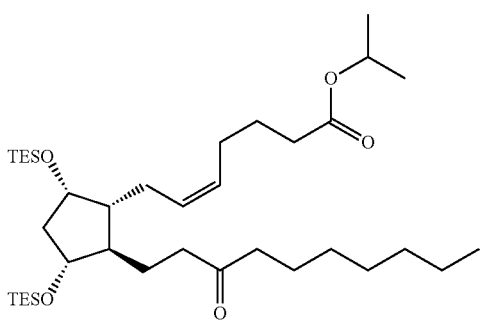

¹H-NMR (CDCl₃): δ 5.275~5.427 (m, 2H), 4.923~4.998 (m, 1H), 4.027~4.055 (m, 1H), 3.645~3.697 (m, 1H), 2.014~2.533 (m, 12H), 1.430~1.725 (m, 8H), 1.173~1.232 (m, 14H), 0.817~0.950 (m, 21H), 0.499~0.570 (m, 12H)

¹³C-NMR (CDCl₃): δ 211.308, 173.061, 129.829, 129.067, 76.709, 71.434, 67.259, 49.528, 48.275, 44.374, 42.826, 40.769, 34.142, 31.630, 29.201, 29.034, 26.711, 26.559, 25.611, 24.950, 23.895, 22.544, 21.762, 13.959, 6.794, 4.942, 4.897

Example 45

(Z)-isopropyl 7-(1R,2R,3R,5S)-3,5-dihydroxy-2-(3-oxodecylcyclopentyl)-hept-5-enoate

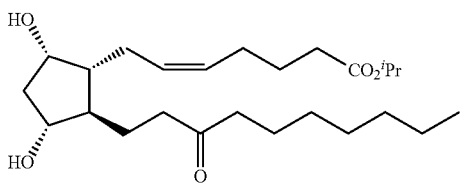

A solution of (Z)-7-[(1R,2R,3R,5S)-3,5-dihydroxy-2-3-oxodecylcyclo-pentyl]hept-5-enoic acid (6.5 g) was dissolved in 60 ml N,N-dimethylformamide in 250 ml round-bottom flask, followed by addition of potassium carbonate (6.2 g, 45 mmol) and 2-iodopropane (5.1 g, 30 mmol). The reaction mixture was heated to 80° C. and stirred for 2 hours. The mixture was cooled to room temperature and the solid was filtered off. The filtrate was subsequently extracted with 100 ml ethyl acetate and 100 ml water. The mixture was phase separated and the organic layer was dried over anhydrous MgSO₄, the solid was filtered off and organic solvent was evaporated off under vacuum. The crude product was purified by chromatography on silica gel using a mixture of hexane and ethyl acetate as a gradient eluent. Yield of the title compound was 2.4 g (37.7% in 2 steps). HPLC (Phenomenex Luna 5 μm silica) analysis of the crude product showed that no isomer was detectable, and HPLC (chiralcel OD-H) analysis of the crude product showed that no enantiomer was detectable.

¹H-NMR (CDCl₃): δ 5.362~5.409 (m, 2H), 4.942~4.985 (m, 1H), 4.126 (m, 1H), 3.851 (m, 1H), 1.901~3.061 (m, 12H), 1.181~1.778 (m, 24H), 0.843 (m, 3H)

¹³C-NMR (CDCl₃): δ 211.513, 173.402, 129.629, 129.181, 78.500, 74.288, 67.578, 52.268, 51.615, 42.955, 42.560, 14.224, 34.028, 31.637, 29.178, 29.034, 07.372, 26.666, 26.613, 24.897, 23.834, 22.559, 21.808, 14.028

Examples 46~54 Preparation of Bimatoprost and its intermediates

Example 46

(3aR,4R,5R,6aS)-hexahydro-4-((S,E)-5-phenyl-3-(tetrahydro-2H-pyran-2-yloxy) pent-1-enyl)-5-(tetrahydro-2H-pyran-2-yloxy)cyclopenta[b]furan-2-one

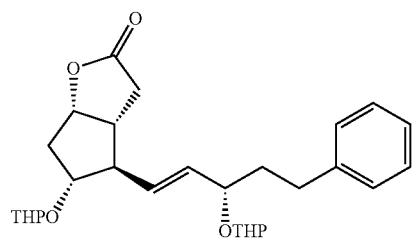

p-Toluenesulfonic acid monohydrate (0.3 g, 0.165 mmol) was added to a solution of (3aR,4R,5R,6aS)-hexahydro-5-hydroxy-4-((S,E)-3-hydroxy-5-phenylpent-1-enyl)cyclopenta[b]furan-2-one (10.0 g, 33.1 mmol) and 3,4-dihydro-2H-pyran (4.2 g, 49.7 mmol) in dichloromethane (100 mL) at room temperature and the mixture was stirred for 2.5 hr (TLC monitoring). Saturated aqueous solution of sodium bicarbonate (100 mL) was poured into the reaction mixture and the mixture was stirred for 5 minutes. The organic layer was separated and the aqueous layer was extracted with ethyl acetate (100 mL). The combined organic layers were dried over magnesium sulfate, the solid was filtered off and the filtrate was concentrated under reduced pressure to give 16.0 g of crude product. The crude product was purified by column chromatography and then concentrated under reduced pressure to provide 14.0 g of the title compound (89.9% yield).

¹H-NMR (CDCl₃): δ 7.117~7.239 (m, 5H), 5.319~5.610 (m, 2H), 4.857~4.982 (m, 1H), 4.578~4.693 (m, 2H), 4.062~4.123 (m, 1H), 3.755~3.858 (m, 2H), 3.398~3.481 (m, 2H), 2.328~2.771 (m, 7H), 1.418~2.182 (m, 16H)

Example 47

(3aR,4R,5R,6aS)-hexahydro-4-((S,E)-5-phenyl-3-(tetrahydro-2H-pyran-2-yloxy) pent-1-enyl)-5-(tetrahydro-2H-pyran-2-yloxy)-2H-cyclopenta[b]furan-2-ol

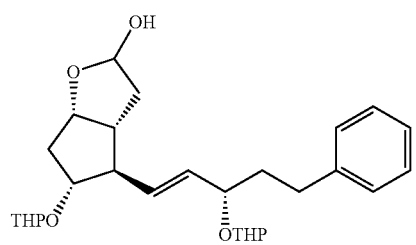

(3aR,4R,5R,6aS)-hexahydro-4-((S,E)-5-phenyl-3-(tetrahydro-2H-pyran-2-yloxy)pent-1-enyl)-5-(tetrahydro-2H-pyran-2-yloxy)cyclopenta[b]furan-2-one (14.0 g from Example 46) was dissolved in toluene (140 mL), followed by cooling to −70° C., and DIBAL (1.0M in Hexane, 45 mL) was added dropwisely. Then the reaction was quenched by adding saturated aqueous solution of ammonium chloride (10 mL) at −70° C. The resulting mixture was poured into 90 mL of a 2M sodium bisulfate aqueous solution at room temperature and stirring was continued for 30 minutes. After separation of the organic layers, 200 mL of toluene was added to the aqueous layer. The combined organic layers were concentrated under reduced pressure to give 18.0 g of crude title compound.

$^1$H-NMR (CDCl$_3$): δ 7.136~7.257 (m, 5H), 5.371~5.540 (m, 3H), 4.566~4.703 (m, 3H), 3.712~4.112 (m, 4H), 3.326~3.470 (m, 2H), 2.177~2.699 (m, 6H), 1.423~2.085 (m, 17H)

Example 48

7-((1R,2R,3R,5S)-5-hydroxy-2-((S,E)-5-phenyl-3-(tetrahydro-2H-pyran-2-yloxy) pent-1-enyl)-3-(tetrahydro-2H-pyran-2-yloxy)cyclopentyl)hept-5-enoic acid

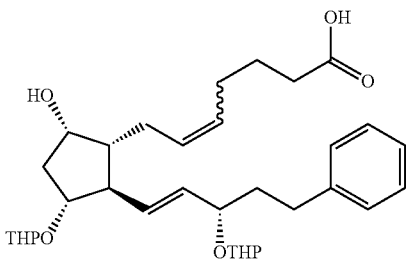

A suspension of (4-carboxybutyl)triphenylphosphonium bromide (52.8 g, 119 mmol) and potassium-tert butoxide (26.8 g, 238 mmol) in THF (400 mL) was cooled to −20° C. for 30 min. And a solution of (3aR,4R,5R,6aS)-hexahydro-4-((S,E)-5-phenyl-3-(tetrahydro-2H-pyran-2-yloxy)pent-1-enyl)-5-(tetrahydro-2H-pyran-2-yloxy)-2H-cyclopenta[b]furan-2-ol (18 g from Example 47) in 50 mL of THF at −20° C. was added and the reaction mixture was stirred for 16 hr. Then saturated aqueous solution of ammonium chloride (200 mL) was added and the resulting suspension was stirred for 30 min at room temperature. After separation of the organic layers, the aqueous layer was adjusted to a pH of 6.0 by addition of a 2M sodium bisulfate solution and extracted with 200 mL of ethyl acetate. The combined organic layers were dried over magnesium sulfate and concentrated under reduced pressure to give 32.0 g of crude title compound.

$^1$H-NMR (CDCl$_3$): δ 7.349~7.430 (m, 2H), 7.041~7.155 (m, 3H), 5.270~5.537 (m, 4H), 4.620~4.688 (m, 2H), 3.745~4.048 (m, 3H), 3.3793.554 (m, 4H), 2.404~2.688 (m, 7H), 0.810~2.179 (m, 21H)

Example 49

(6Z,8aR,9R,10R,11aS)-4,5,8,8a,9,10,11,11a-octahydro-9-((S,E)-5-phenyl-3-(tetra hydro-2H-pyran-2-yloxy)pent-1-enyl)-10-(tetrahydro-2H-pyran-2-yloxy)cyclopenta[b]oxecin-2(3H)-one

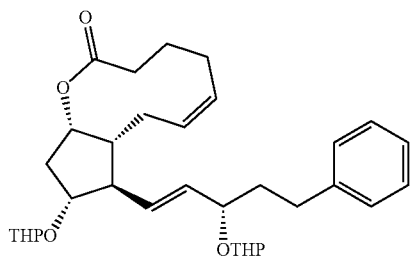

A solution of 7-((1R,2R,3R,5S)-5-hydroxy-2-((S,E)-5-phenyl-3-(tetrahydro-2H-pyran-2-yloxy)pent-1-enyl)-3-(tetrahydro-2H-pyran-2-yloxy)cyclopentyl)hept-5-enoic acid (32 g from example 48) in 320 mL dichloromethane was treated with N,N-diisopropyl-ethylamine (12.3 g, 94.8 mmol) and benzoyl chloride (7.9 g, 56.3 mmol. This mixture was then stirred for 10 minutes at room temperature under an atmosphere of nitrogen, followed by addition of 4-(dimethylamino)-pyridine (11.9 g, 97.7 mmol) at 0° C. while stirring for 10 minutes. The resulting mixture was quenched with a saturated sodium bicarbonate solution (300 mL) and extracted with dichloromethane (100 mL). The organic layer is dried over magnesium sulfate and concentrated under reduced pressure to give 29.0 g of crude product. The crude product was purified by column chromatography providing 9.4 g of the title compound (58.6% yield, 3 steps).

$^1$H-NMR (CDCl$_3$): δ 7.110~7.307 (m, 5H), 5.185~5.508 (m, 5H), 4.651~4.754 (m, 2H), 3.837~4.148 (m, 4H), 3.418~3.472 (m, 2H), 2.186~2.750 (m, 9H), 1.542~2.131 (m, 19H)

Example 50

(5Z)—N-ethyl-7-((1R,2R,3R,5S)-5-hydroxy-2-((S,E)-5-phenyl-3-(tetrahydro-2H-pyran-2-yloxy)pent-1-enyl)-3-(tetrahydro-2H-pyran-2-yloxy)cyclopentyl)hept-5-enamide

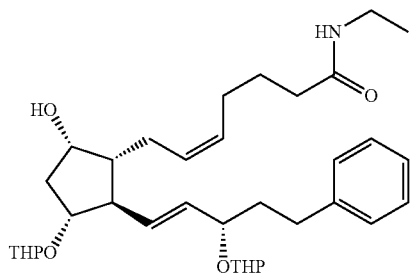

A solution of (6Z,8aR,9R,10R,11aS)-4,5,8,8a,9,10,11,11a-octahydro-9-((S,E)-5-phenyl-3-(tetrahydro-2H-pyran-2-yloxy)pent-1-enyl)-10-(tetrahydro-2H-pyran-2-yloxy)cyclopenta[b]oxecin-2(3H)-one (3.0 g, 5.57 mmol) in 15 mL tetrahydrofuran (THF) was treated with 2 M ethylamine (31 ml) in THF. This mixture was stirred and heated at 40° C. over 18 hours under an atmosphere of nitrogen. The mixture was diluted with 50 mL water and the pH was adjusted to 6 with 1N HCl. The layers were separated and the aqueous layer was extracted with 20 mL ethyl acetate twice. The organic layer is dried over magnesium sulfate and concentrated under reduced pressure. Then, the crude product was purified by column chromatography providing 2.4 g of the title compound (73.8% yield).

$^1$H-NMR (CDCl$_3$): δ 7.148~7.284 (m, 5H), 5.364~5.596 (m, 5H), 4.669~4.721 (m, 2H), 4.048~4.122 (m, 3H), 3.777~3.869 (m, 2H), 3.459 (m, 2H), 3.235 (m, 2H), 1.906~2.748 (m, 11H), 1.503~1.810 (m, 8H), 1.095 (t, 3H)

$^{13}$C-NMR (CDCl$_3$): δ 172.863, 142.160, 136.164, 135.860, 131.397 (131.352), 129.948 (129.894), 129.044 (129.006), 128.354, 125.758, 98.174 (96.178), 94.630 (94.508), 82.288 (80.959), 75.388 (75.335), 73.240 (72.754), 62.773 (62.226), 62.097 (61.589), 53.232 (52.989), 50.590 (50.454), 41.543, 39.660, 37.619 (37.573), 35.979, 34.264, 32.123, 31.607, 30.802, 30.635, 26.711, 25.656, 25.557, 25.451 (25.368), 19.683 (19.531, 19.478, 18.08), 14.885

Example 51

Bimatoprost p-Toluenesulfonic acid monohydrate (0.03 g, 0.17 mmol) was added to a stirred solution of (5Z)—N-ethyl-7-((1R,2R,3R,5S)-5-hydroxy-2-((S,E)-5-phenyl-3-(tetrahydro-2H-pyran-2-yloxy)pent-1-enyl)-3-(tetrahydro-2H-pyran-2-yloxy)cyclopentyl)hept-5-enamide (2.0 g, 3.4 mmol) in methanol (20 mL). The mixture was stirred for 2 hours at room temperature. Then, the reaction mixture was washed with saturated aqueous solution of sodium bicarbonate (50 mL). The layers were separated and the aqueous layer was extracted with ethyl acetate (20 mL). The organic layers were dried over magnesium sulfate, filtered and concentrated under reduced pressure. The residue was crystallized from hexane and ethyl acetate to give Bimatoprost in a white crystalline form (77.5% yield). UPLC (ACQUITY UPLC BEH C18) analysis of the crude product showed that no 5,6-trans isomer, 15β-isomer or any other isomers were found.

$^1$H-NMR (CDCl$_3$): δ 7.153~7.279 (m, 5H), 5.812 (m, 1H), 5.319~5.610 (m, 4H), 4.055~4.128 (m, 2H), 3.910 (m, 1H), 3.863~3.876 (m, 1H), 3.287~3.440 (m, 2H), 3.195~3.250 (m, 2H), 2.618~2.716 (m, 2H), 1.429~2.365 (m, 14H), 1.093 (t, 3H)

$^{13}$C-NMR (CDCl$_3$): δ 173.252, 142.001, 135.030, 133.093, 129.695, 129.120, 128.410, 128.333, 125.756, 77.773, 72.416, 72.189, 55.573, 50.297, 42.912, 38.738, 35.827, 34.352, 31.862, 26.663, 25.590, 25.367, 14.781

Example 52

(6Z,8aR,9R,10R,11aS)-4,5,8,8a,9,10,11,11a-octahydro-10-hydroxy-9-((S,E)-3-hydroxy-5-phenylpent-1-enyl)cyclopenta[b]oxecin-2(3H)-one

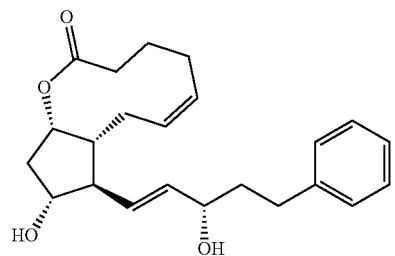 [SMILES: O=C1CCC/C=C\C[C@@H]2[C@@H](/C=C/[C@@H](O)CCc3ccccc3)[C@H](O)C[C@@H]2O1]

p-Toluenesulfonic acid monohydrate (0.16 g, 0.84 mmol) was added to a stirred solution of (6Z,8aR,9R,10R,11aS)-4,5,8,8a,9,10,11,11a-octahydro-9-((S,E)-5-phenyl-3-(tetrahydro-2H-pyran-2-yloxy)pent-1-enyl)-10-(tetrahydro-2H-pyran-2-yloxy)cyclopenta[b]oxecin-2(3H)-one (9.0 g, 16.7 mmol) in methanol (90 mL). The mixture was stirred for 2 hr at room temperature (TLC monitoring). Then, the reaction mixture was washed with saturated aqueous solution of sodium bicarbonate (100 mL). The organic layer was separated and the water layer was extracted with ethyl acetate (100 mL). The combined organic layers were dried over magnesium sulfate, filtered and concentrated under reduced pressure to give 9.0 g of crude product. The crude product was purified by column chromatography providing 3.5 g of the title compound (56.5% yield).

$^1$H-NMR (CDCl$_3$): δ 7.249~7.285 (m, 2H), 7.155~7.189 (m, 3H), 5.613~5.671 (m, 1H), 5.294~5.416 (m, 2H), 4.040~4.135 (m, 2H), 3.754 (q, 1H), 3.657 (br s, 1H), 3.311 (br s, 1H), 2.555~2.691 (m, 3H), 2.319~2.398 (m, 3H), 2.159~2.290 (m, 2H), 2.094~2.111 (m, 2H), 1.542~1.960 (m, 8H)

Example 53

(5Z)-7-((1R,2R,3R,5S)-3,5-dihydroxy-2-((S,E)-3-hydroxy-5-phenylpent-1-enyl)cyclopentyl)hept-5-enoic acid

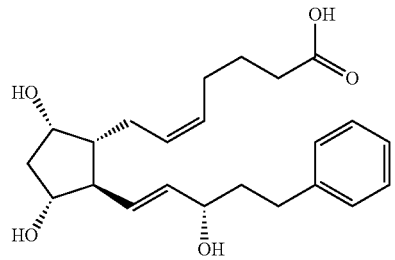

A solution of (6Z,8aR,9R,10R,11aS)-4,5,8,8a,9,10,11,11a-octahydro-10-hydroxy-9-((S,E)-3-hydroxy-5-phenylpent-1-enyl)cyclopenta[b]oxecin-2(3H)-one (2 g, 5.4 mmol) in 20 ml 2-propanol and 6.3 ml of 3 N potassium hydroxide aqueous solution in 50 mL round-bottom flask was refluxed and stirred for 2 hours. The mixture was cooled to room temperature and adjusted to a pH of 8.5 with 3 N hydrochloric acid aqueous solution. Subsequently, the 2-propanol was removed under reduced pressure and resulting mixture was diluted with 30 ml saturated NaHCO₃ aqueous solution. The basic aqueous solution was extracted with 30 ml ethyl acetate twice and the aqueous layer was adjusted to a pH of 3 with 3 N hydrochloric acid aqueous solution. Then, the acidic aqueous layer was extracted with 50 ml ethyl acetate. The organic layer was dried over anhydrous MgSO₄, the solid was filtered off and organic solvent was evaporated off under vacuum to obtain 2 g of the crude title compound.

¹H-NMR (CDCl₃): δ 7.160~7.253 (m, 5H), 5.327~5.589 (m, 4H), 4.012 (m, 2H), 3.904 (m, 2H), 1.265~2.656 (m, 18H)

¹³C-NMR (CDCl₃): δ 177.626, 141.832, 134.840, 133.160, 129.626, 129.107, 128.397, 128.351, 125.794, 77.412, 72.397, 72.305, 55.183, 49.977, 42.634, 38.443, 33.023, 31.794, 26.252, 25.176, 24.458

Example 54

(5Z)-methyl 7-((1R,2R,3R,5S)-3,5-dihydroxy-2-((S,E)-3-hydroxy-5-phenylpent-1-enyl)cyclopentyl)hept-5-enoate

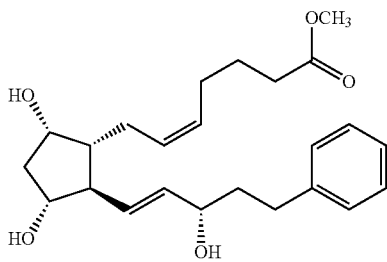 [SMILES: COC(=O)CCC/C=C\C[C@@H]1[C@@H](/C=C/[C@@H](O)CCc2ccccc2)[C@H](O)C[C@@H]1O]

A solution of (5Z)-7-((1R,2R,3R,5S)-3,5-dihydroxy-2-((S,E)-3-hydroxy-5-phenylpent-1-enyl)cyclopentyl)hept-5-enoic acid (2 g from Example 53) was dissolved in 20 ml N,N-dimethylformamide in 50 mL round-bottom flask, followed by addition of potassium carbonate (2.2 g, 16.2 mmol) and iodomethane (1.1 g, 8.1 mmol). The reaction mixture was heated to 40° C. and stirred for 2 hours. The mixture was cooled to room temperature and the solid was filtered off. The filtrate was subsequently diluted and extracted with 20 ml ethyl acetate and 20 ml water. The mixture was phase separated and the organic layer was dried over anhydrous MgSO₄, the solid was filtered off and organic solvent was evaporated off under vacuum. The crude product was purified by chromatography on silica gel using a mixture of hexane and ethyl acetate as a gradient eluent. Yield of the title compound was 1.6 g (73.5% in 2 steps)

¹H-NMR (CDCl₃): δ 7.183~7.268 (m, 5H), 5.371~5.608 (m, 4H), 4.091~4.153 (m, 2H), 3.916 (m, 1H), 3.639 (s, 3H), 2.686 (m, 3H), 1.487~2.686 (m, 16H)

¹³C-NMR (CDCl₃): δ 177.345, 141.886, 135.084, 133.067, 129.655, 129.027, 128.398, 128.349, 125.796, 77.820, 72.648, 72.227, 55.672, 51.566, 50.205, 42.840, 38.745, 33.360, 31.813, 26.581, 25.4716, 24.744.

The invention claimed is:

1. A compound selected from the group consisting of travoprost free acid containing less than 0.1% 5,6-trans isomer and less than 0.1% 15β-isomer, latanoprost free acid containing less than 0.1% 5,6-trans isomer and less than 0.1% 15β-isomer, bimatoprost free acid containing less than 0.1% 5,6-trans isomer and less than 0.1% 15β-isomer, tafluprost free acid containing less than 0.1% 5,6-trans isomer, and unoprostone containing less than 0.1% 5,6-trans isomer.

2. A compound selected from the group consisting of travoprost free acid containing less than 0.03% 5,6-trans isomer and less than 0.03% 15β-isomer, latanoprost free acid containing less than 0.03% 5,6-trans isomer and less than 0.03% 15β-isomer, bimatoprost free acid containing less than 0.03% 5,6-trans isomer and less than 0.03% 15β-isomer, tafluprost free acid containing less than 0.03% 5,6-trans isomer, and unoprostone containing less than 0.03% 5,6-trans isomer.

3. A compound according to claim 2, wherein travoprost free acid contains non-detectable levels of 5,6-trans isomer and 15β-isomer as determined by HPLC method, latanoprost free acid contains non-detectable levels of 5,6-trans isomer and 15β-isomer as determined by HPLC method, bimatoprost free acid contains non-detectable levels of 5,6-trans isomer and 15β-isomer as determined by HPLC method, tafluprost free acid contains a non-detectable level of 5,6-trans isomer as determined by HPLC method, and unoprostone contains a non-detectable level of 5,6-trans isomer as determined by HPLC method.

4. A compound according to claim 3, wherein travoprost free acid contains non-detectable levels of 5,6-trans isomer and 15β-isomer as determined by HPLC method, latanoprost free acid contains non-detectable levels of 5,6-trans isomer and 15β-isomer as determined by HPLC method, bimatoprost free acid contains non-detectable levels of 5,6-trans isomer and 15β-isomer as determined by HPLC method, tafluprost free acid contains a non-detectable level of 5,6-trans isomer as determined by HPLC method, and unoprostone contains a non-detectable level of 5,6-trans isomer as determined by HPLC method, the limit of detection of HPLC method being more than 0.02%.

* * * * *